US008372849B2

(12) United States Patent
Yen et al.

(10) Patent No.: US 8,372,849 B2
(45) Date of Patent: Feb. 12, 2013

(54) HETEROCYCLIC COMPOUNDS

(75) Inventors: Chi-Feng Yen, Taipei County (TW); Cheng-Kung Hu, Hsinchu (TW); Chang-Pin Huang, Sanchong (TW); Ying-Huey Huang, Changhua (TW); Gholam Hossein Hakimelahi, Richmond Hill (CA); Chi-Hsin Richard King, Holladay, UT (US)

(73) Assignee: Taigen Biotechnology Co., Ltd., Taipei (TW)

(*) Notice: Subject to any disclaimer, the term of this patent is extended or adjusted under 35 U.S.C. 154(b) by 876 days.

(21) Appl. No.: 12/263,671

(22) Filed: Nov. 3, 2008

(65) Prior Publication Data

US 2009/0264339 A1 Oct. 22, 2009

Related U.S. Application Data

(60) Provisional application No. 61/046,496, filed on Apr. 21, 2008.

(51) Int. Cl.
*A01N 43/54* (2006.01)
*C07D 239/42* (2006.01)
*C07D 401/04* (2006.01)

(52) U.S. Cl. ......... 514/256; 544/224; 544/330; 544/364

(58) Field of Classification Search .................. 544/224, 544/330, 364; 514/256
See application file for complete search history.

(56) References Cited

U.S. PATENT DOCUMENTS

| | | | |
|---|---|---|---|
| 5,034,560 A | 7/1991 | Cesa et al. | |
| 6,420,354 B1 | 7/2002 | Marquess et al. | |
| 2005/0124640 A1 | 6/2005 | Cardozo et al. | |
| 2006/0281712 A1* | 12/2006 | Yen et al. | 514/85 |
| 2006/0293324 A1 | 12/2006 | Yen et al. | |

FOREIGN PATENT DOCUMENTS

| | | |
|---|---|---|
| AU | 2005247943 | 12/2005 |
| AU | 2006295260 | 4/2007 |
| AU | 2006297089 | 4/2007 |
| AU | 2006318383 | 5/2007 |
| AU | 2007227602 | 9/2007 |
| EP | 834507 | 8/1998 |
| RU | 2189976 | 10/2000 |
| RU | 2243221 | 6/2003 |
| WO | WO 93/01498 | 1/1993 |
| WO | WO 95/13312 | 5/1995 |
| WO | WO 95/23609 | 9/1995 |
| WO | WO 97/20823 | 6/1997 |
| WO | WO 97/46250 | 12/1997 |
| WO | WO 98/24782 | 6/1998 |
| WO | WO 99/50249 | 10/1999 |
| WO | WO 00/20358 | 4/2000 |
| WO | WO00/53595 | 9/2000 |
| WO | WO 01/47897 | 7/2001 |
| WO | WO 02/50065 | 6/2002 |
| WO | WO 02/057259 | 7/2002 |
| WO | WO 03/024448 | 3/2003 |
| WO | WO 03/028641 | 4/2003 |
| WO | WO2003/026666 | 4/2003 |
| WO | WO2004/002964 | 1/2004 |
| WO | WO 2004/052862 | 6/2004 |
| WO | WO 2004/067516 | 8/2004 |
| WO | WO 2004/069823 | 8/2004 |
| WO | WO2005/028427 | 3/2005 |
| WO | WO 2006/138304 | * 12/2006 |
| WO | WO2006/138304 | 12/2006 |
| WO | WO2007/129195 | 11/2007 |

OTHER PUBLICATIONS

Larsen et al., "Hylan and Hylan Derivatives in Drug Deliver," Cosmetic and Pharmaceutical Applications of Polymers, 147-157, 1991.
Lofas, "Dextarn modified self-assembled monolayer surfaces for use in biointeraction analysis with surface Plasmon resonance," Pure & Appl. Chem. 67:829-834, 1995.
Prestwich, "Biomaterials from Chemically-Modified Hyaluronan," Glycoforum, 2001.
Goendoes et al., "An Efficient Synthesis of cis- and trns-2-Aminocyclohexanecarboxamides and Their N-Substituted Derivates," Liebigs Ann. Chem. 591-593, 1991.
Roberts et al., Synthesis of Some 4-Substituted Biocyclo[2.2.2]octane-1-carboxylic Acids, JACS, 75:637-640, 1953.
Kanuma et al., "Discovery of 4-(dimethylamino)quinazolines as potent and selective antagonists for the melanin-concentrating hormone receptor 1", Bioorganic & Medicinal Chemistry Letters 15:2565-2569, 2005.
Campagna et al., "A Convenient Synthesis of Nitriles from Primary Amides Under Mild Conditions," Tetrahedron Letters; the International Organ for the Rapid Publication of Preliminary Communications in Organic Chemistry, 1913-1816, 1977.
Klenke et al., "Nitrile Reduction in the Presence of Boc-Protected Amino Groups by Catalytic Hydrogeneration over Pallodium-Activated Raney-Nickel" J. Org. Chem. 66:2480-2483, 2001.
Kuo et al. "A convenient new procedure for converting primary amides into nitriles" Chem. Commun. 2007, 301-303.
Li et al. "Preparation of Fluorescent Nonpetidic Neuropeptide Y Receptor Ligands: Analogues of the Quinazoline-type AntiobesityY Antagonist CGP 71683A" Arch. Pharm, Pharm. Med. Chem. 2003, 336, 585-590.
CAS RN 355420-13-2, STN Entry Date Sep. 10, 2001 Benzaldehyde, 3-bromo -4 -(2,4 -dinitrophenoxy)-5 -methoxy:,2- [5 -fl uoro-4-(4 -morpholinyl) -2-pyrimidinyl] hy dr azone.
CAS RN 401590-15-6, STN Entry Date 18 March2 } A2 Benzaldehyde, 4-[(2-chloro-5 -fl uoro-4-pyrimidinyl)oxy] -3 -ethoxy-, 2- [5 -fl uoro-4-(4-morpholinyl) -2-pyrimidinyl]hydrazone, (2001).
CAS RN 831774-92-6, STN Entry Date Feb. 15, 2005 Benzaldehyde, 4-1U -1(2.4-dichlorophenyl)methylf-2,3,6,7 -tetrahydro-1,3-dimethyl-2,6-dioxo-1H-purin-8-ylloxyl-3-methoxy-, 1-12-[5-fluoro-4-(4-morpholinyl)-2-pyrimidinyllhydrazonel.
CAS RN 353509 -!!-Z,STN Entry DateZgAugust 2001 Benzaldehy de, 4-[(2-chloro-5 -fl uoro-4-pyrimidinyl)oxy] -, 2- [5 -fl uoro-4-(4-morpholinyl) -2-pyri midinyl]hy dr azone.

(Continued)

*Primary Examiner* — Paul V. Ward
(74) *Attorney, Agent, or Firm* — Occhiuti Rohlicek & Tsao LLP

(57) ABSTRACT

This invention relates to heterocyclic compounds of the formulas shown in the specification. It also relates to methods for treating inflammatory diseases or immune diseases, developmental or degenerative diseases, and tissue injuries with one of the heterocyclic compounds.

10 Claims, No Drawings

OTHER PUBLICATIONS

CAS RN 872521-21-6, STN Entry Date Jan. 24, 2006 Benzaldehyde, 3-[(2-chloro-S-fluoro-4-pyrimidinyl)oxy]-4-methoxy-, 2-[5-fluoro-4-(4-morpholinyl)-2-pyrimidinyl] hydrazone.

CAS RN 353509-72-3, STN Entry Date Aug. 29, 2001 Benzaldehyde, 4-[(2-chloro-5-fluoro-4-pyrimidinyl)oxy]-3-methoxy-, 2-[5-fluoro-4-(4-morpholinyl)-2-pyrimidinyl] hydrazone.

CAS RN 444801-00-7, STN Entry Date Aug. 24}OD2 Benzaldehyde, 4-(2,4-dinitrophenoxy)-3-iodo-5-methoxy-, 2-[5-fluoro-4-(4-morpholinyl)-2-pyrimidinyl] hydrazone, (2001).

* cited by examiner

HETEROCYCLIC COMPOUNDS

CROSS REFERENCE

This application claims priority to U.S. Provisional Application Ser. No. 61/046,496, filed Apr. 21, 2008, the content of which is incorporated herein by reference.

BACKGROUND

Chemokines are a family of cytokines that regulate the adhesion and transendothelial migration of leukocytes during an immune or inflammatory reaction (Mackay C. R., Nat. Immunol., 2001, 2:95; Olson et al., Am. J. Physiol. Regul. Integr. Comp. Physiol., 2002, 283:R7). Chemokines also regulate T cells and B cells trafficking and homing, and contribute to the development of lymphopoietic and hematopoietic systems (Ajuebor et al., Biochem. Pharmacol., 2002, 63:1191). Approximately 50 chemokines have been identified in humans. They can be classified into 4 subfamilies, i.e., CXC, CX3C, CC, and C chemokines, based on the positions of the conserved cysteine residues at the N-terminal (Onuffer et al., Trends Pharmacol Sci., 2002, 23:459). The biological functions of chemokines are mediated by their binding and activation of G protein-coupled receptors (GPCRs) on the cell surface.

Stromal-derived factor-1 (SDF-1) is a member of CXC chemokines. It is originally cloned from bone marrow stromal cell lines and found to act as a growth factor for progenitor B cells (Nishikawa et al., Eur. J. Immunol., 1988, 18:1767). SDF-1 plays key roles in homing and mobilization of hematopoietic stem cells and endothelial progenitor cells (Bleul et al., J. Exp. Med., 1996, 184:1101; and Gazzit et al., Stem Cells, 2004, 22:65-73). The physiological function of SDF-1 is mediated by CXCR4 receptor. Mice lacking SDF-1 or CXCR4 receptor show lethal abnormality in bone marrow myelopoiesis, B cell lymphopoiesis, and cerebellar development (Nagasawa et al., Nature, 1996, 382:635; Ma et al., Proc. Natl. Acad. Sci., 1998, 95:9448; Zou et al., Nature, 1998, 393:595; Lu et al., Proc. Natl. Acad. Sci., 2002, 99:7090). CXCR4 receptor is expressed broadly in a variety of tissues, particularly in immune and central nervous systems, and has been described as the major co-receptor for HIV-1/2 on T lymphocytes. Although initial interest in CXCR4 antagonism focused on its potential application to AIDS treatment (Bleul et al., Nature, 1996, 382:829), it is now becoming clear that CXCR4 receptor and SDF-1 are also involved in other pathological conditions such as rheumatoid arthritis, asthma, and tumor metastases (Buckley et al., J. Immunol., 2000, 165: 3423). Recently, it has been reported that a CXCR4 antagonist and an anticancer drug act synergistically in inhibiting cancer such as acute promuelocutic leukemia (Liesveld et al., Leukemia Research 2007, 31:1553). Further, the CXCR4/SDF-1 pathway has been shown to be critically involved in the regeneration of several tissue injury models. Specifically, it has been found that the SDF-1 level is elevated at an injured site and CXCR4-positive cells actively participate in the tissue regenerating process.

SUMMARY

This invention is based on the discovery that certain compounds (1) are effective in inhibiting the binding between SDF-1 and chemokine receptors (e.g., CXCR3 or CXCR4 receptors), and (2) exhibit synergistic effects in stem cells and endothelial progenitor cells mobilization, when used in combination with a granulocyte-colony stimulating factor (G-CSF).

In one aspect, this invention relates to compounds of the following formula:

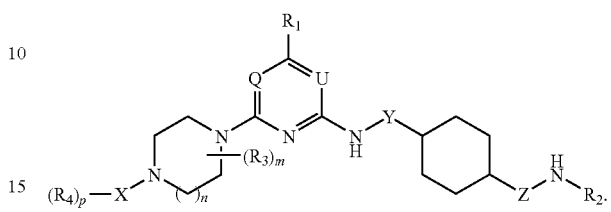

In this formula, each of Q and U is CH or N, provided that at least one of Q and U is N; each of X, Y, and Z, independently, is $C_{1-5}$ alkylene or deleted; m is 0, 1, 2, 3, 4, or 5; n is 0, 1 or 2; p is 1 or 2; $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is $C_1$-$C_{10}$ alkyl, $C_3$-$C_{20}$ cycloalkyl, $C_1$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_1$-$C_{20}$ heterocycloalkyl, or $N(R_cR_d)$; $R_3$, independently, is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; and $R_4$ is $P(=O)(OR_g)(OR_i)$, $P(=O)(NHR_g)(OR_i)$, $P(=O)(NR_g)(NR_i)$, $S(=O)_2OR_g$, or $S(=O)_2R_g$; in which each of $R_a$, $R_b$, $R_c$, $R_d$, $R_e$, $R_f$, $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_c$ and $R_d$ are linked and together form $C_{2-8}$ alkylene, $R_e$ and $R_f$ are linked and together form $C_{2-8}$ alkylene, or $R_g$ and $R_i$ are linked and together form $C_{1-5}$ alkylene.

The just-described compounds may have one or more of the following features: U is N; X is —$CH_2$—, —$CH_2CH_2$— or —$CH_2CH_2CH_2$— and p is 1, or X is

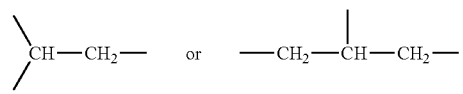

and p is 2; Y is —$CH_2$ or deleted; Z is —$CH_2$—; m is 0, 1, or 2; n is 1 or 2; $R_1$ is $NH_2$; $R_2$ is $C_{1-5}$ alkyl substituted $N(R_cR_d)$, e.g., —$CH_2CH_2$—$N(R_cR_d)$ or —$CH_2CH_2CH_2$— $N(R_cR_d)$, in which $R_c$ is H and $R_d$ is $C_1$-$C_{10}$ alkyl, $C_3$-$C_{20}$ cycloalkyl, $C_1$-$C_{20}$ heterocycloalkyl, aryl, or heteroaryl, or $R_c$ and $R_d$ are linked and together form $C_{4-6}$ alkylene; $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached; and $R_4$ is $P(=O)(OH)_2$, $P(=O)(OH)(OCH_2CH_3)$, $P(=O)(OCH_2CH_3)_2$,

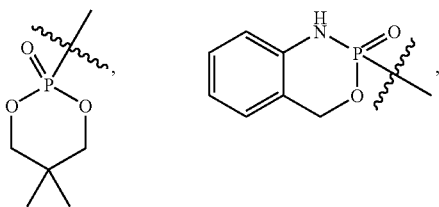

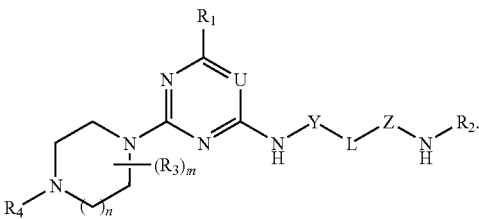

S(=O)₂OH, S(=O)₂CH₃, or S(=O)₂Ph.

In another aspect, this invention relates to compounds of the above formula, in which each of Q and U is N or CH, provided at least one of them is N; each of X, Y, and Z, independently, is $C_{1-5}$ alkylene or deleted, m is 1, 2, 3, 4, or 5; n is 0, 1 or 2; $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is $C_1$-$C_{10}$ alkyl, $C_3$-$C_{20}$ cycloalkyl, $C_1$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_1$-$C_{20}$ heterocycloalkyl, or $N(R_cR_d)$; $R_3$ is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; and $R_4$ is H, $C_1$-$C_{10}$ alkyl, $C_3$-$C_{20}$ cycloalkyl, $C_1$-$C_{20}$ heterocycloalkyl, aryl, heteroaryl, $OR_g$, $COOR_g$, $C(O)R_g$, $P(=O)(OR_g)(OR_i)$, $P(=O)(NHR_g)(OR_i)$, $P(=O)(NR_g)(NR_i)$, $S(=O)_2OR_g$, or $S(=O)_2R_g$; in which each of $R_a$, $R_b$, $R_c$, $R_d$, $R_e$, $R_f$, $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_c$ and $R_d$ are linked and together form $C_{2-8}$ alkylene, $R_e$ and $R_f$ are linked and together form $C_{2-8}$ alkylene, or $R_g$ and $R_i$ are linked and together form $C_{2-8}$ alkylene.

The just-described compounds may have one or more of the following features: U is N; X is —CH₂—, —CH₂CH₂—, —CH₂CH₂CH₂—, or deleted; Y is —CH₂ or deleted; Z is —CH₂—; m is 1 or 2; n is 1 or 2; $R_1$ is NH₂; $R_2$ is $C_{1-5}$ alkyl substituted $N(R_cR_d)$, e.g., —CH₂CH₂—N($R_cR_d$) or —CH₂CH₂CH₂—N($R_cR_d$), in which $R_c$ is H and $R_d$ is $C_1$-$C_{10}$ alkyl, $C_3$-$C_{20}$ cycloalkyl, $C_1$-$C_{20}$ heterocycloalkyl, aryl, or heteroaryl, or $R_c$ and $R_d$ are linked and together form $C_{4-6}$ alkylene; $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached; and $R_4$ is P(=O)(OH)₂, P(=O)(OH)(OCH₂CH₃), P(=O)(OCH₂CH₃)₂,

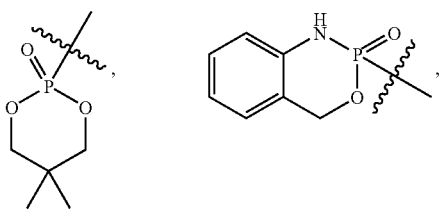

S(=O)₂OH, S(=O)₂CH₃, or S(=O)₂Ph.

In still another aspect, this invention relates to compounds of the following formula:

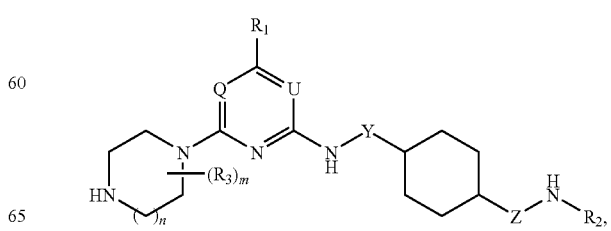

In this formula, U is CH or N; L is $C_1$-$C_{10}$ alkyl, $C_3$-$C_{20}$ cycloalkyl, $C_1$-$C_{20}$ heterocycloalkyl, aryl, or heteroaryl; each of Y and Z, independently, is $C_{1-5}$ alkylene or deleted; m is 0, 1, 2, 3, 4, or 5; n is 0, 1 or 2; $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is $C_1$-$C_{10}$ alkyl, $C_3$-$C_{20}$ cycloalkyl, $C_1$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_1$-$C_{20}$ heterocycloalkyl, or $N(R_cR_d)$; $R_3$ is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; and $R_4$ is H, $C_1$-$C_{10}$ alkyl, $C_3$-$C_{20}$ cycloalkyl, $C_1$-$C_{20}$ heterocycloalkyl, aryl, heteroaryl, $OR_g$, $COOR_g$, $C(O)R_g$, or $C(O)NR_gR_i$; in which each of $R_a$, $R_b$, $R_c$, $R_d$, $R_e$, $R_f$, $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_c$ and $R_d$ are linked and together form $C_{2-8}$ alkylene, $R_e$ and $R_f$ are linked and together form $C_{2-8}$ alkylene, or $R_g$ and $R_i$ are linked and together form $C_{2-8}$ alkylene.

The just-described compounds may have one or more of the following features: U is N; Y is —CH₂ or deleted; Z is —CH₂—; m is 1 or 2; n is 1 or 2; L is cyclohexyl; $R_1$ is NH₂; $R_2$ is $C_{1-5}$ alkyl substituted $N(R_cR_d)$, e.g., —CH₂CH₂—N($R_cR_d$) or —CH₂CH₂CH₂—N($R_cR_d$), in which $R_c$ is H and $R_d$ is $C_1$-$C_{10}$ alkyl, $C_3$-$C_{20}$ cycloalkyl, $C_1$-$C_{20}$ heterocycloalkyl, aryl, or heteroaryl, or $R_c$ and $R_d$ are linked and together form $C_{4-6}$ alkylene; $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached; and $R_4$ is H or $C_1$-$C_3$ alkyl optionally substituted with $OR_g$, $CO_2R_g$, $NR_gR_i$, $P(=O)(OR_g)(OR_i)$, $P(=O)(NHR_g)(OR_i)$, $P(=O)(NR_g)(NR_i)$, $S(=O)_2OR_g$, or $S(=O)_2R_g$; in which each of $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_g$ and $R_i$ are linked and together form $C_{1-5}$ alkylene.

In still another aspect, this invention relates to compounds of the following formula:

In this formula, each of Q and U is N or CH, provided at least one of them is N; each of Y and Z, independently, is $C_{1-5}$ alkylene or deleted; m is 0, 1, 2, 3, 4, or 5; n is 0, 1 or 2; $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is $C_1$-$C_{10}$ alkyl, $C_3$-$C_{20}$ cycloalkyl, $C_1$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_1$-$C_{20}$ heterocycloalkyl, or $N(R_cR_d)$; and $R_3$ is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; in which each of $R_a$, $R_b$, $R_c$, $R_d$, $R_e$, and $R_f$ independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_c$ and $R_d$ are linked and together form $C_{2-8}$ alkylene, or $R_e$ and $R_f$ are linked and together form $C_{2-8}$ alkylene.

The just-described compounds may have one or more of the following features: U is N; Y is —$CH_2$ or deleted; Z is —$CH_2$—; m is 0, 1 or 2; n is 1 or 2; $R_1$ is $NH_2$; $R_2$ is $C_{1-5}$ alkyl substituted $N(R_cR_d)$, e.g., —$CH_2$—$N(R_cR_d)$ or —$CH_2CH_2$—$N(R_cR_d)$, in which $R_c$ is H and $R_d$ is $C_1$-$C_{10}$ alkyl, $C_3$-$C_{20}$ cycloalkyl, $C_1$-$C_{20}$ heterocycloalkyl, aryl, or heteroaryl, or $R_c$ and $R_d$ are linked and together form $C_{4-6}$ alkylene; $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached;

In still another aspect, this invention relates to compounds of the following formula:

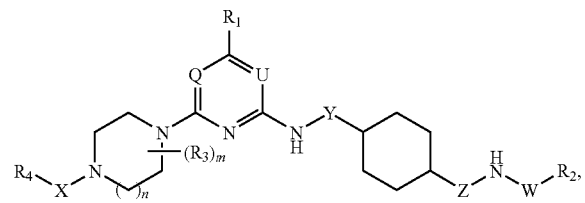

In the formula, each of Q and U is N or CH, provided at least one of them is N; each of W, X, Y, and Z, independently, is $C_{1-5}$ alkylene or deleted; m is 0, 1, 2, 3, 4, or 5; n is 0, 1 or 2; $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is piperidin-1-yl, (bicyclo[2.2.1]heptanyl)amino, (cyclohexylmethyl)amino, (2,3-dihydro-1H-inden-2-yl)amino, phenylamino, or benzylamino; $R_3$ is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$ or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; and $R_4$ is H, $C_1$-$C_{10}$ alkyl, $C_3$-$C_{20}$ cycloalkyl, $C_1$-$C_{20}$ heterocycloalkyl, aryl, heteroaryl, $OR_g$, $COOR_g$, $C(O)R_g$, or $C(O)NR_gR_i$; in which each of $R_a$, $R_b$, $R_e$, $R_f$, $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_e$ and $R_f$ are linked and together form $C_{2-8}$ alkylene, or $R_g$ and $R_i$ are linked and together form $C_{2-8}$ alkylene.

The just-described compounds may have one or more of the following features: U is N; X is —$CH_2$—, —$CH_2CH_2$— or —$CH_2CH_2CH_2$—; Y is —$CH_2$ or deleted; Z is —$CH_2$—; W is —$CH_2CH_2$—; m is 1 or 2; n is 1 or 2; $R_1$ is $NH_2$; and $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached.

The term "alkyl" refers to a saturated or unsaturated, linear or branched hydrocarbon moiety, such as —$CH_3$, —$CH_2$—$CH$=$CH_2$, or branched —$C_3H_7$. The term "alkylene" refers to a divalent or multivalent, saturated or unsaturated, linear or branched hydrocarbon moiety, such as —$CH_2$—,

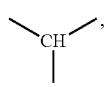

—$CH_2CH_2$—,

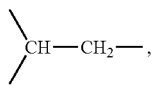

—$CH_2CH_2CH_2$—,

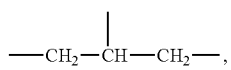

or —CH=CH—. The term "cycloalkyl" refers to a saturated or unsaturated, non-aromatic, monocyclic, bicyclic, tricyclic, or tetracyclic hydrocarbon moiety, such as cyclohexyl, cyclohexen-3-yl, or adamantyl. The term "heterocycloalkyl" refers to a saturated or unsaturated, non-aromatic, monocyclic, bicyclic, tricyclic, or tetracyclic moiety having one or more ring heteroatoms (e.g., N, O, or S), such as 4-tetrahydropyranyl or 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkylene, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl and alkylene include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl can also be fused with each other.

The compounds described above include the compounds themselves, as well as their salts, prodrugs, and solvates, if applicable. A salt, for example, can be formed between an anion and a positively charged group (e.g., amino) on a compound having one of the above formulas. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound having one of the above formulas. Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

In still another aspect, this invention relates to a method for treating a medical condition related to CXCR4, such as an inflammatory or immune disease, a developmental or degenerative disease, a tissue injury, or cancer. The method includes administering to a subject in need thereof an effective amount of one or more compounds of formula (I) shown above.

An inflammatory disease is characterized by a local or systemic, acute or chronic inflammation. Examples include retinopathy (e.g., diabetic retinopathy and proliferative retinopathy), inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), macular edema, asthma, and allergic rhinitis.

An immune disease is characterized by a hyper- or hypo-reaction of the immune system. Examples include, but are not limited to, autoimmune diseases (e.g., rheumatoid arthritis, psoriatic arthritis, systemic lupus erythematosus, myasthenia gravis, Type I diabetes mellitus, glomerulonephritis, autoimmune throiditis, ankylosing spondylitis, systemic sclerosis, and multiple sclerosis), acute and chronic inflammatory diseases (e.g., systemic anaphylaxis or hypersensitivity responses, drug allergies, insect sting allergies, graft rejection, including allograft rejection, and graft-versus-host disease), Sjogren's syndrome, and human immunodeficiency virus infection.

Developmental diseases are growth or differentiation related disorders that lead to loss-of-function or gain-of-function. Degenerative diseases generally refer to change of a tissue to a lower or less functional form. Examples of a developmental or degenerative disease include age-related macular degeneration, corneal neovascularization, iris neovascularization, spinal muscular atrophy, Duchenne muscular dystrophy, Parkinson's disease, and Alzheimer's disease. Tissue injuries can be caused by oxidative stress (e.g., ischemia-reperfusion in stroke or myocardial infarction), complement activation, graft rejection, chemicals (e.g., alcohol-induced liver damage or mucosal tissue injuries in cancer therapy), viral infection (e.g., glomerular injuries associated with hepatitis C infection), and mechanical forces (e.g., sports injury). Examples of tissue injuries include brain injury, nerve injury, heart injury, liver damage, skeletal muscle injury, kidney damage, pancreatic injury, lung injury, skin injury, limb ischemia, silent ischemia, cardiac ischemia, and gastrointestinal tract injury.

Cancer is a class of diseases in which a group of cells having the capacity for autonomous growth, i.e., an abnormal state or condition characterized by rapidly proliferating cell growth and sometimes tumor metastasis. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, colon cancer, kidney cancer, thyroid cancer, haematopoietic cancer, and cancer of unknown primary site.

A subject in need of the above-described treatment can also be concurrently administered with an effective amount of one of the heterocyclic compounds described above and an effective amount of one or more other therapeutic agents. The therapeutic agents include a G-CSF, a steroidal or a non-steroidal anti-inflammatory drug, a chemotherapeutic agent, an anti-angiogenesis agent, a COX2 inhibitor, a leukotriene receptor inhibitor, a prostaglandin modulator, a TNF modulator, and an immunosuppressive agent (e.g., cyclosporine A). For example, one can use a combination of a compound of this invention and a chemotherapeutic agent to treat cancers, either hematological cancer or solid cancer. Without being bound by theory, in treating hematological cancer (e.g., acute myeloid leukemia and acute lymphoblastic leukemia), the heterocyclic compound acts as a "chemosensitizer" to mobilize cancer cells from bone marrow and the chemotherapeutic agent and then kills these cancer cells, thereby resulting in enhanced treatment effect. Also, without being bound by theory, in treating solid cancer, the heterocyclic compound acts as an anti-angiogenesis agent, and, when used together with a chemotherapeutic agent, enhances treatment effect. As another example, one can use a compound of this invention and another anti-agiogenesis agent to treat retinopathy, age-related macular degeneration, macular edema, corneal neovascularization, or iris neovascularization. G-CSF is a haematopoietic growth factor that stimulates the bone marrow to produce more white blood cells. A chemotherapeutic agent is a drug that inhibits cancer cell growth or a cytotoxic agent. An anti-angiogenesis agent is a drug that confers its therapeutical effects via inhibiting the angiogenesis process. Examples of angiogenesis agents include, but are not limited to, Avastin, Lucentis, Sunitinib, and Sorafenib. The term "concurrently administered" refers to administering two or more active agents at the same time or at different times during the period of treatment. An example of concurrent administration is to apply a solid or liquid mixture of the two or more active agents to a patient.

In yet another aspect, this invention relates to a method for enhancing migration of bone marrow-derived cells to blood. The method includes administering to a subject in need thereof an effective amount of one or more compounds of formula (I) shown above. The term "bone marrow-derived cells" refers to cells originating from bone marrow. Examples of bone marrow-derived cells include, but are not limited to, CD34+ cells and CD133+ cells. Preferably, bone marrow-derived cells are stem cells or endothelial progenitor cells. In this method, an effective amount of a G-CSF growth factor may also be used.

Also within the scope of this invention is a composition containing one or more of the compounds and a pharmaceutically acceptable carrier described above for use in treating an above-described medical condition, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary compounds, compounds 1-150, of this invention:

Compound 1

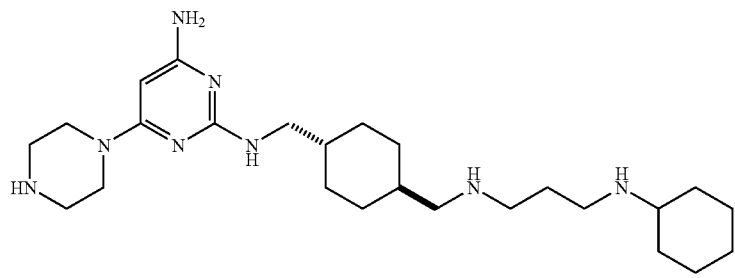

Compound 2

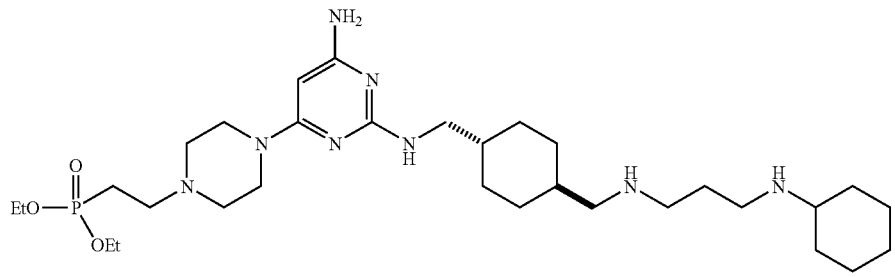

Compound 3

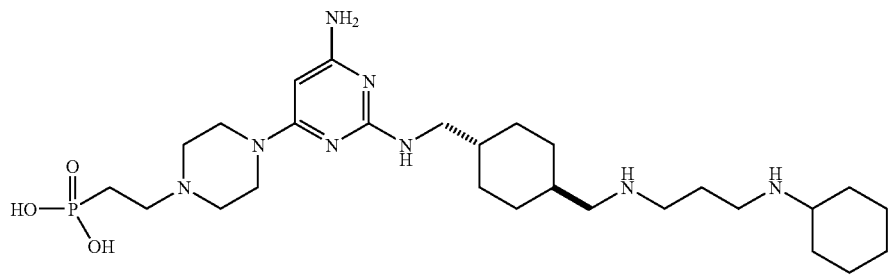

Compound 4

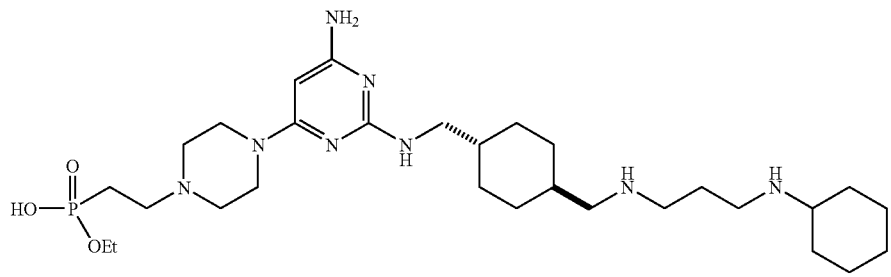

Compound 5

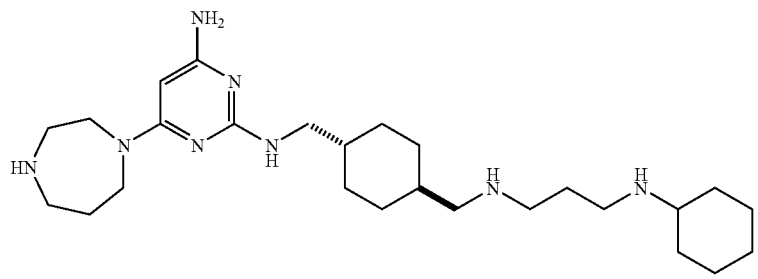

-continued
Compound 6
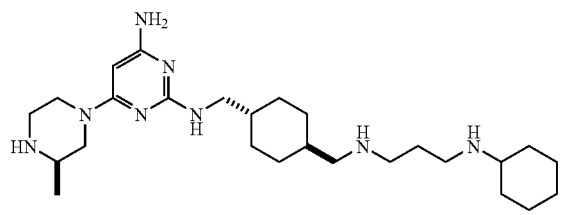
Compound 7
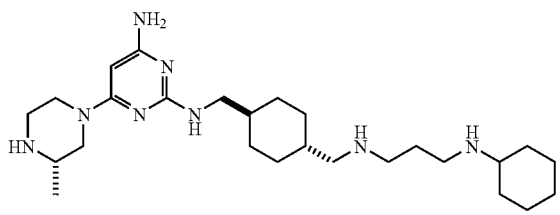
Compound 8
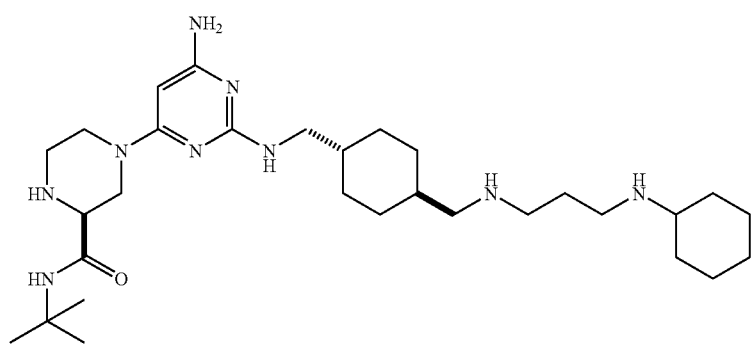
Compound 9
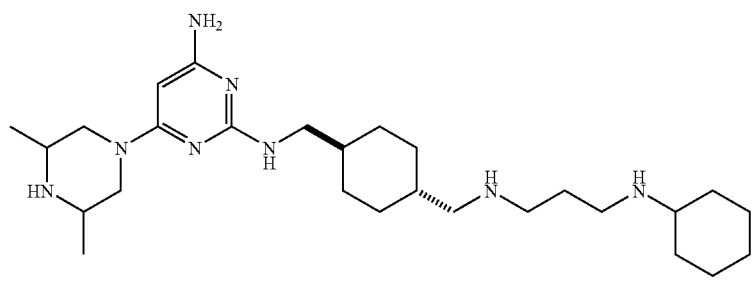
Compound 10
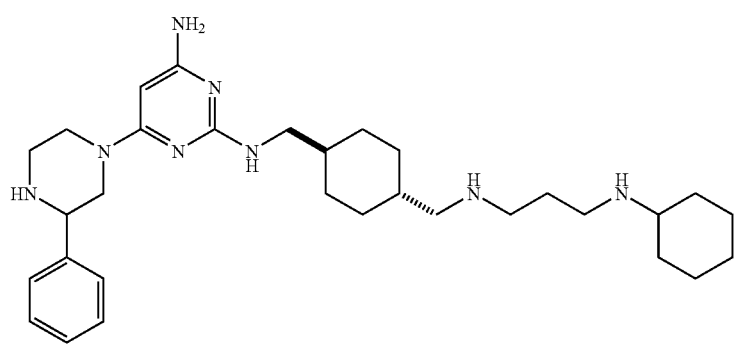
Compound 11
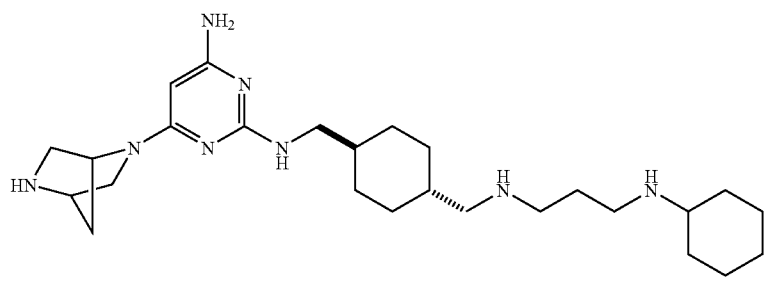

-continued
Compound 12
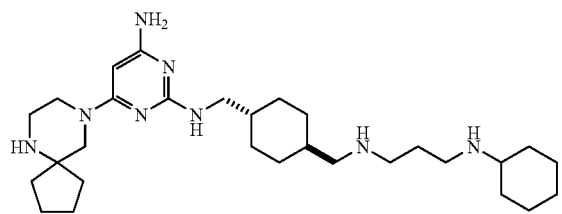
Compound 13
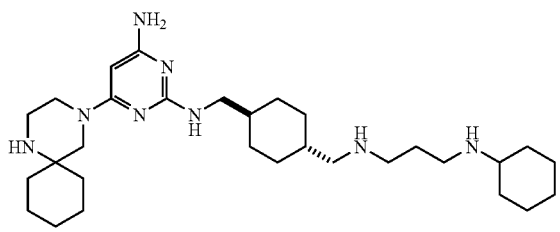
Compound 14
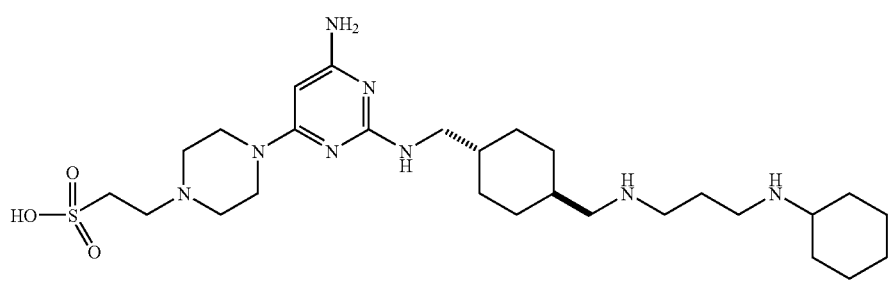
Compound 15
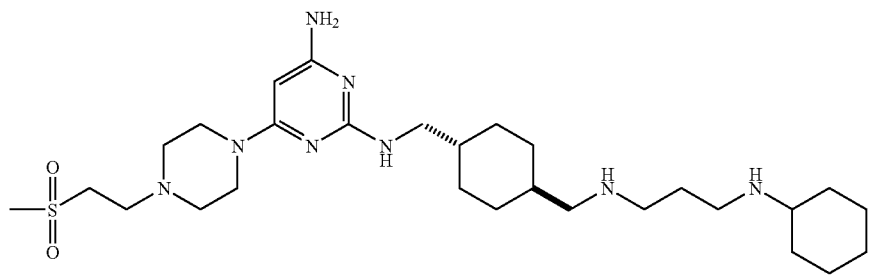
Compound 16
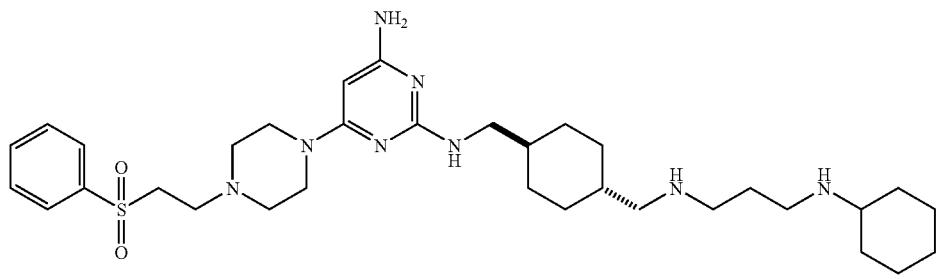
Compound 17
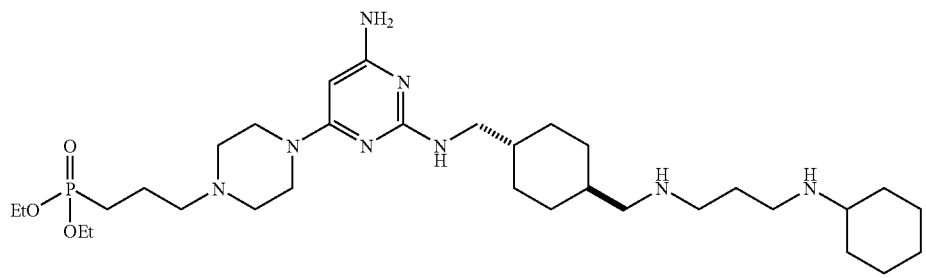
Compound 18
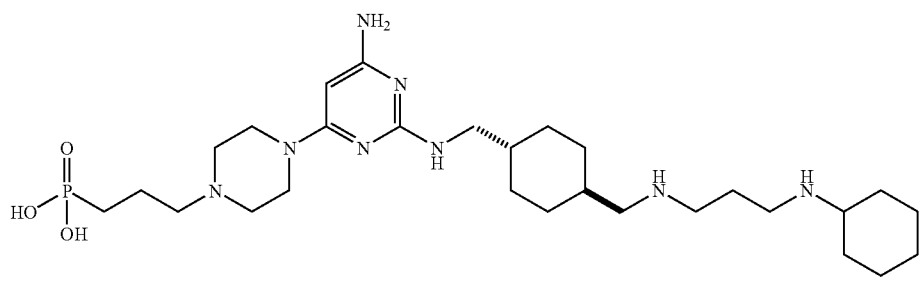

Compound 19
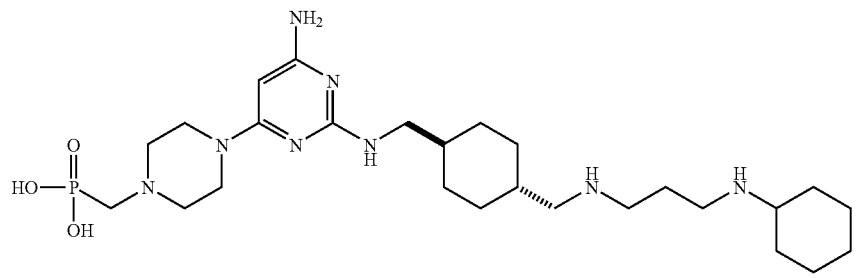
Compound 20
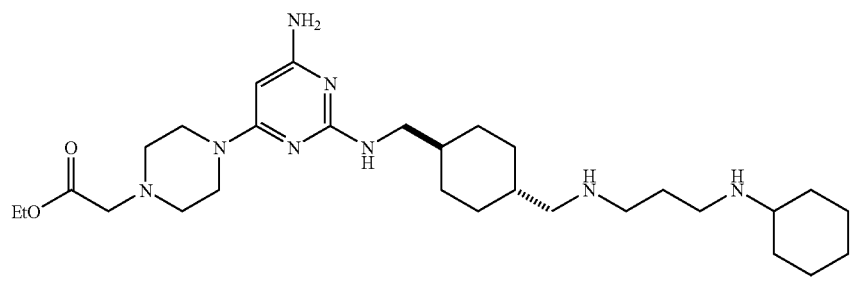
Compound 21
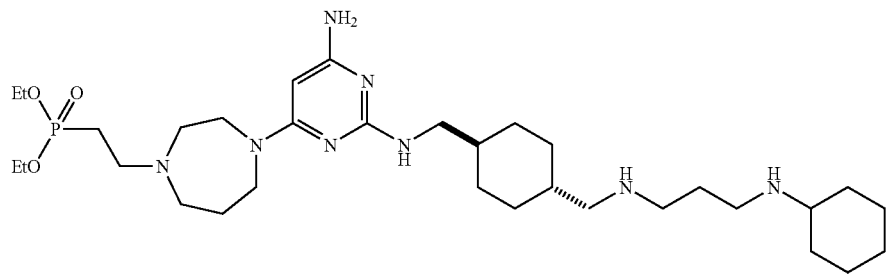
Compound 22
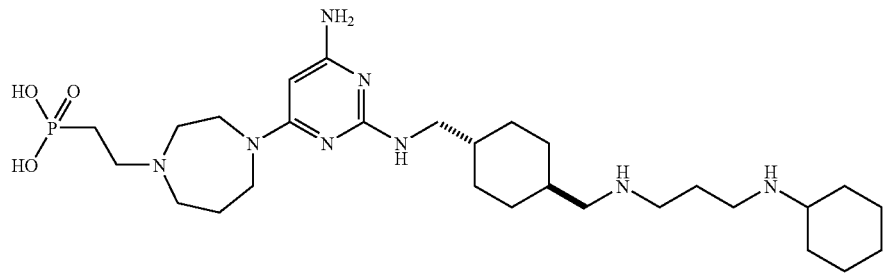
Compound 23
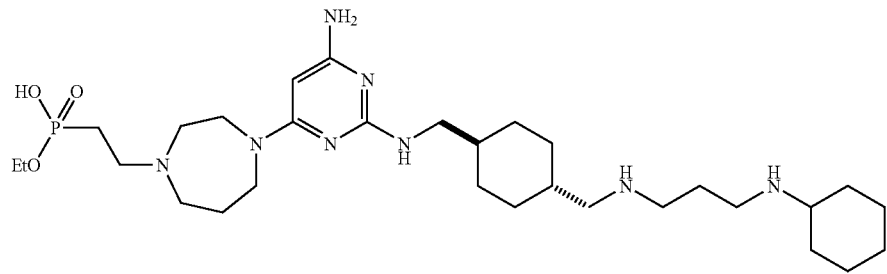

Compound 24
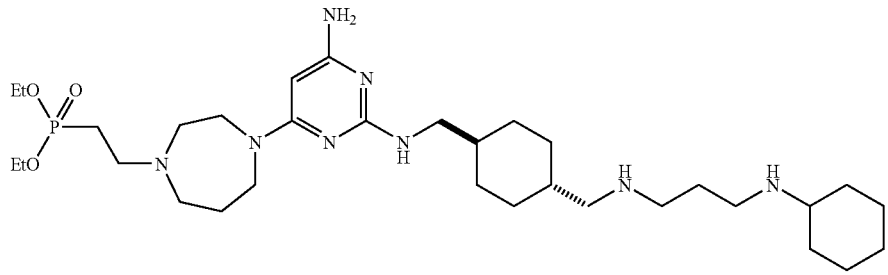
Compound 25
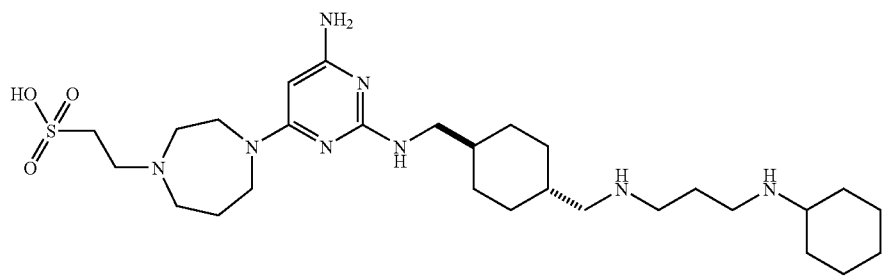
Compound 26
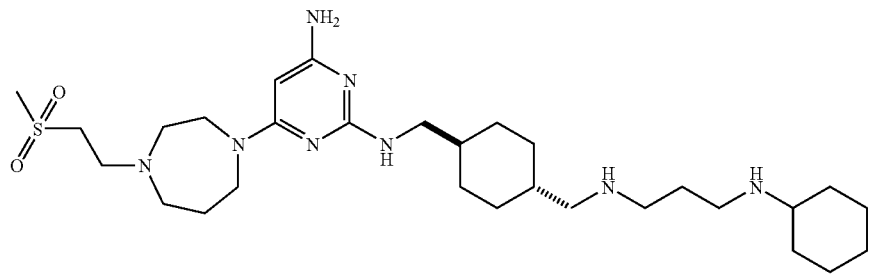
Compound 27
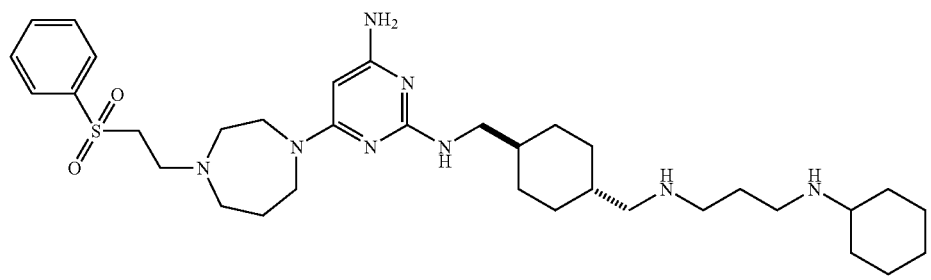
Compound 28
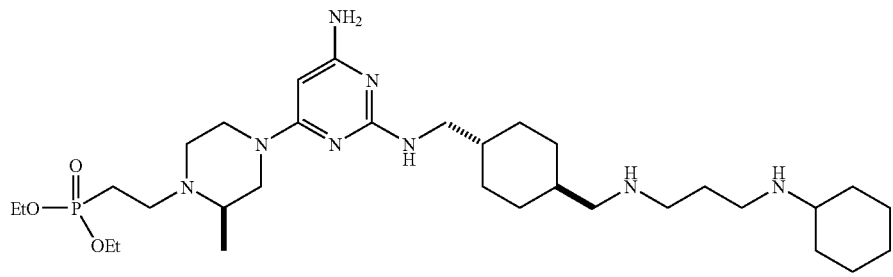

-continued
Compound 29
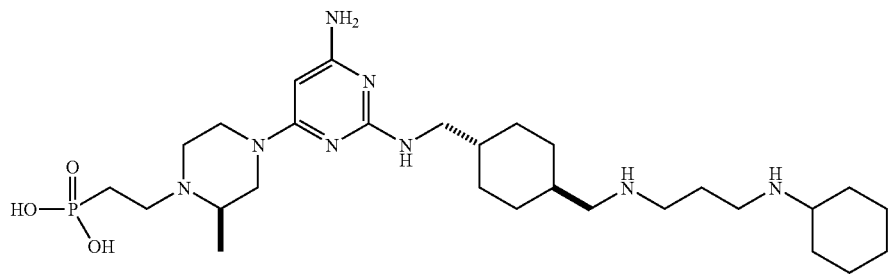
Compound 30
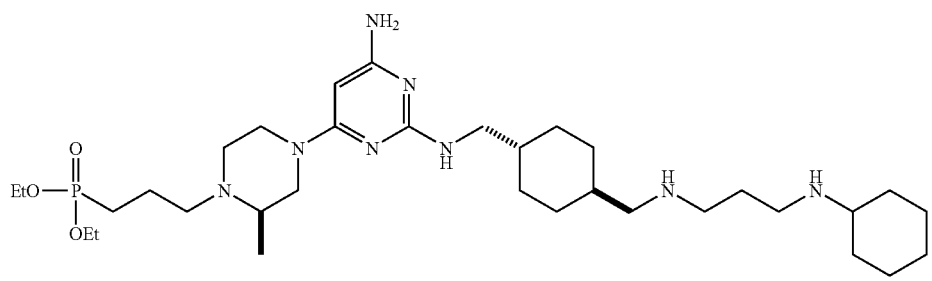
Compound 31
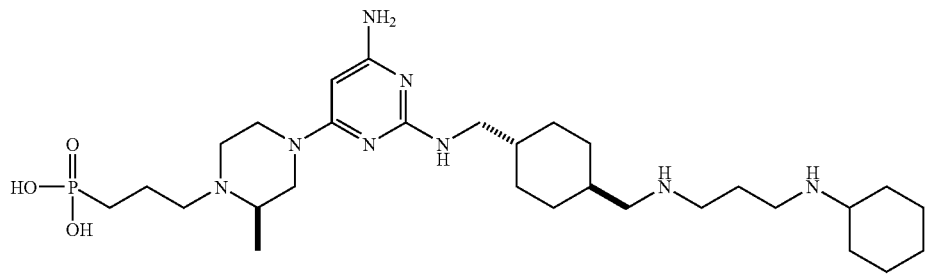
Compound 32
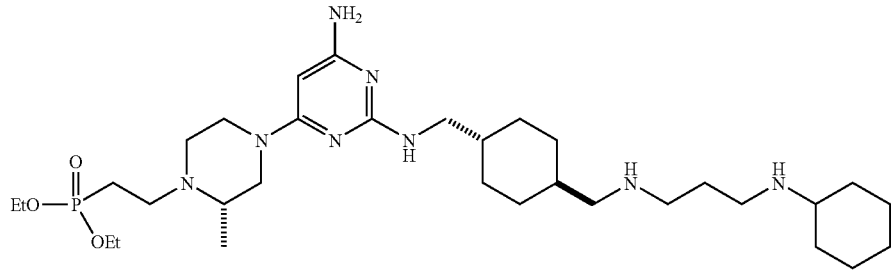
Compound 33
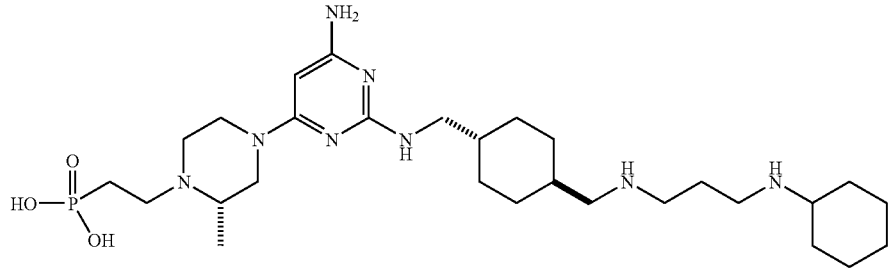

-continued
Compound 34
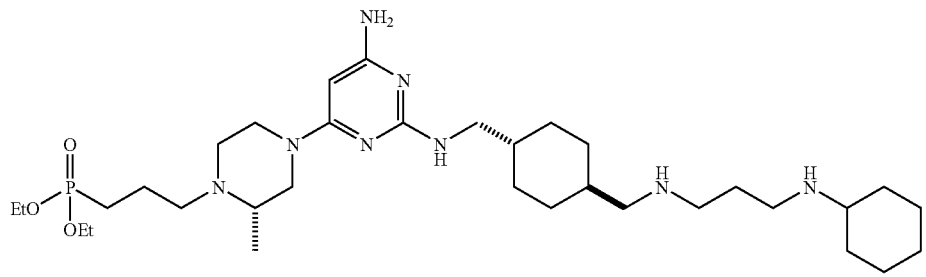
Compound 35
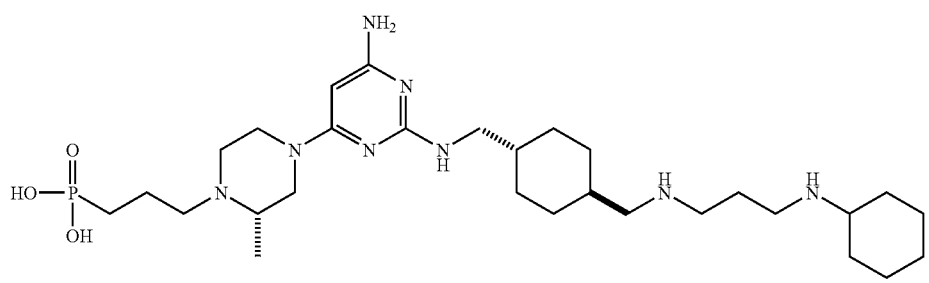
Compound 36
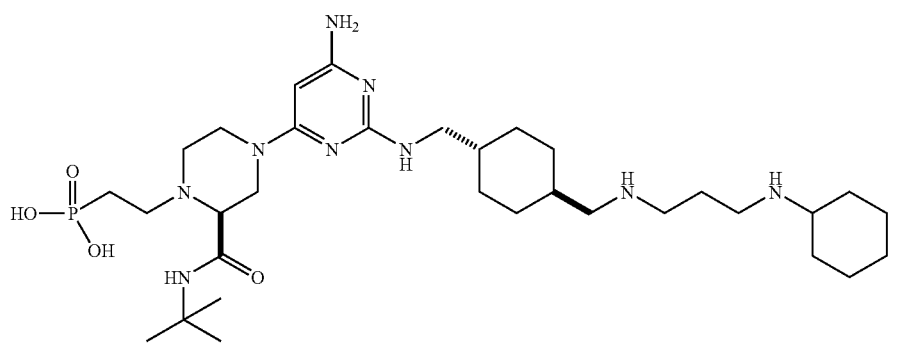
Compound 37
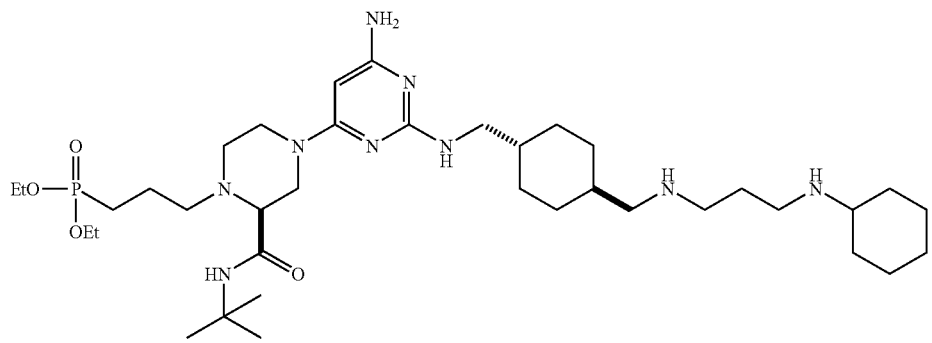
Commpound 38
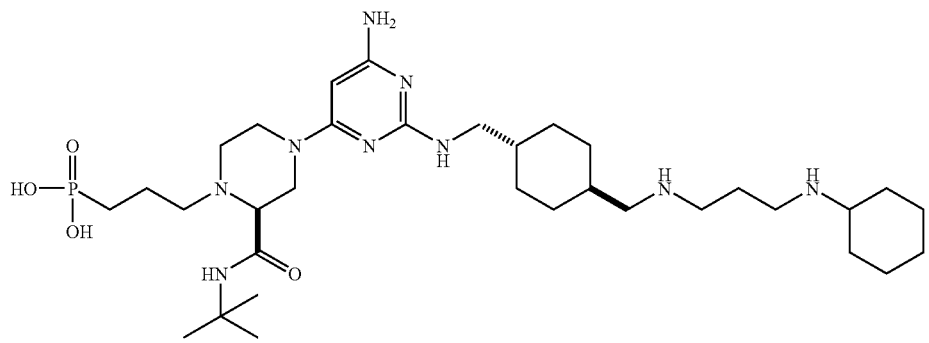

-continued
Compound 39
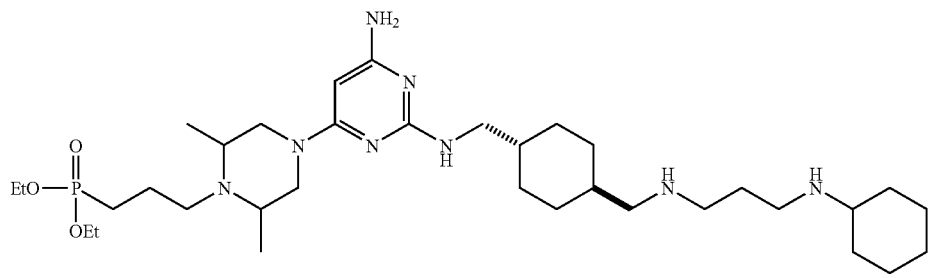
Compound 40
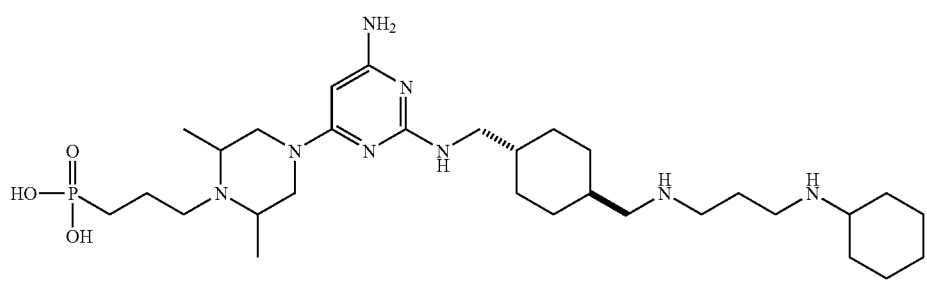
Compound 41
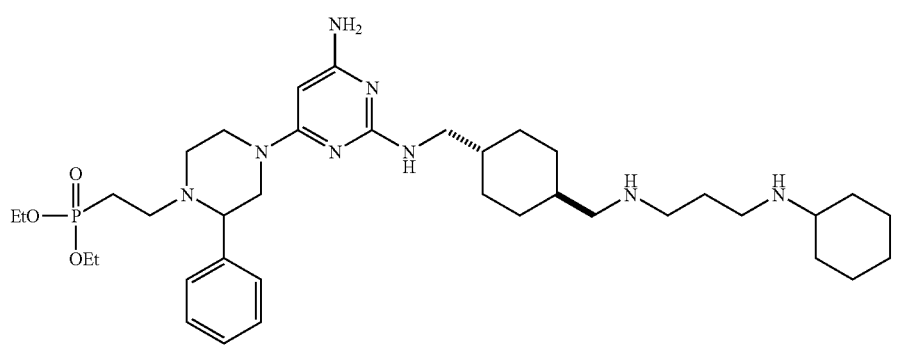
Compound 42
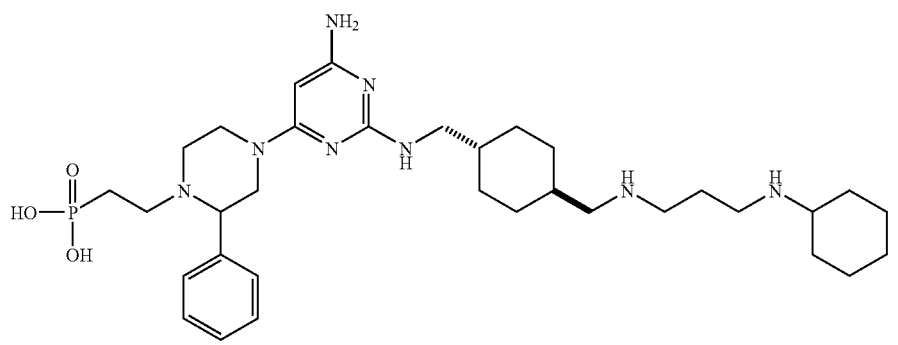
Compound 43
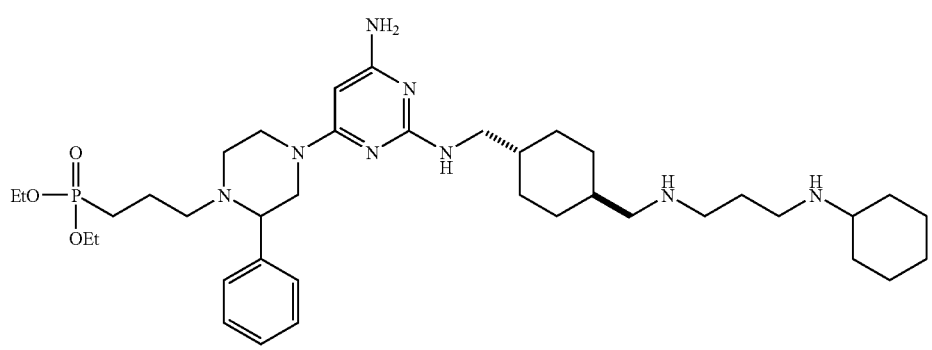

Compound 44
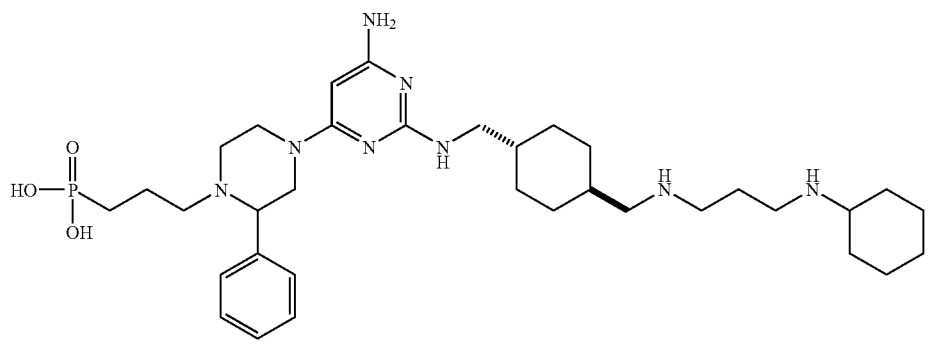
Compound 45
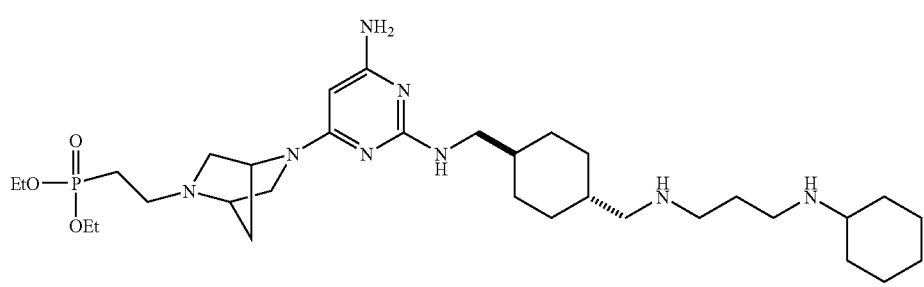
Compound 46
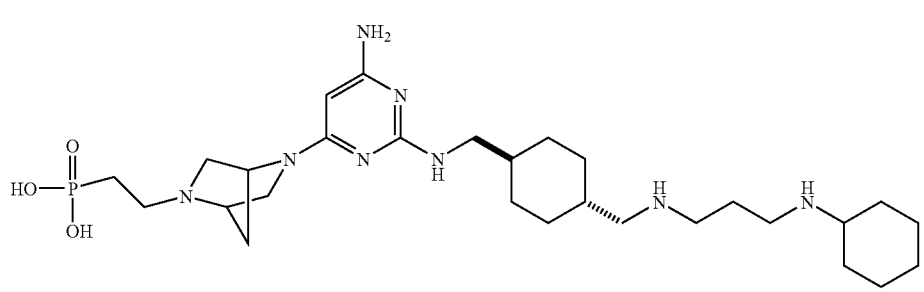
Compound 47
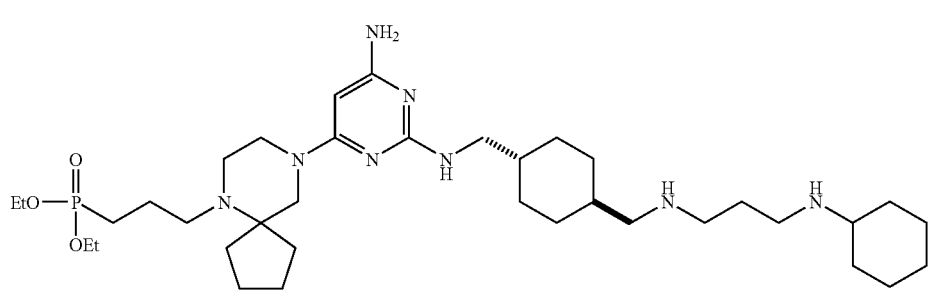
Compound 48
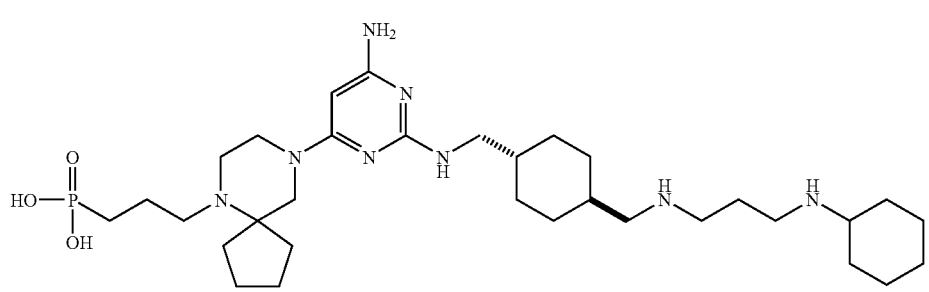

-continued
Compound 49
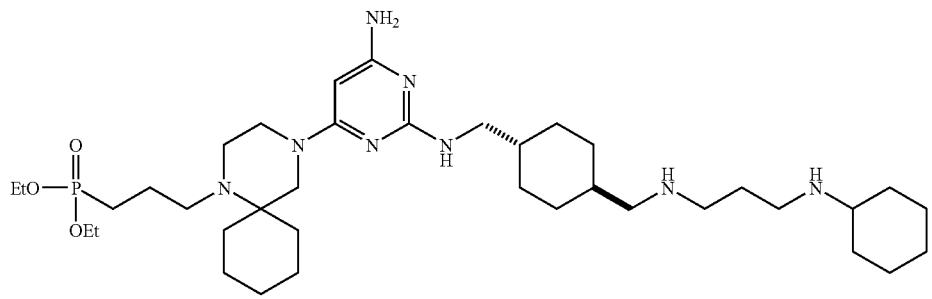
Compound 50
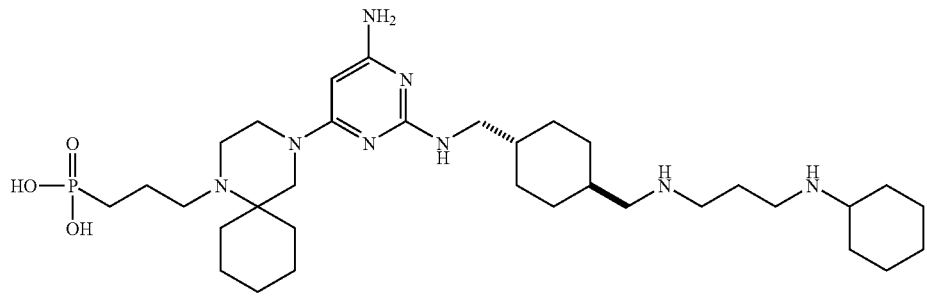
Compound 51
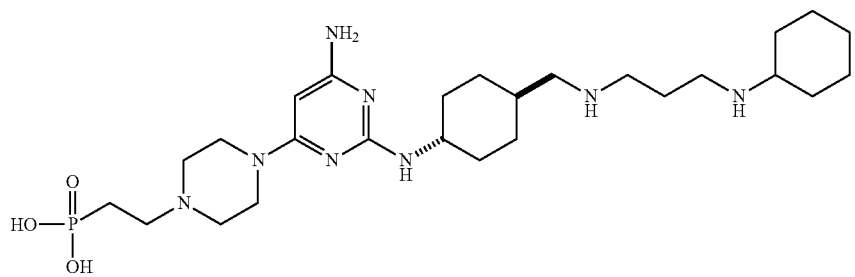
Compound 52
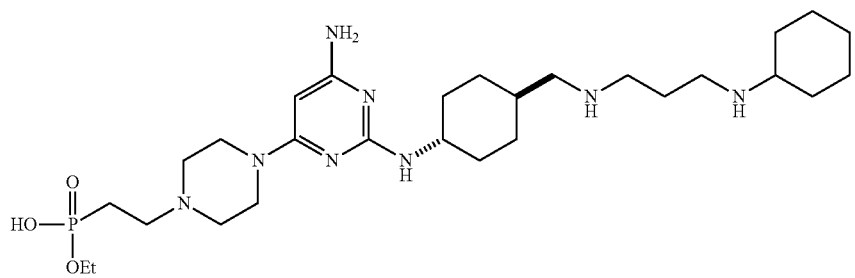
Compound 53
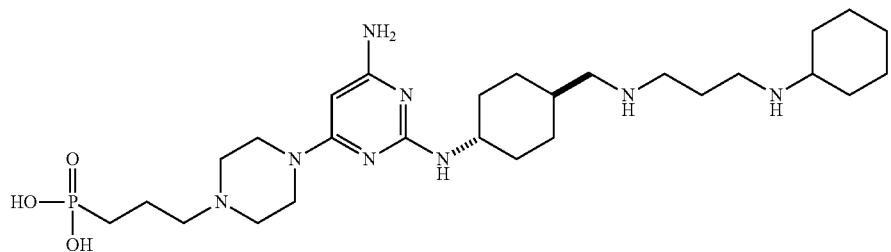

-continued
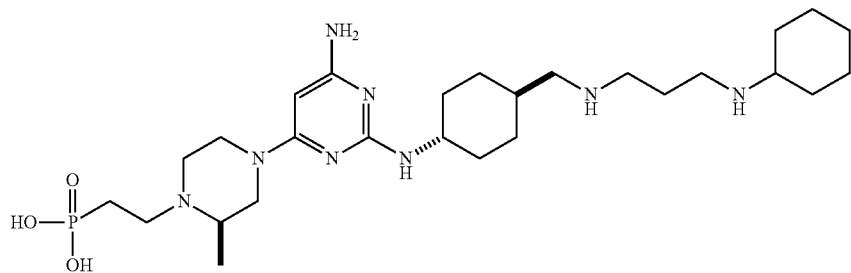
Compound 54
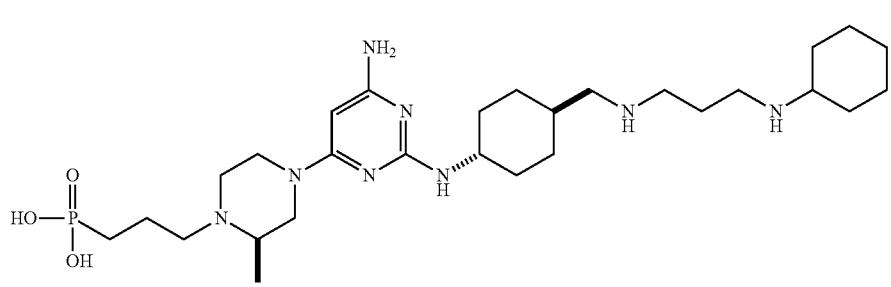
Compound 55
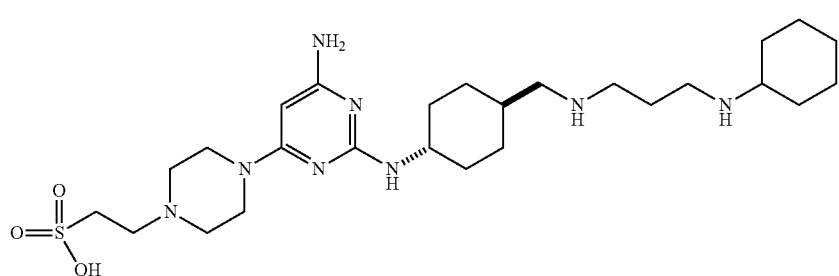
Compound 56
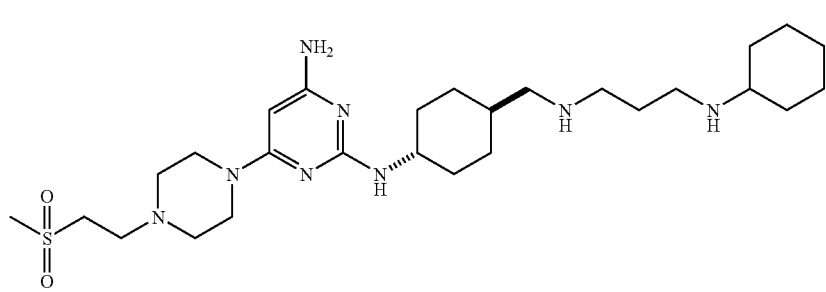
Compound 57
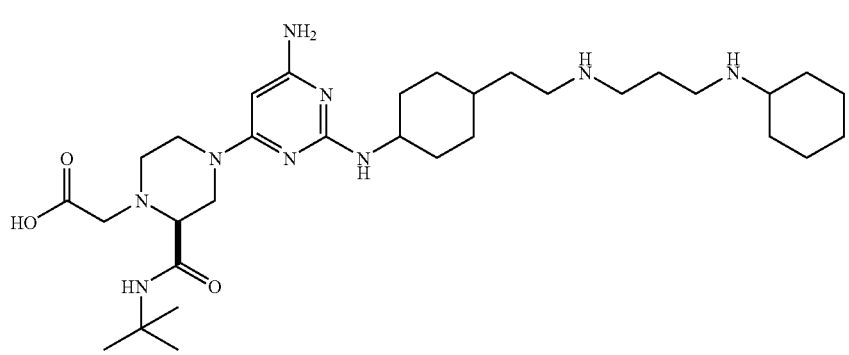
Compound 58

-continued
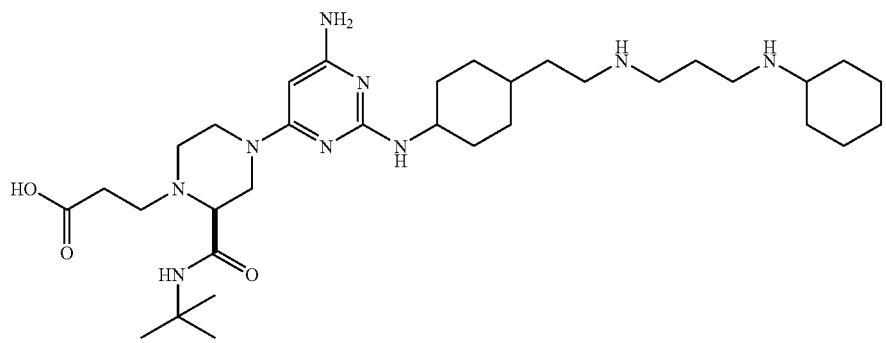
Compound 59
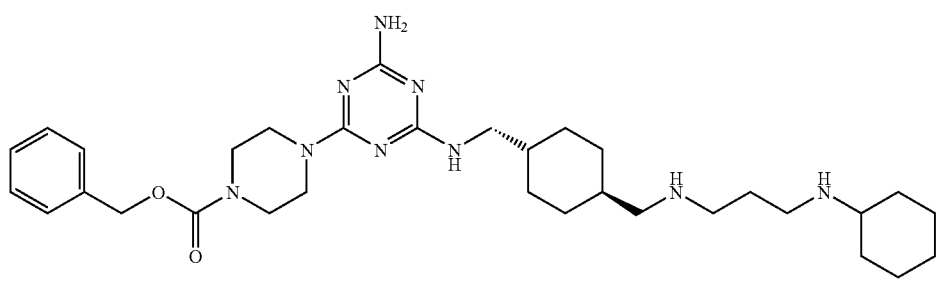
Compound 60
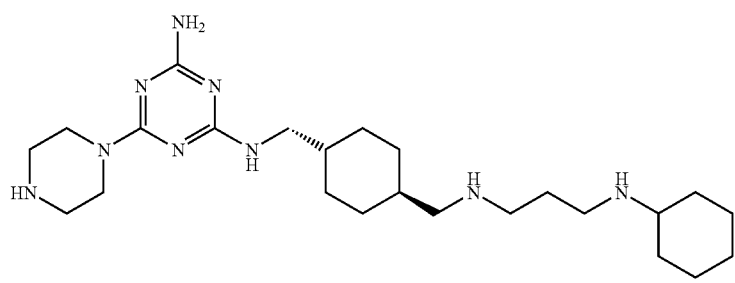
Compound 61
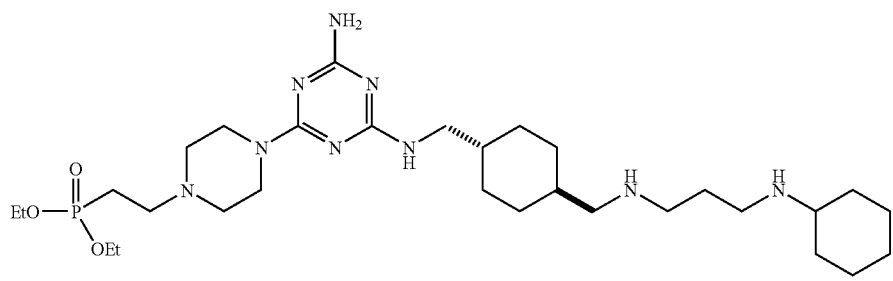
Compound 62
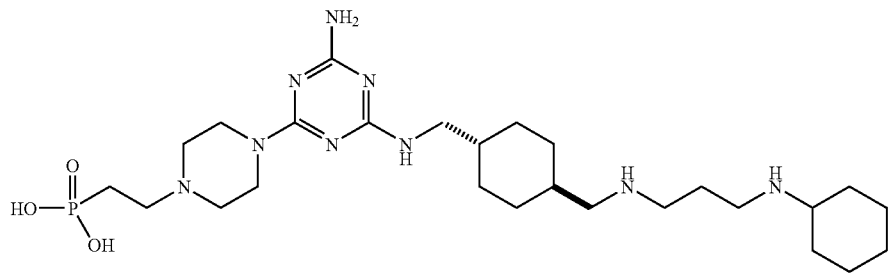
Compound 63

-continued
Compound 64
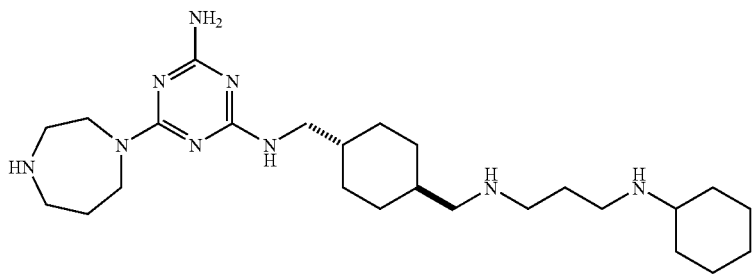
Compound 65
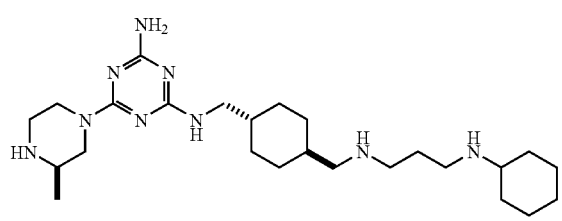
Compound 66
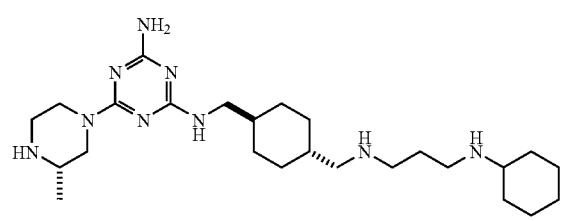
Compound 67
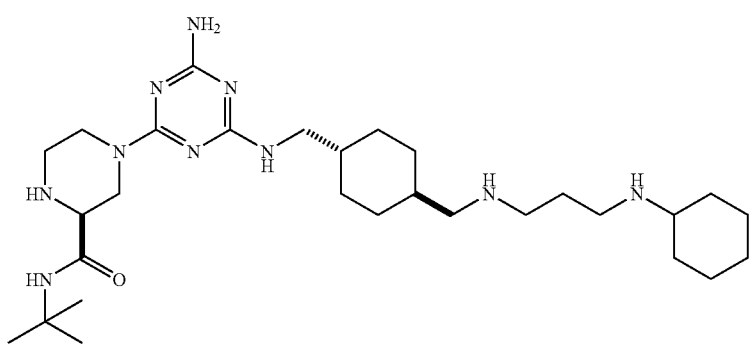
Compound 68
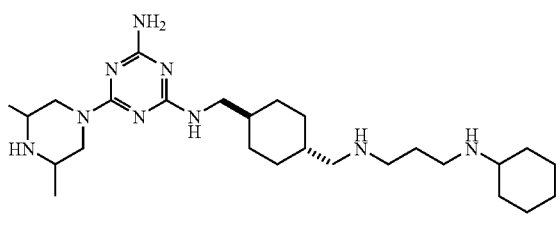
Compound 69
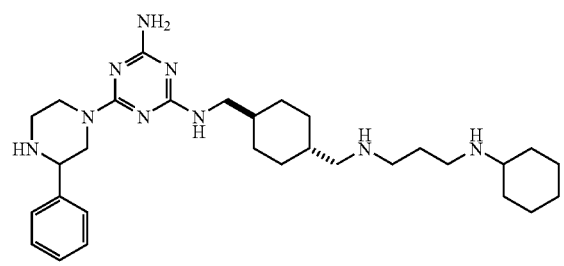
Compound 70
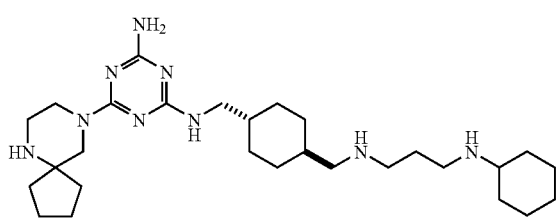
Compound 71
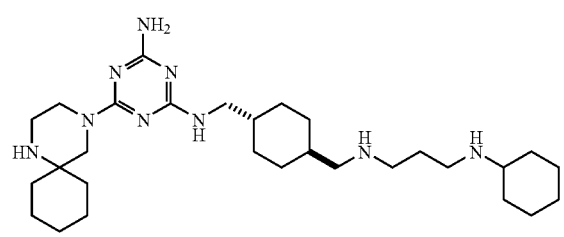

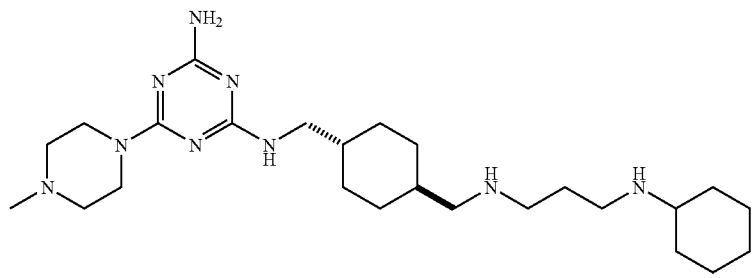
Compound 72
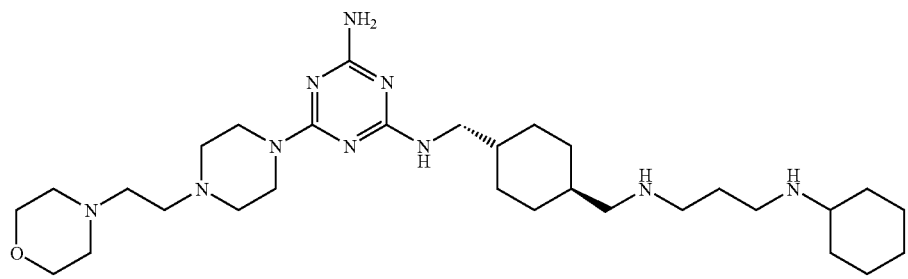
Compound 73
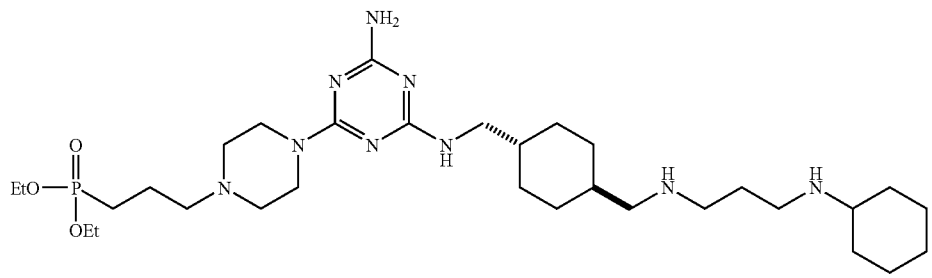
Compound 74
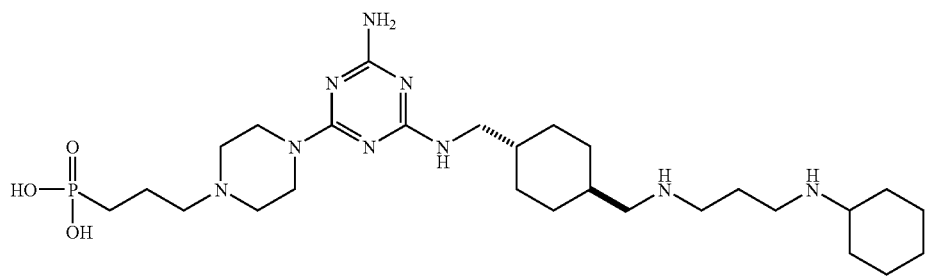
Compound 75
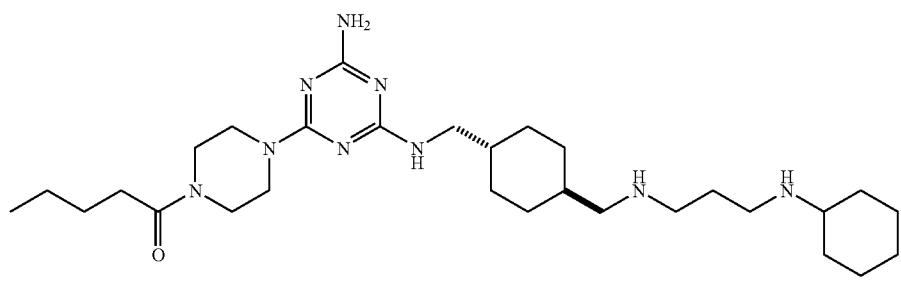
Compound 76

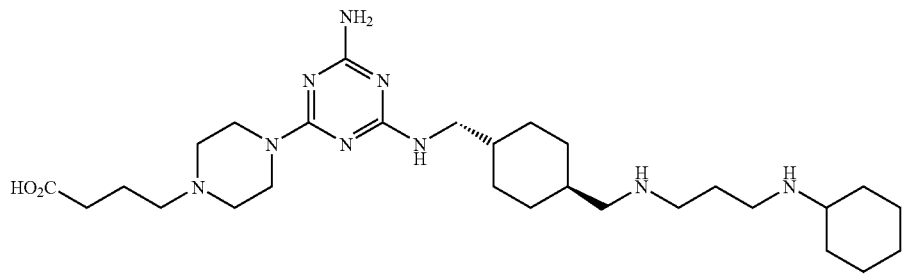
Comopund 77
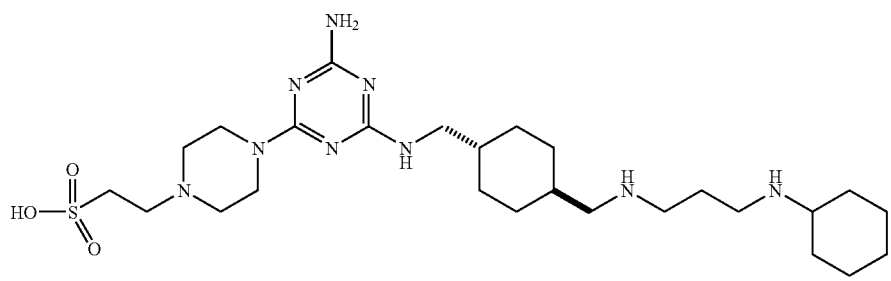
Compound 78
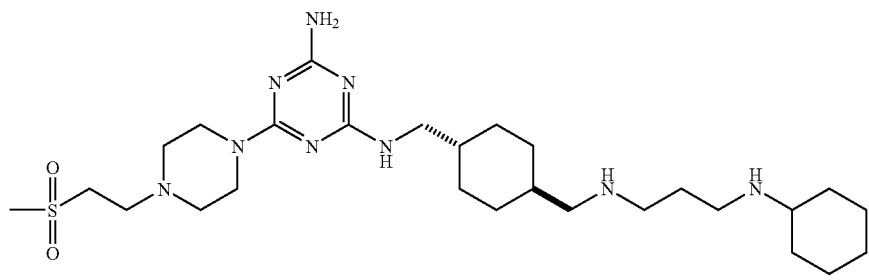
Compound 79
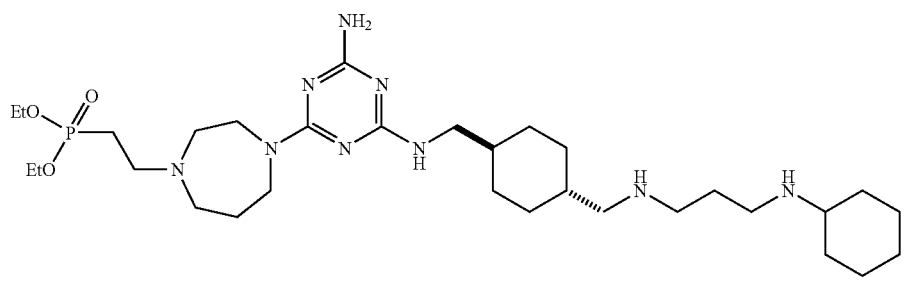
Compound 80
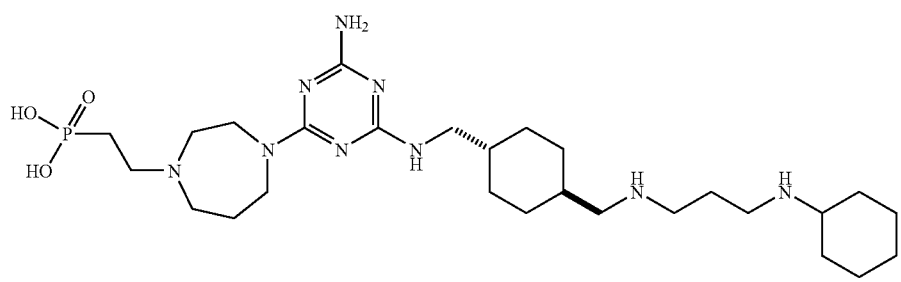
Compound 81

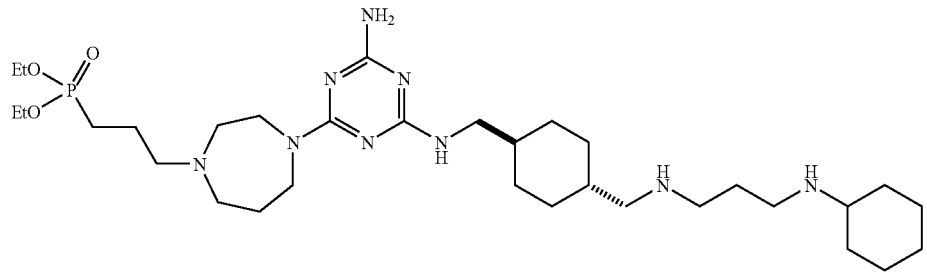
Compound 82
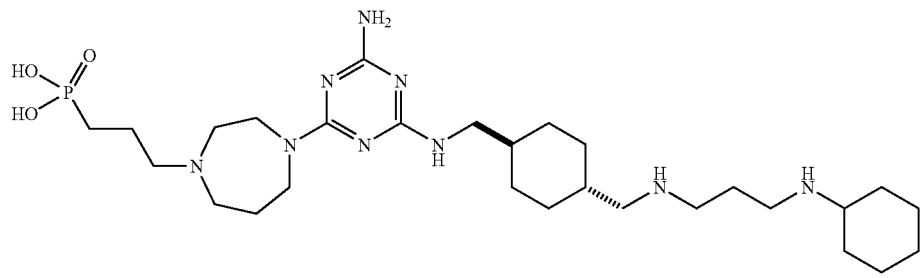
Compound 83
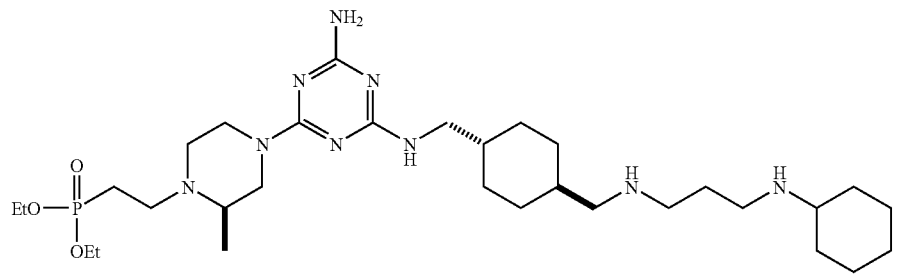
Compound 84
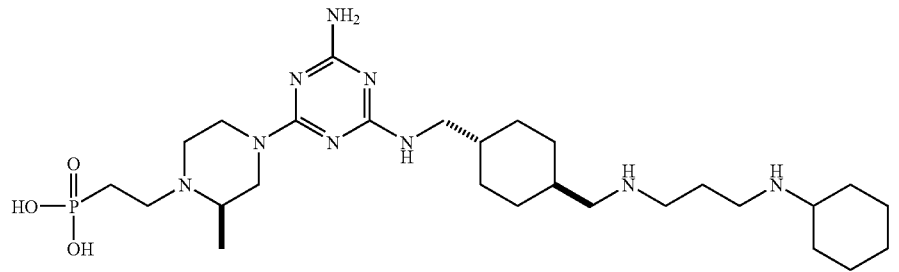
Compound 85
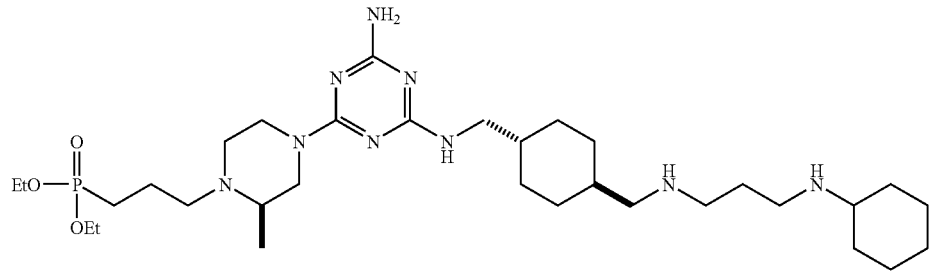
Compound 86

-continued
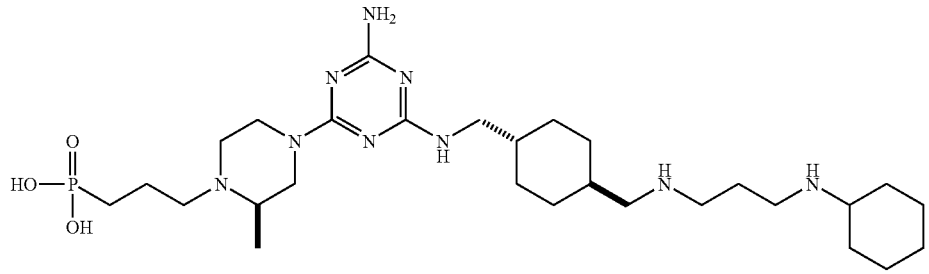
Compound 87
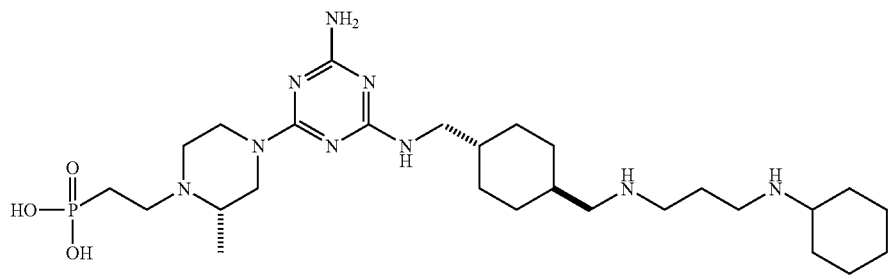
Compound 88
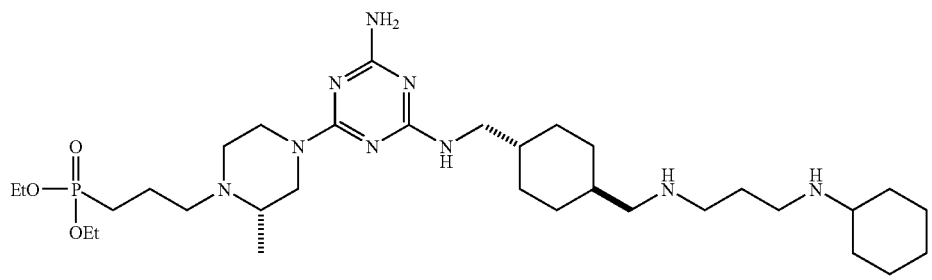
Compound 89
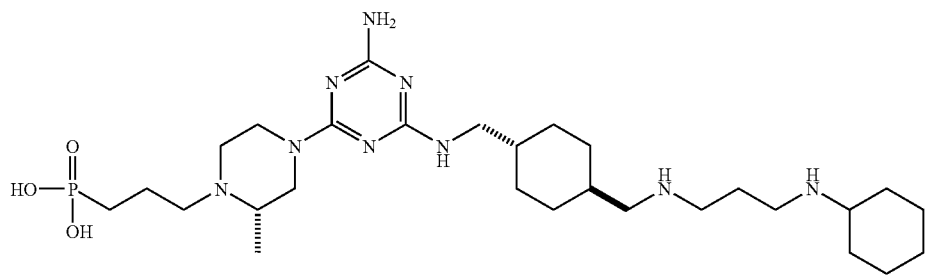
Compound 90
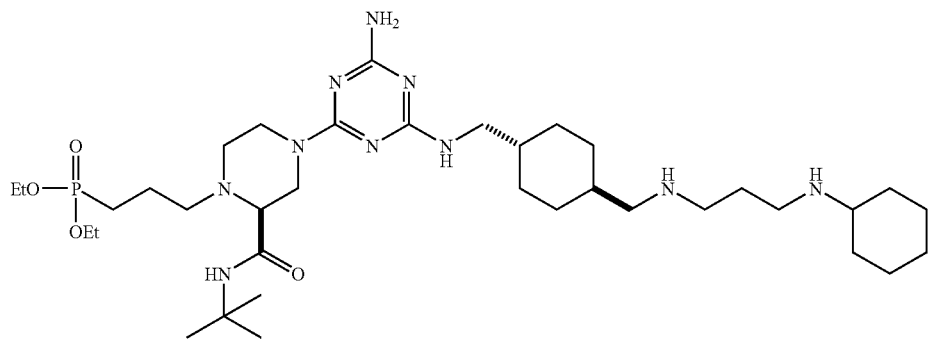
Compound 91

Compound 92
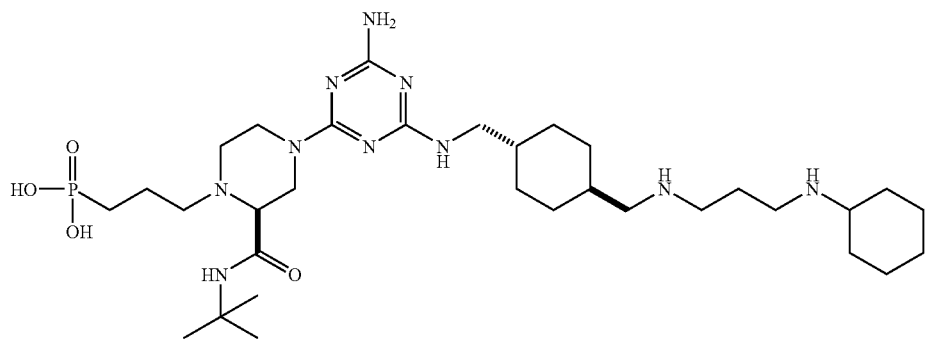
Compound 93
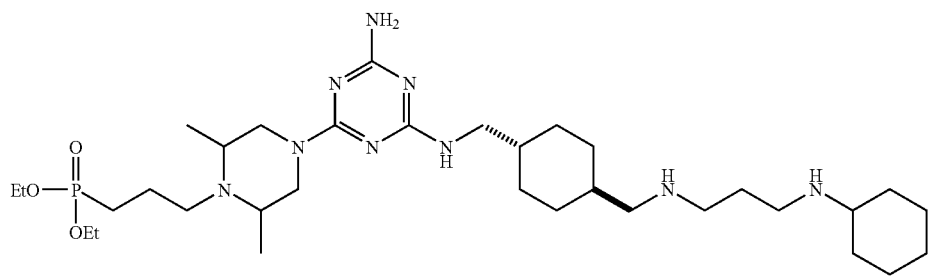
Compound 94
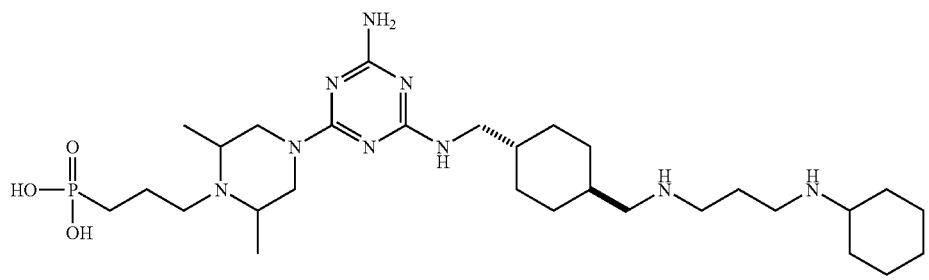
Compound 95
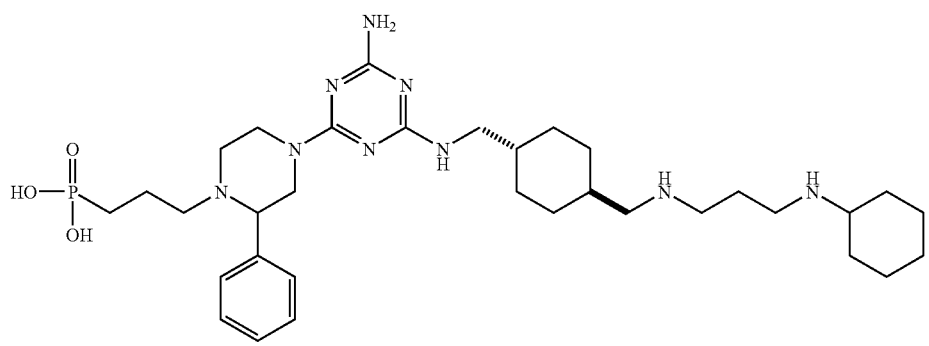
Compound 96
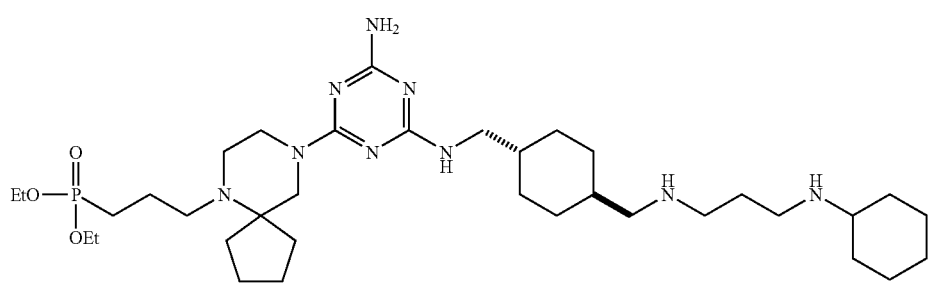

-continued
Compound 97
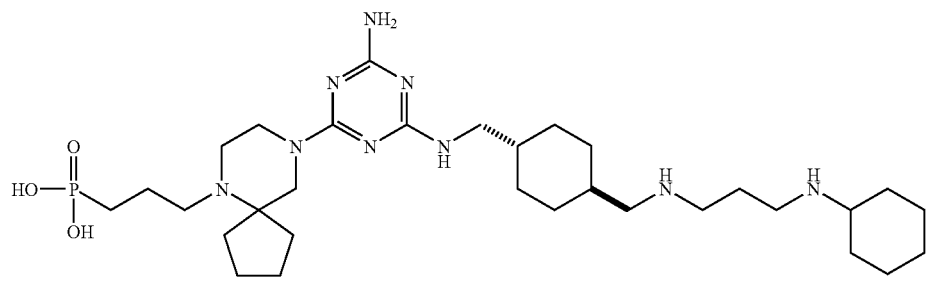
Compound 98
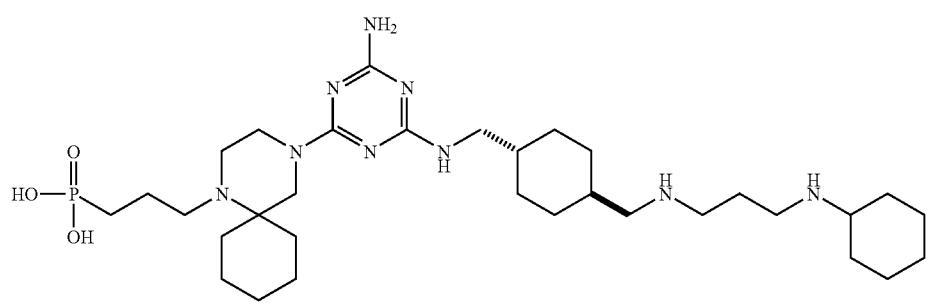
Compound 99 Compound 100
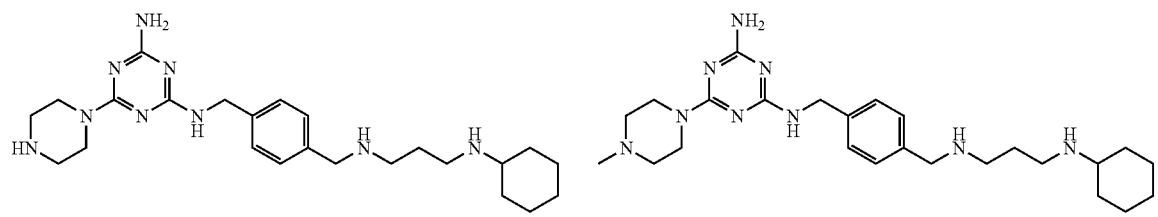
Compound 101
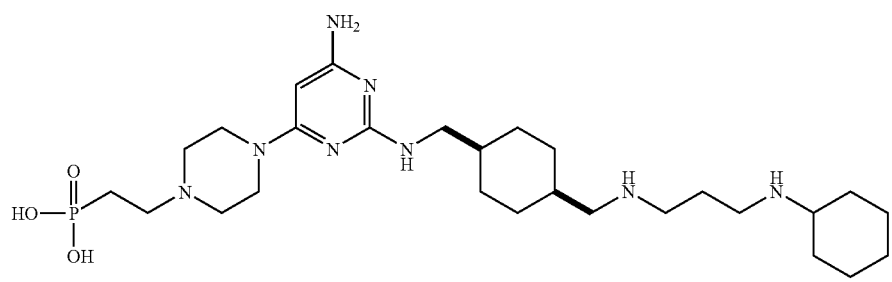
Compound 102
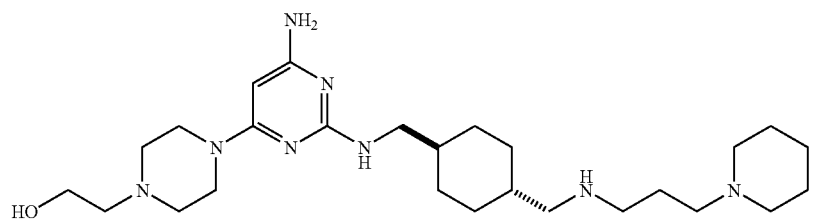
Compound 103
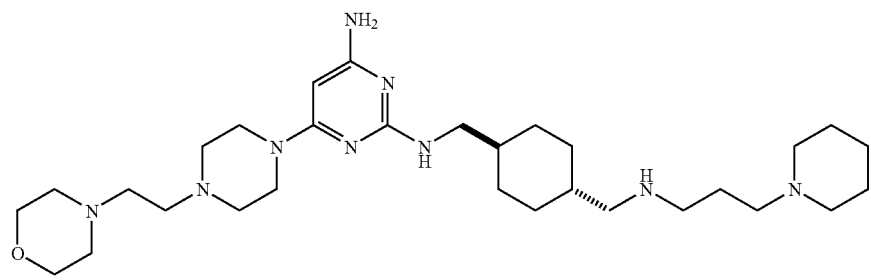

Compound 104
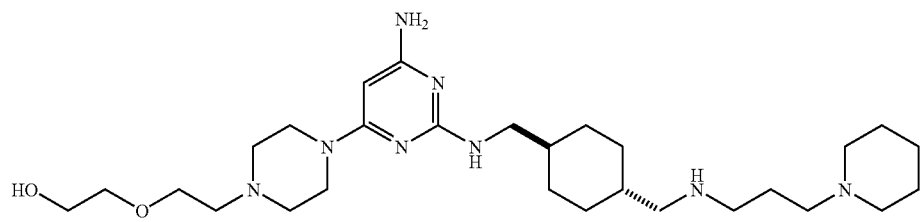
Compound 105
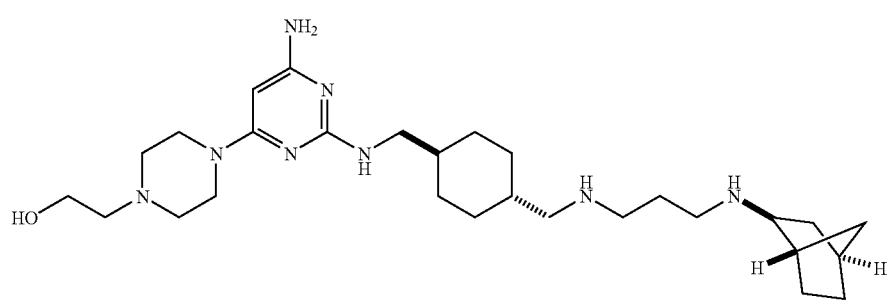
Compound 106
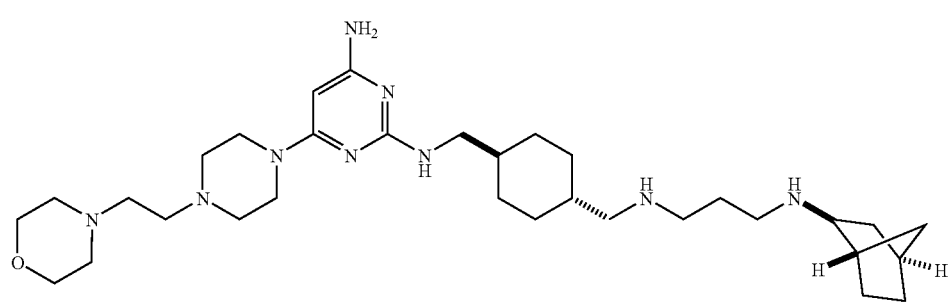
Compound 107
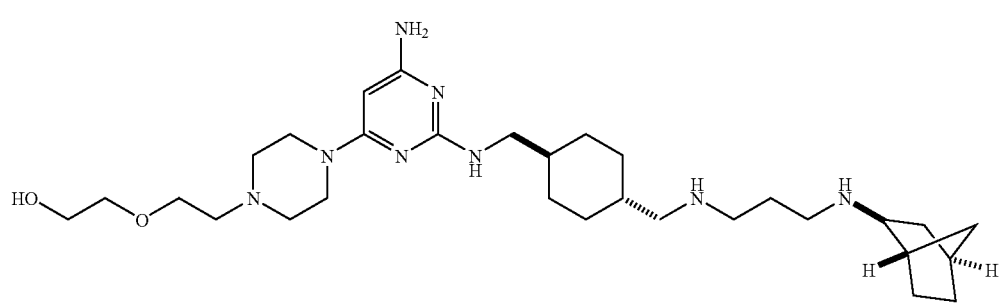
Compound 108
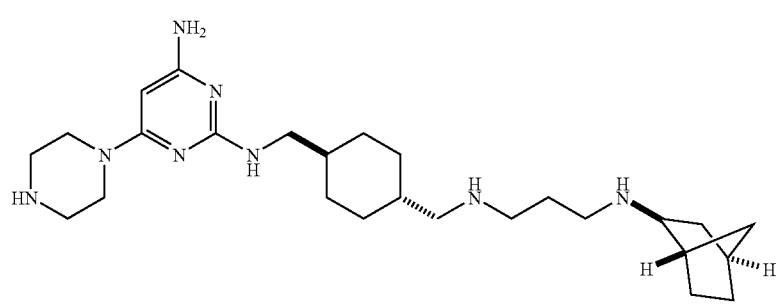

-continued
Compound 109
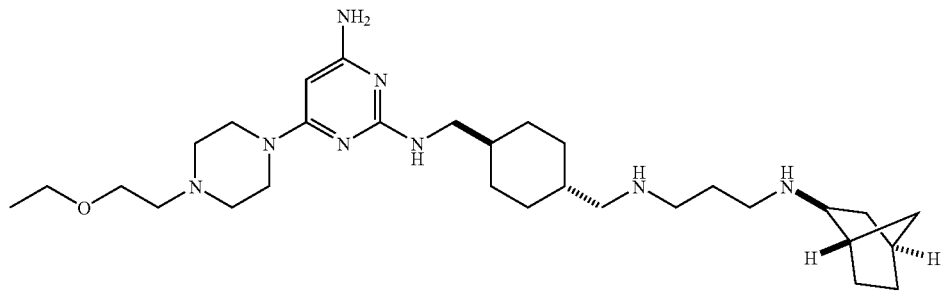
Compound 110
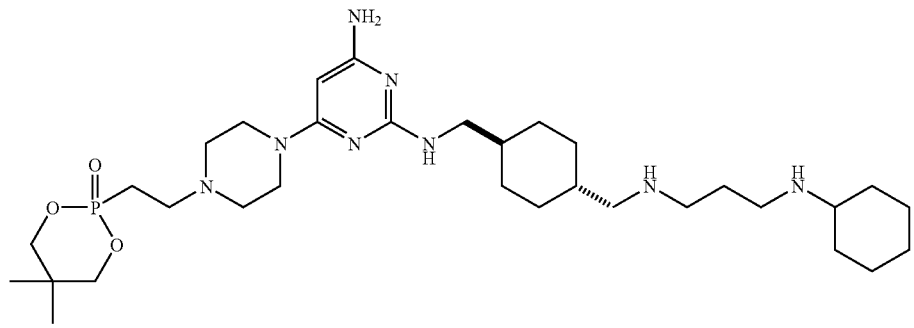
Compound 111
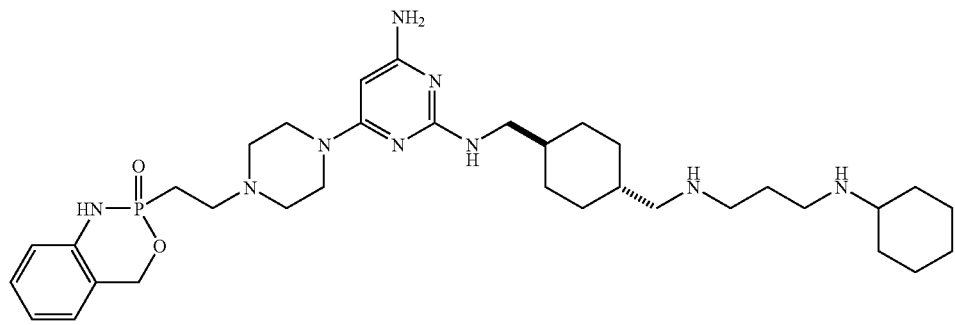
Compound 112
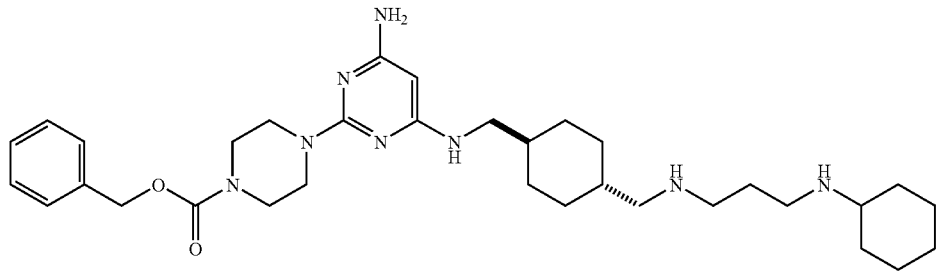
Compound 113
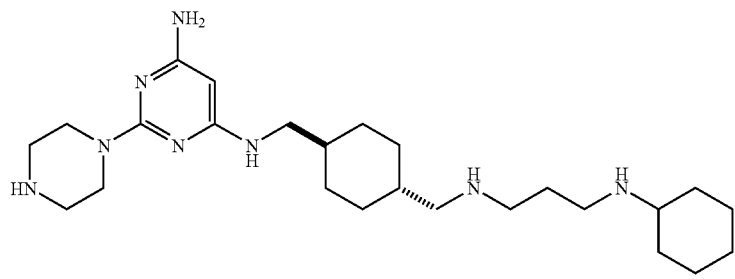

-continued
Compound 114
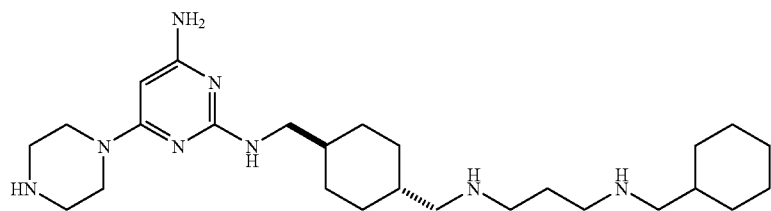
Compound 115
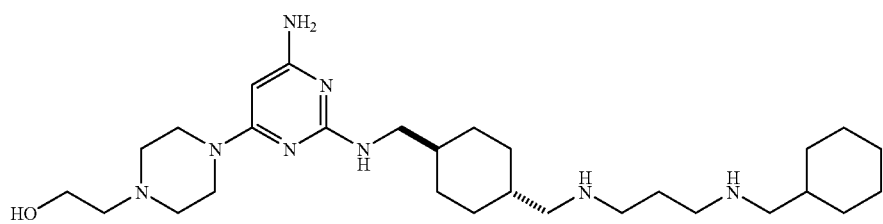
Compound 116
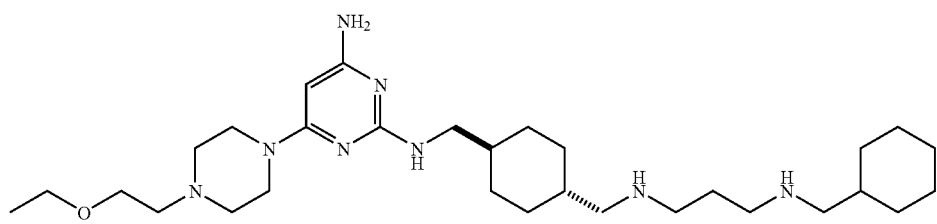
Compound 117
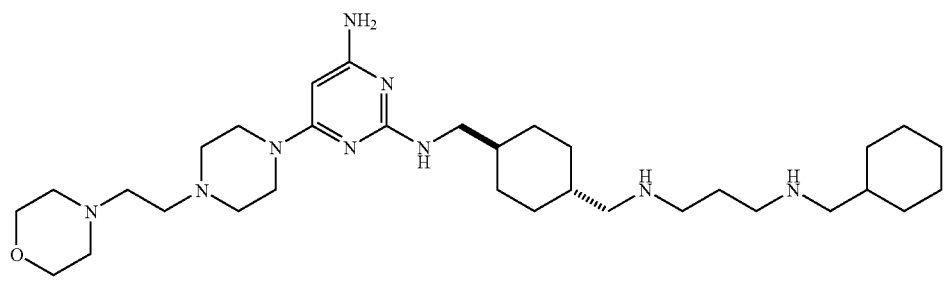
Compound 118
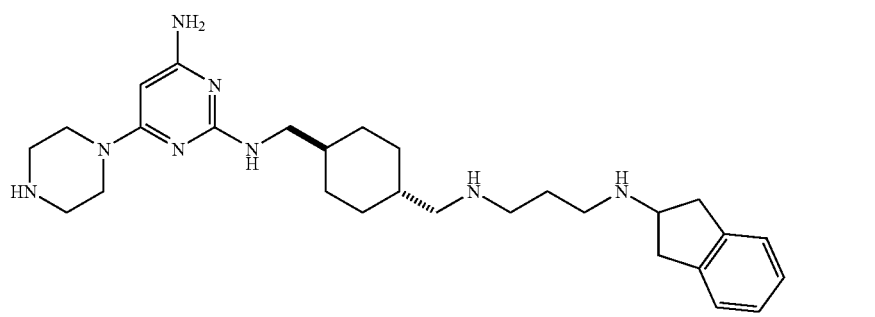
Compound 119
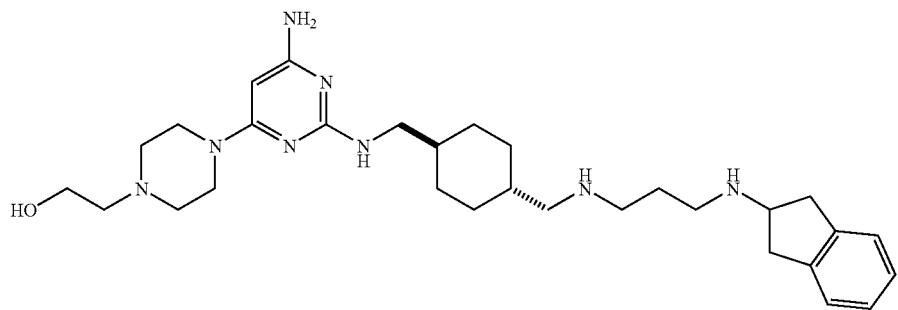

-continued
Compound 120
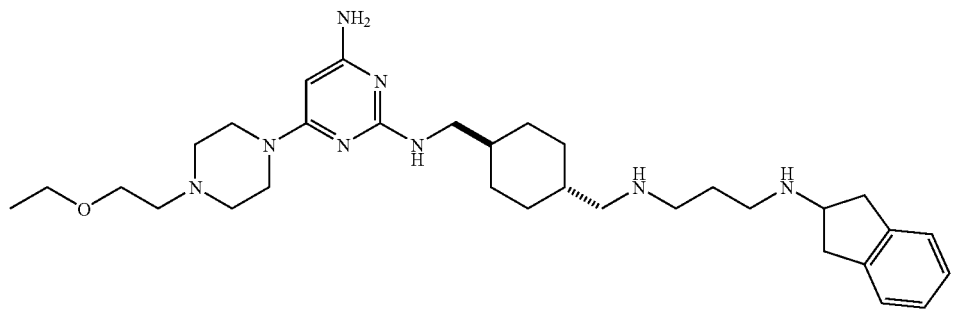
Compound 121
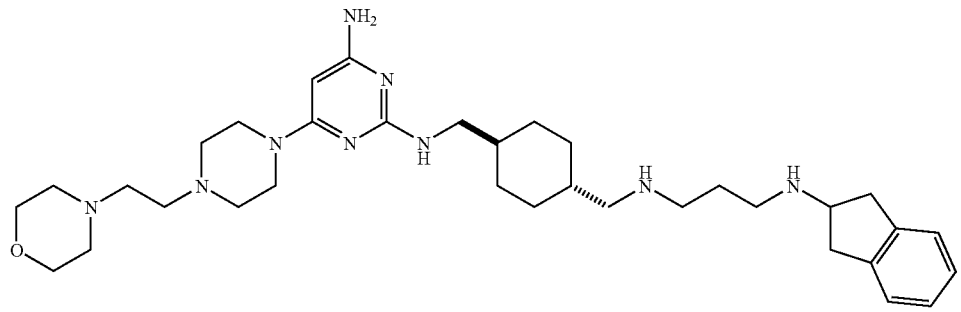
Compound 122
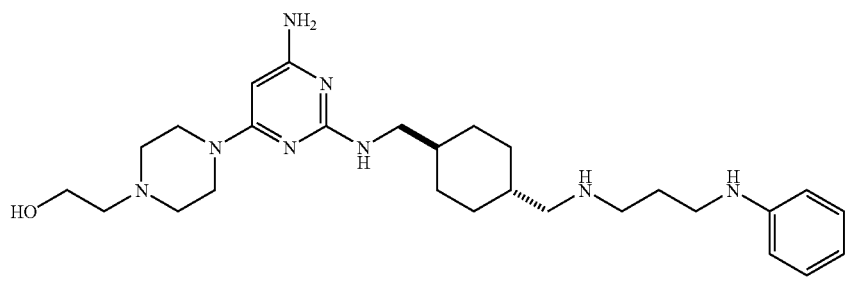
Compound 123
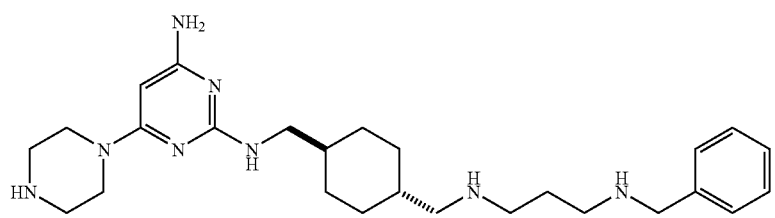
Compound 124
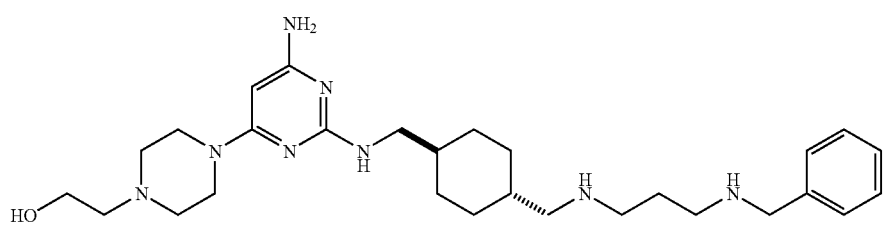
Compound 125
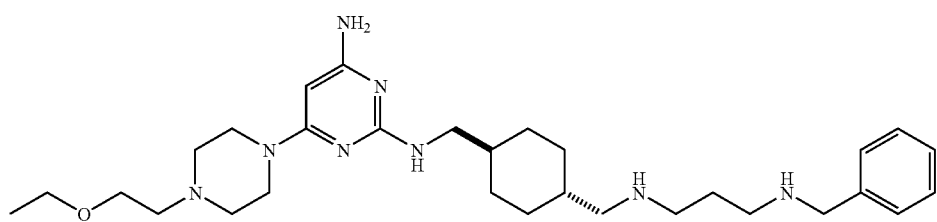

Compound 126
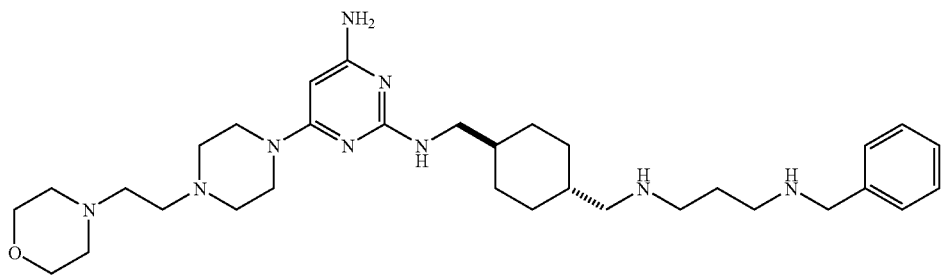
Compound 127
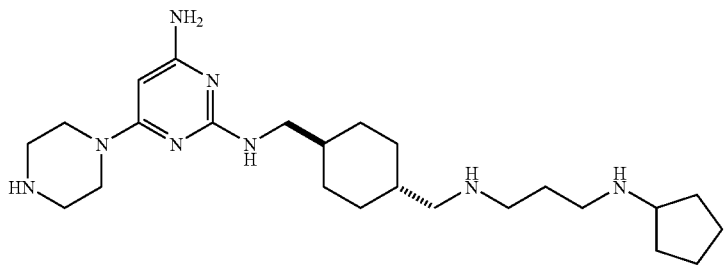
Compound 128
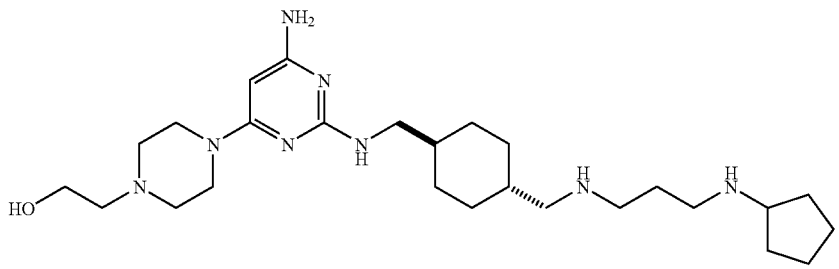
Compound 129
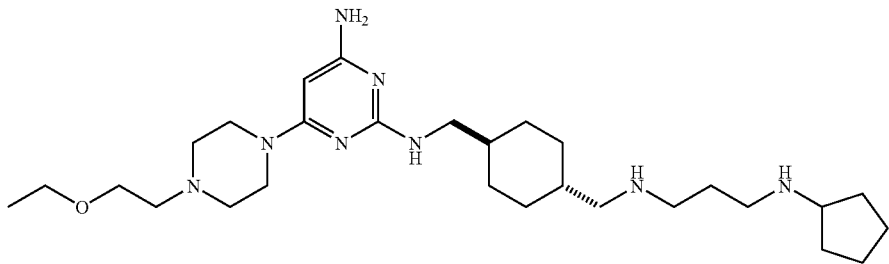
Compound 130
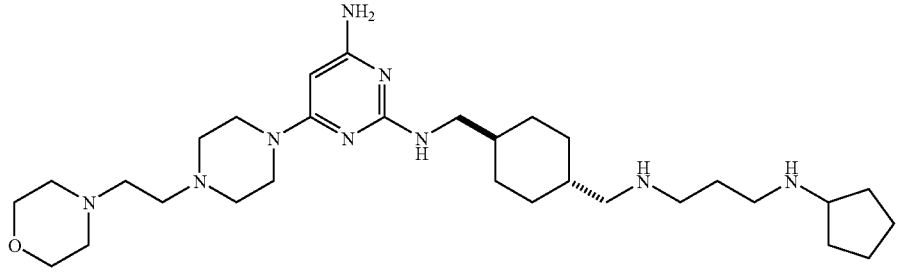
Compound 131
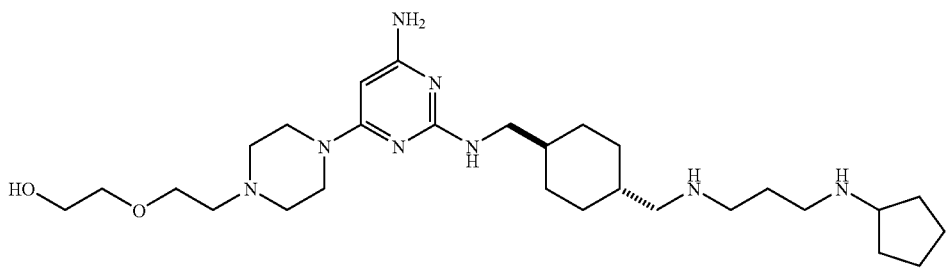

-continued
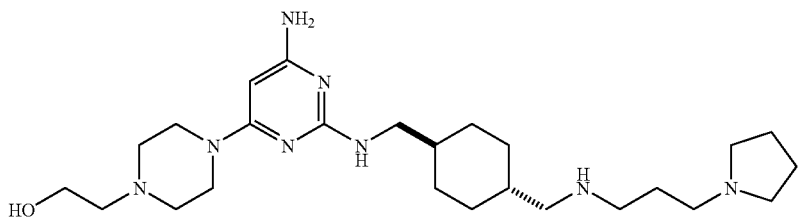
Compound 132
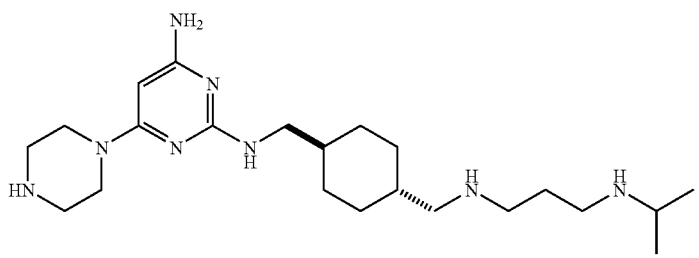
Compound 133
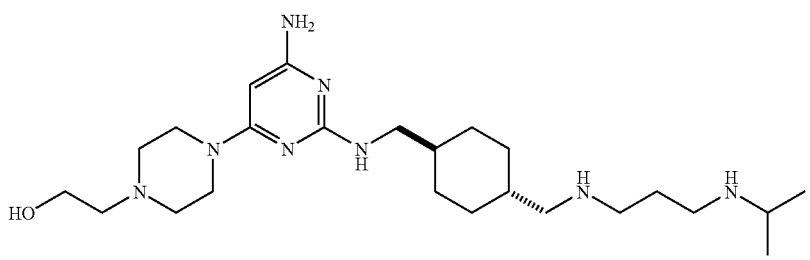
Compound 134
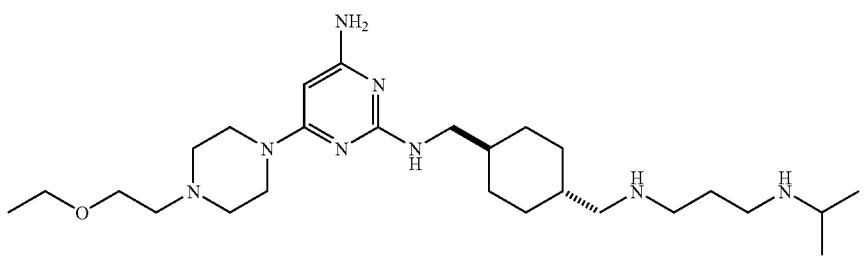
Compound 135
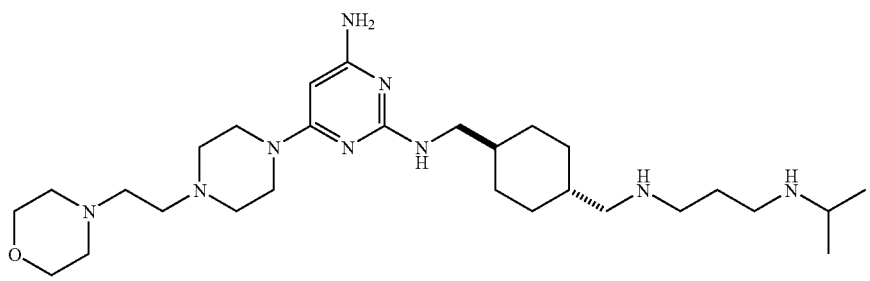
Compound 136
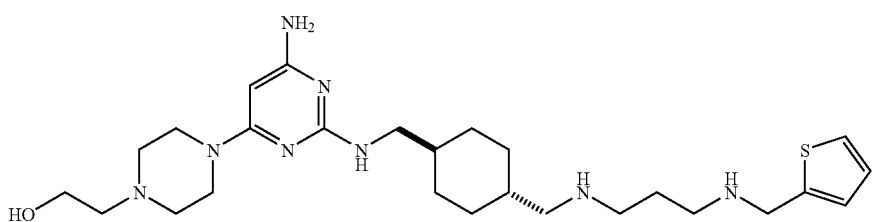
Compound 137

-continued
Compound 138
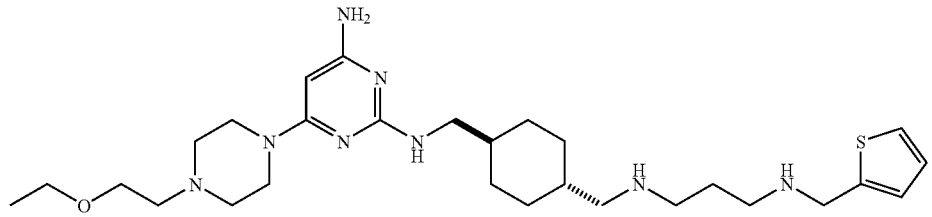
Compound 139
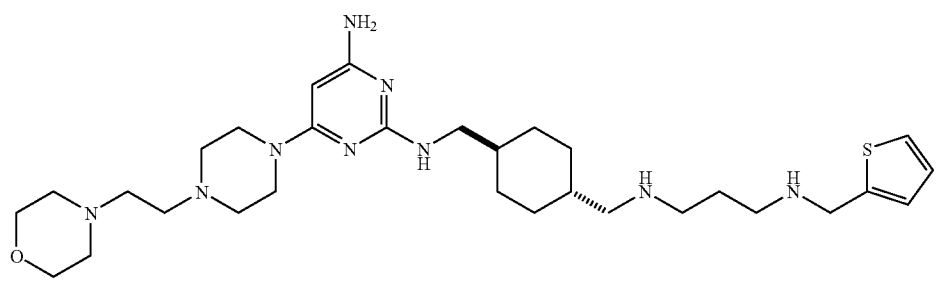
Compound 140
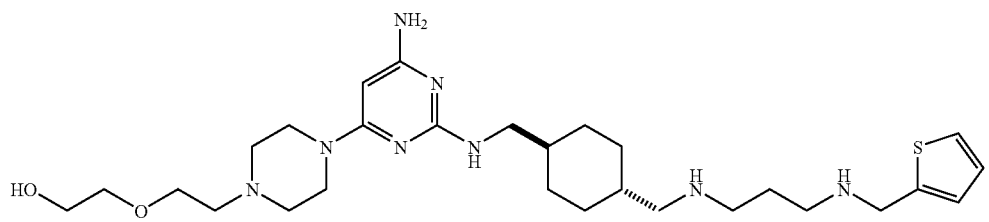
Compound 141
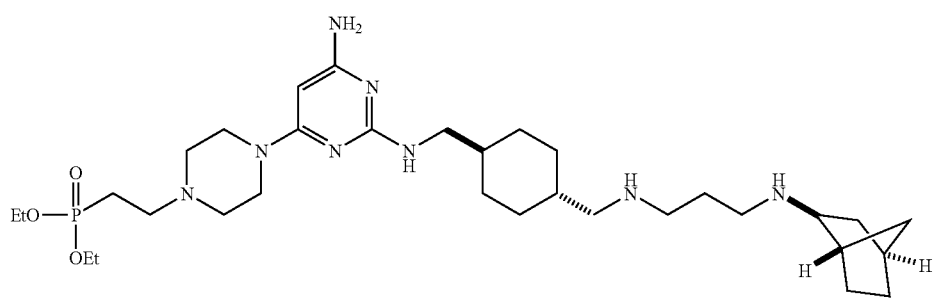
Compound 142
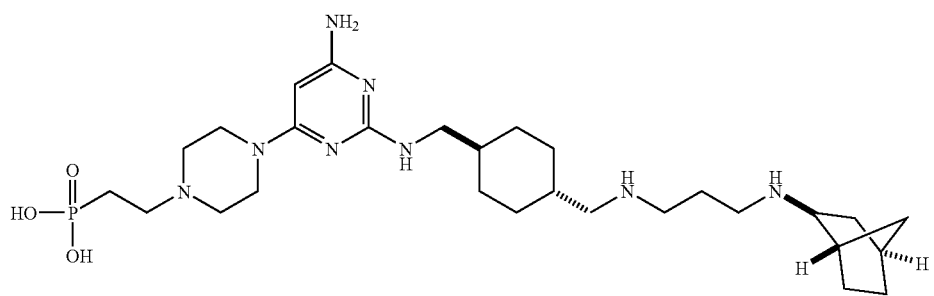
Compound 143
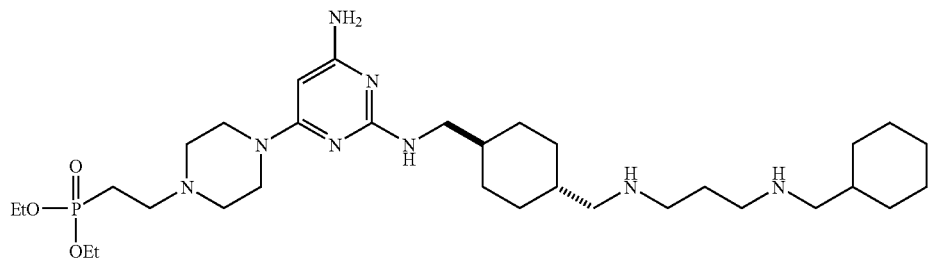

Compound 144
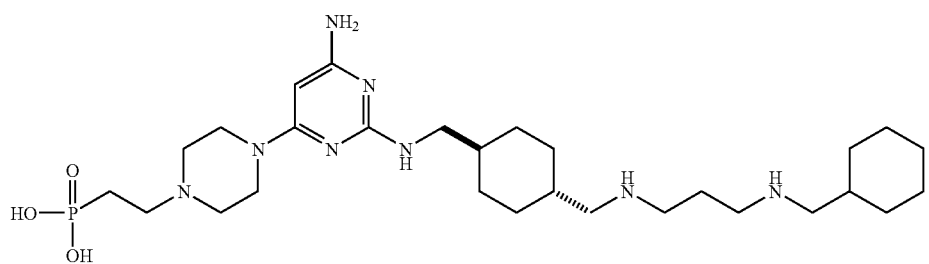
Compound 145
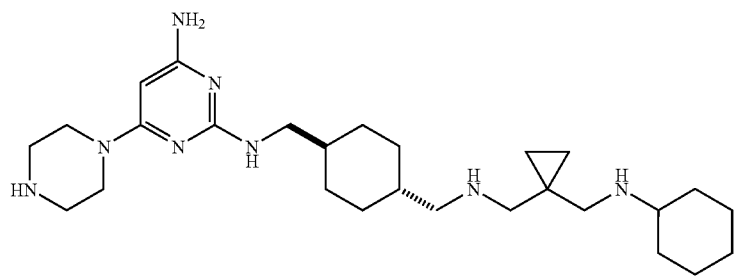
Comopund 146
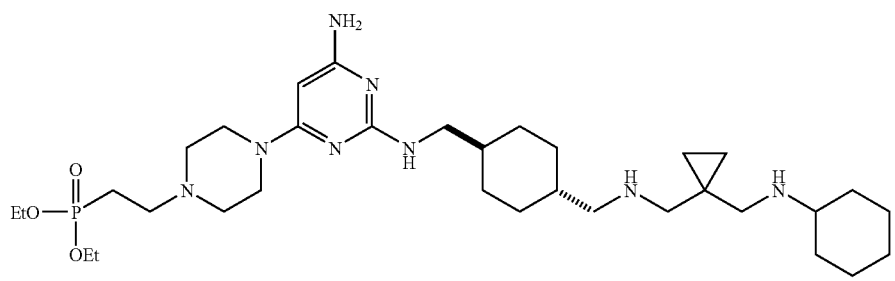
Compound 147
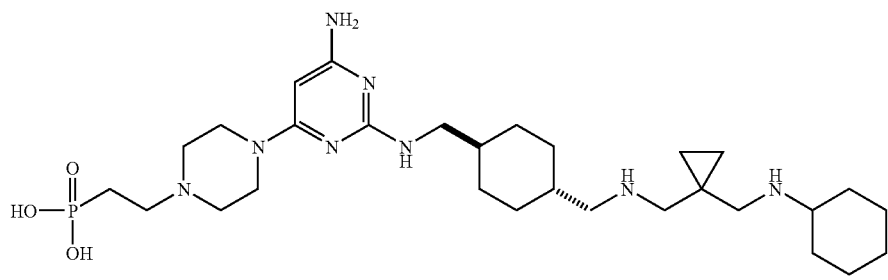
Compound 148
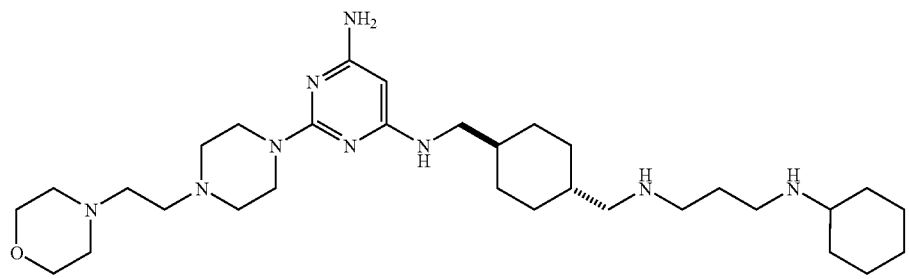
Compound 149
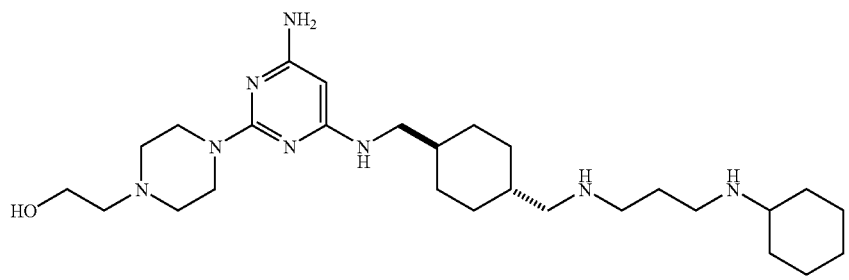

-continued

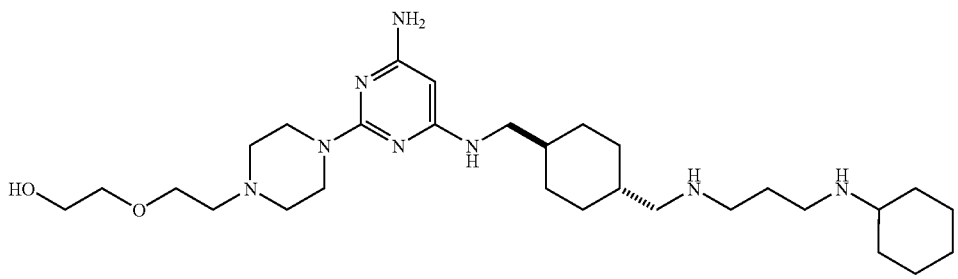

Compound 150

The compounds described above can be prepared by methods well known in the art.

Scheme I below depicts a typical synthetic route for synthesizing certain exemplary compounds. Compound (1) containing two halo groups ($R_3$ and $R_6$ are halo) reacts with an amino compound (2) to give a compound of formula (3), which reacts with piperazine compound (4) containing a nitrogen ring atom to give a compound of formula (5). Finally, deprotection of the resultant compound, if necessary, affords a compound of formula (6), which is one of the compounds of this invention.

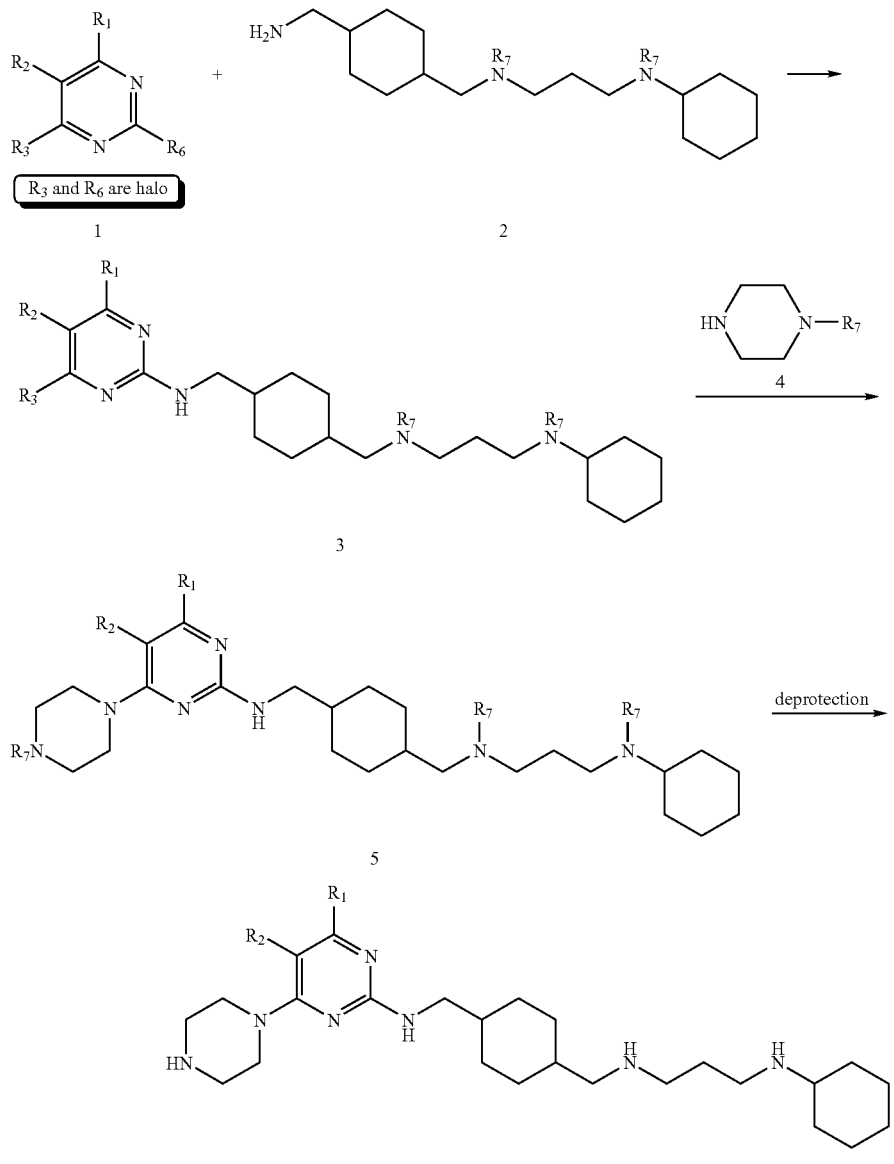

Scheme I can be modified in various manners to prepare other compounds of this invention. For example, an amino compound different from compound (2) may be used, or piperazine compound (4) can be replaced by an imidazolidine or diazepane compound. As another example, compound (6) can be further modified as shown in Scheme II below to obtain phosphonate compound (7) or phophonic acid (8).

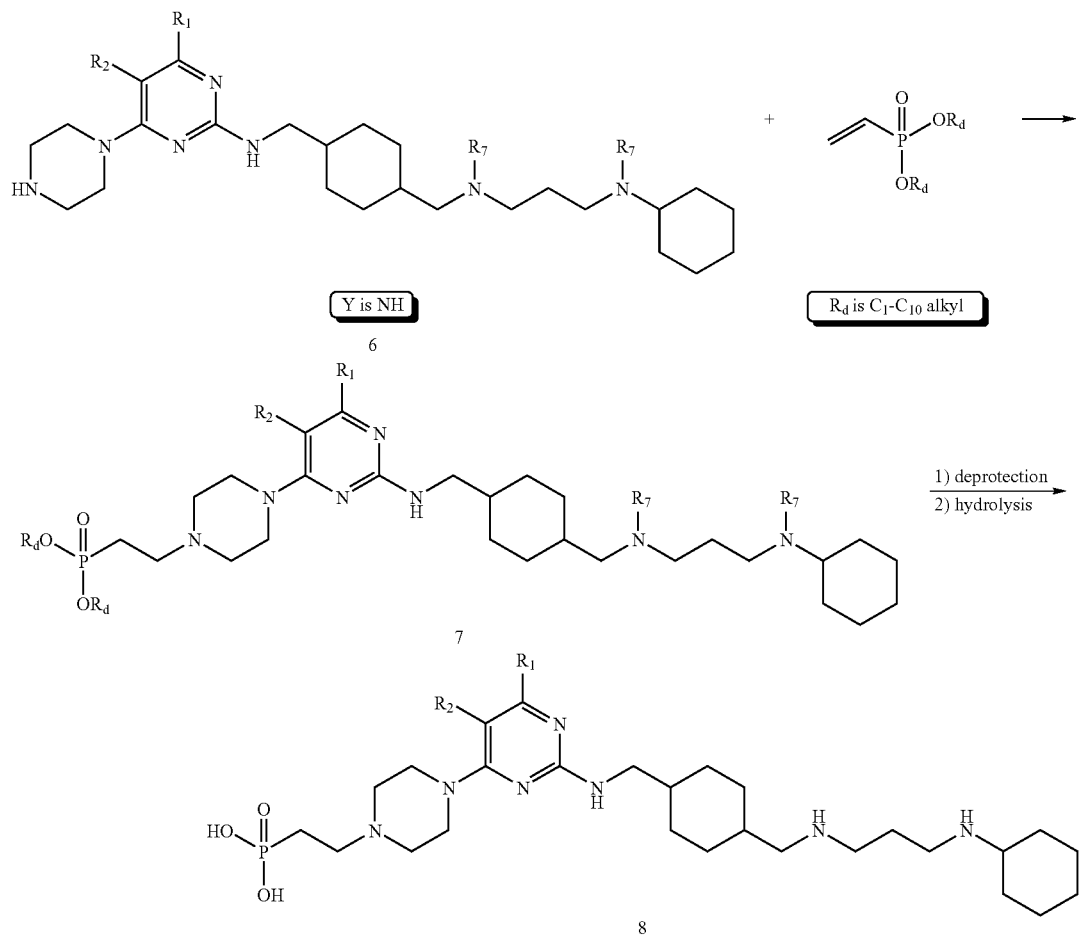

A compound thus synthesized can be purified by a method such as column chromatography, high-pressure liquid chromatography, or recrystallization.

Examples 1-150 below provide detailed descriptions of the preparation of Compounds 1-150 of this invention.

The intermediates used in the methods described above are either commercially available or can be prepared by methods known in the art. The methods may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one compound described above and a pharmaceutical acceptable carrier. Further, this invention covers a method of administering an effective amount of one or more of the compounds of this invention to a patient having a disease described in the summary section above for treating the disease. This invention also covers a method of administering an effective amount of one or more of the compounds to a subject for enhancing migration of bone marrow-derived cells to blood.

The term "treating" or "treatment" refers to administering one or more compounds to a subject, who has an above-described medical condition, a symptom of such a medical condition, or a predisposition toward such a medical condition, with the purpose to confer a therapeutic effect, e.g., to cure, relieve, alter, affect, ameliorate, or prevent the above-described medical condition, the symptom of it, or the predisposition toward it. "An effective amount" refers to the amount of an active compound that is required to confer the therapeutic effect. Effective doses will vary, as recognized by those skilled in the art, depending on the types of diseases treated, route of administration, excipient usage, and the possibility of co-usage with other therapeutic treatment.

To practice the method of the present invention, a composition having one or more compounds can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrastemal, intrathecal, intralesional, or intracranial injection, as well as any suitable infusion technique. The composition can take the form of solutions, suspensions, emulsion, tablets, pills, capsules, powders, microparticles, or nanoparticles. It can be also formulated to achieve controlled-release or sustained-release of the active ingredients.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

An eye drop or ointment composition can also be prepared and used according to the well-known art.

A composition having one or more active compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The compounds described above can be preliminarily screened for their efficacy in treating above-described diseases by an in vitro assay (See Examples 269 and 270 below) and then confirmed by animal experiments and clinic trials. Other methods will also be apparent to those of ordinary skill in the art.

It has been found that the compounds of this invention, acting as the antagonists of CXCR4, compete against its ligand SDF-1 for binding to the receptor and thus block CXCR4/SDF-1 signaling, which is important in the mobilization/homing of stem and progenitor cells. Without being bound by theory, the compounds of this invention may act through the following mechanisms in treating and repairing tissue damage.

By blocking CXCR4/SDF-1 signaling, the compounds of this invention promote the mobilization of stem and progenitor cells from bone morrow, a reservoir of stem/progenitor cells, to the peripheral blood. More specifically, as SDF-1 is highly expressed in bone marrow, stem and progenitor cells, expressing CXCR4, are trapped in bone morrow via CXCR4-SDF-1 interaction. By blocking this interaction, the compounds of this invention release stem and progenitor cells from bone marrow to the peripheral blood. While circulating in the blood, stem and progenitor cells home to tissues and organs where damage has occurred and repair the damage by differentiating into the type of cells, the loss of which has caused the damage.

In the condition of retinopathy, SDF-1 is highly expressed in vitreous. Binding to CXCR4 expressed in stem and progenitor cells, SDF-1 facilitates these cells to migrate to the retina, resulting in neovascularization, which plays an essential role in retinopathy development and progression. Also by blocking CXCR4/SDF-1 signaling, the compounds of this invention prevent stem and progenitor cells homing to the retina, thus effectively treating retinopathy. The compounds can be applied topically to an eye of a retinopathy patient. Unlike systemic applications, topical application does not mobilize stem/progenitor cells out of bone marrow and therefore does not help the homing of these cells into retina.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of Compounds 1

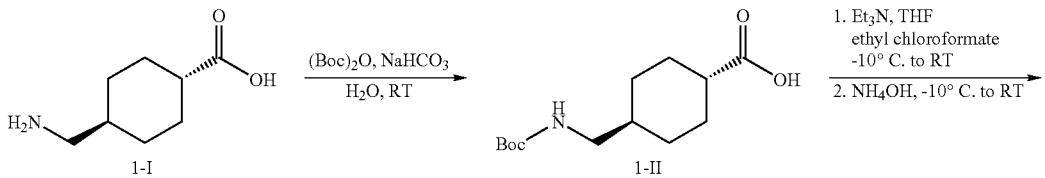

-continued
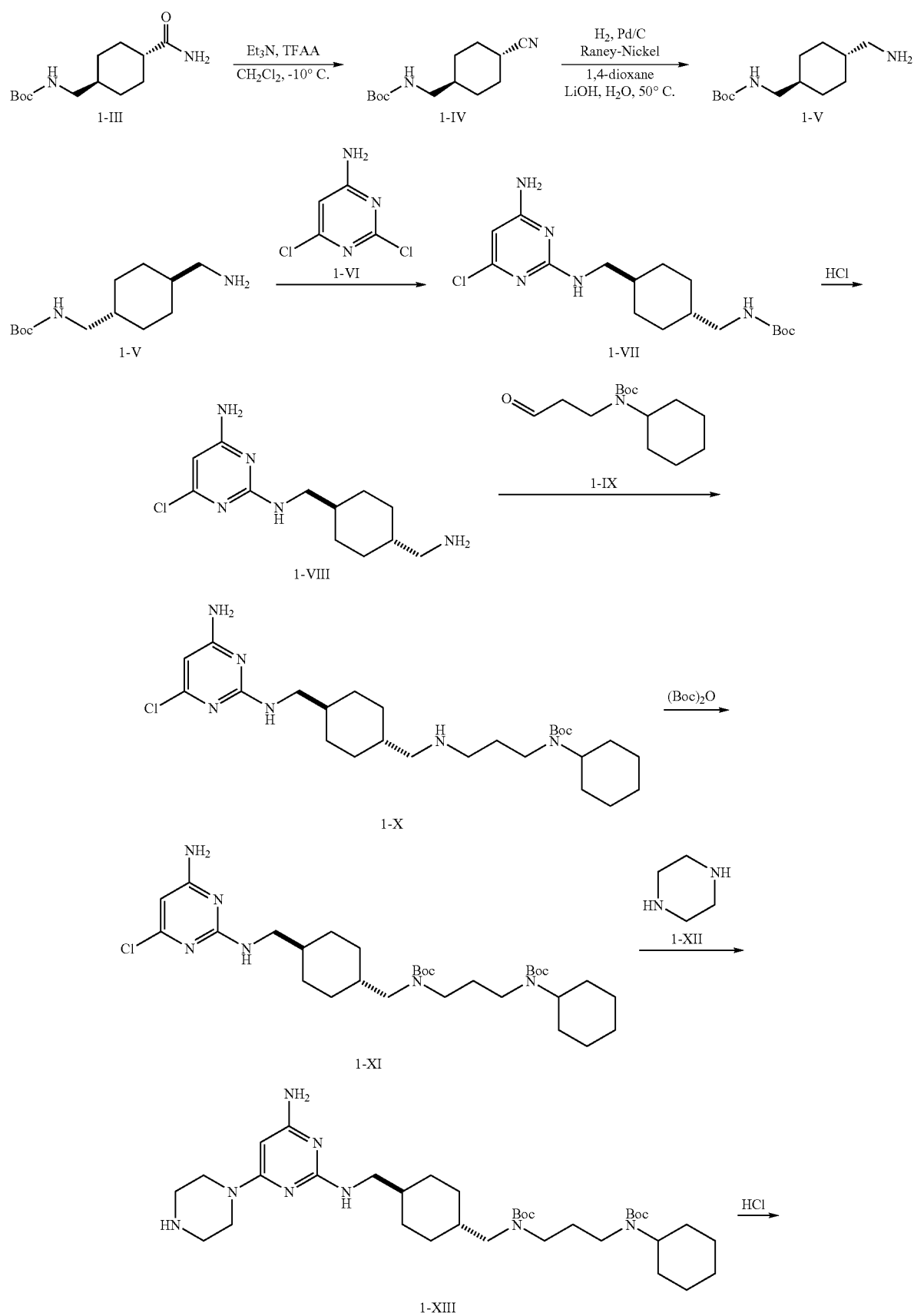

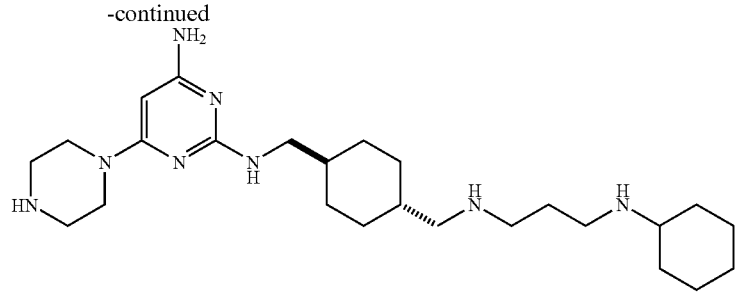

Compound 1

Water (10.0 L) and (Boc)₂O (3.33 kgg, 15.3 mol) were added to a solution of trans-4-aminomethyl-cyclohexanecarboxylic acid (compound 1-I, 2.0 kg, 12.7 mol) and sodium bicarbonate (2.67 kg, 31.8 mol). The reaction mixture was stirred at ambient temperature for 18 hours. The aqueous layer was acidified with concentrated hydrochloric acid (2.95 L, pH=2) and then filtered. The resultant solid was collected, washed three times with water (15 L), and dried in a hot box (60° C.) to give trans-4-(tert-butoxycarbonylamino-methyl)-cyclo-hexanecarboxylic acid (Compound 1-II, 3.17 kg, 97%) as a white solid. $R_f$=0.58 (EtOAc). LC-MS m/e 280 (M+Na⁺). ¹H NMR (300 MHz, CDCl₃) δ 4.58 (brs, 1H), 2.98 (t, J=6.3 Hz, 2H), 2.25 (td, J=12, 3.3 Hz, 1H), 2.04 (d, J=11.1 Hz, 2H), 1.83 (d, J=11.1 Hz, 2H), 1.44 (s, 9H), 1.35~1.50 (m, 3H), 0.89~1.03 (m, 2H). ¹³C NMR (75 MHz, CDCl₃) δ 181.31, 156.08, 79.12, 46.41, 42.99, 37.57, 29.47, 28.29, 27.96. M.p. 134.8~135.0° C.

A suspension of compound 1-II (1.0 kg, 3.89 mol) in THF (5 L) was cooled at −10° C. and triethyl amine (1.076 L, 7.78 mol) and ethyl chloroformate (0.441 L, 4.47 mol) were added below −10° C. The reaction mixture was stirred at ambient temperature for 3 hours. The reaction mixture was then cooled at −10° C. again and NH₄OH (3.6 L, 23.34 mol) was added below −10° C. The reaction mixture was stirred at ambient temperature for 18 hours and filtered. The solid was collected and washed three times with water (10 L) and dried in a hot box (60° C.) to give trans-4-(tert-butoxycarbonyl-amino-methyl)-cyclohexanecarboxylic acid amide (Compound 1-III, 0.8 kg, 80%) as a white solid. $R_f$=0.23 (EtOAc). LC-MS m/e 279, M+Na⁺. ¹H NMR (300 MHz, CD₃OD) δ 6.63 (brs, 1H), 2.89 (t, J=6.3 Hz, 2H), 2.16 (td, J=12.2, 3.3 Hz, 1H), 1.80~1.89 (m, 4H), 1.43 (s, 9H), 1.37~1.51 (m, 3H), 0.90~1.05 (m, 2H), ¹³C NMR (75 MHz, CD₃OD) δ 182.26, 158.85, 79.97, 47.65, 46.02, 39.28, 31.11, 30.41, 28.93. M.p. 221.6~222.0° C.

A suspension of compound 1-III (1.2 kg, 4.68 mol) in CH₂Cl₂ (8 L) was cooled at −10° C. and triethyl amine (1.3 L, 9.36 mol) and trifluoroacetic anhydride (0.717 L, 5.16 mol) were added below −10° C. The reaction mixture was stirred for 3 hours. After water (2.0 L) was added, the organic layer was separated and washed with water (3.0 L) twice. The organic layer was then passed through silica gel and concentrated. The resultant oil was crystallized by methylene chloride. The crystals were washed with hexane to give trans-(4-cyano-cyclohexylmethyl)-carbamic acid tert-butyl ester (Compound 1-IV, 0.95 kg, 85%) as a white crystal. $R_f$=0.78 (EtOAc). LC-MS m/e 261, M+Na⁺. ¹H NMR (300 MHz, CDCl₃) δ 4.58 (brs, 1H), 2.96 (t, J=6.3 Hz, 2H), 2.36 (td, J=12, 3.3 Hz, 1H), 2.12 (dd, J=13.3, 3.3 Hz, 2H), 1.83 (dd, J=13.8, 2.7 Hz, 2H), 1.42 (s, 9H), 1.47~1.63 (m, 3H), 0.88~1.02 (m, 2H). ¹³C NMR (75 MHz, CDCl₃) δ 155.96, 122.41, 79.09, 45.89, 36.92, 29.06, 28.80, 28.25, 28.00. M.p. 100.4~100.6° C.

Compound 1-IV (1.0 kg, 4.196 mol) was dissolved in a mixture of 1,4-dioxane (8.0 L) and water (2.0 L). To the reaction mixture were added lithium hydroxide monohydrate (0.314 kg, 4.191), Raney-nickel (0.4 kg, 2.334 mol), and 10% palladium on carbon (0.46 kg, 0.216 mol) as a 50% suspension in water. The reaction mixture was stirred under hydrogen atmosphere at 50° C. for 20 hours. After the catalysts were removed by filtration and the solvents were removed in vacuum, a mixture of water (1.0 L) and CH₂Cl₂ (0.3 L) was added. After phase separation, the organic phase was washed with water (1.0 L) and concentrated to give trans-(4-aminomethyl-cyclohexylmethyl)-carbamic acid tert-butyl ester (compound 1-V, 0.97 kg, 95%) as pale yellow thick oil. $R_f$=0.20 (MeOH/EtOAc=9/1). LC-MS m/e 243, M+H⁺. ¹H NMR (300 MHz, CDCl₃) δ 4.67 (brs, 1H), 2.93 (t, J=6.3 Hz, 2H), 2.48 (d, J=6.3 Hz, 2H), 1.73~1.78 (m, 4H), 1.40 (s, 9H), 1.35 (brs, 3H), 1.19~1.21 (m, 1H), 0.77~0.97 (m, 4H). ¹³C NMR (75 MHz, CDCl₃) δ 155.85, 78.33, 48.27, 46.38, 40.80, 38.19, 29.87, 29.76, 28.07.

A solution of compound 1-V (806 g) and Et₃N (1010 g, 3 eq) in 1-pentanol (2.7 L) was treated with compound 1-VI, 540 g, 1 eq) at 90° C. for 15 hours. TLC showed that the reaction was completed.

Ethyl acetate (1.5 L) was added to the reaction mixture at 25° C. The solution was stirred for 1 hour. The Et₃NHCl salt was filtered. The filtrate was then concentrated to 1.5 L (⅙ of original volume) by vacuum at 50° C. Then, diethyl ether (2.5 L) was added to the concentrated solution to afford the desired product 1-VII (841 g, 68% yield) after filtration at 25° C.

A solution of intermediate 1-VII (841 g) was treated with 4 N HCl/dioxane (2.7 L) in MeOH (8.1 L) and stirred at 25° C. for 15 hours. TLC showed that the reaction was completed. The mixture was concentrated to 1.5 L (⅐ of original volume) by vacuum at 50° C. Then, diethyl ether (5 L) was added to the solution slowly, and HCl salt of 1-VIII (774 g) was formed, filtered, and dried under vacuum (<10 torr). For neutralization, K₂CO₃ (2.5 kg, 8 eq) was added to the solution of HCl salt of 1-VIII in MeOH (17 L) at 25° C. The mixture was stirred at the same temperature for 3 hours (pH>12) and filtered (estimated amount of 1-VIII in the filtrate is 504 g).

Aldehyde 1-IX (581 g, 1.0 eq based on mole of 1-VII) was added to the filtrate of 1-VIII at 0-10° C. The reaction was stirred at 0-10° C. for 3 hours. TLC showed that the reaction was completed. Then, NaBH₄ (81 g, 1.0 eq based on mole of 1-VII) was added at less than 10° C. and the solution was stirred at 10-15° C. for 1 h. The solution was concentrated to get a residue, which then treated with CH₂Cl₂ (15 L). The mixture was washed with saturated aq. NH₄Cl solution (300 mL) diluted with H₂O (1.2 L). The CH₂Cl₂ layer was concentrated and the residue was purified by chromatography on silica gel (short column, EtOAc as mobile phase for removing other components; MeOH/28% NH₄OH=97/3 as mobile phase for collecting 1-X) afforded crude 1-X (841 g).

Then Et₃N (167 g, 1 eq) and Boc₂O (360 g, 1 eq) were added to the solution of 1-X (841 g) in CH₂Cl₂ (8.4 L) at 25° C. The mixture was stirred at 25° C. for 15 hours. After the reaction was completed as evidenced by TLC, the solution was concentrated and EtOAc (5 L) was added to the resultant residue. The solution was concentrated to 3 L (½ of the original volume) under low pressure at 50° C. Then, n-hexane (3 L) was added to the concentrated solution. The solid product formed at 50° C. by seeding to afford the desired crude product 1-XI (600 g, 60% yield) after filtration and evaporation.

To compound 1-XI (120.0 g) and piperazine (1-XII, 50.0 g, 3 eq) in 1-pentanol (360 mL) was added Et₃N (60.0 g, 3.0 eq) at 25° C. The mixture was stirred at 120° C. for 8 hours. Ethyl acetate (480 mL) was added to the reaction mixture at 25° C. The solution was stirred for 1 h. The Et₃NHCl salt was filtered and the solution was concentrated and purified by silica gel (EtOAc/MeOH=2:8) to afforded 1-XIII (96 g) in a 74% yield.

A solution of intermediate 1-XIII (100 mg) was treated with 4 N HCl/dioxane (2 mL) in CH₂Cl₂ (1 mL) and stirred at 25° C. for 15 hours. The mixture was concentrated to give hydrochloride salt of compound 1 (51 mg).

CI-MS (M$^+$+1): 459.4

Example 2

Preparation of Compound 2

Intermediate 1-XIII was prepared as described in Example 1.

To a solution of 1-XIII (120 g) in MeOH (2.4 L) were added diethyl vinyl phosphonate (2-I, 45 g, 1.5 eq) at 25° C. The mixture was stirred under 65° C. for 24 hours. TLC and HPLC showed that the reaction was completed. The solution was concentrated and purified by silica gel (MeOH/CH₂Cl₂=8/92) to get 87 g of 2-II (53% yield, purity>98%, each single impurity<1%) after analyzing the purity of the product by HPLC.

A solution of 20% TFA/CH₂Cl₂ (36 mL) was added to a solution of intermediate 2-II (1.8 g) in CH₂Cl₂ (5 mL). The reaction mixture was stirred for 15 hours at room temperature and concentrated by removing the solvent to afford trifluoracetic acid salt of compound 2 (1.3 g).

CI-MS (M$^+$+1): 623.1

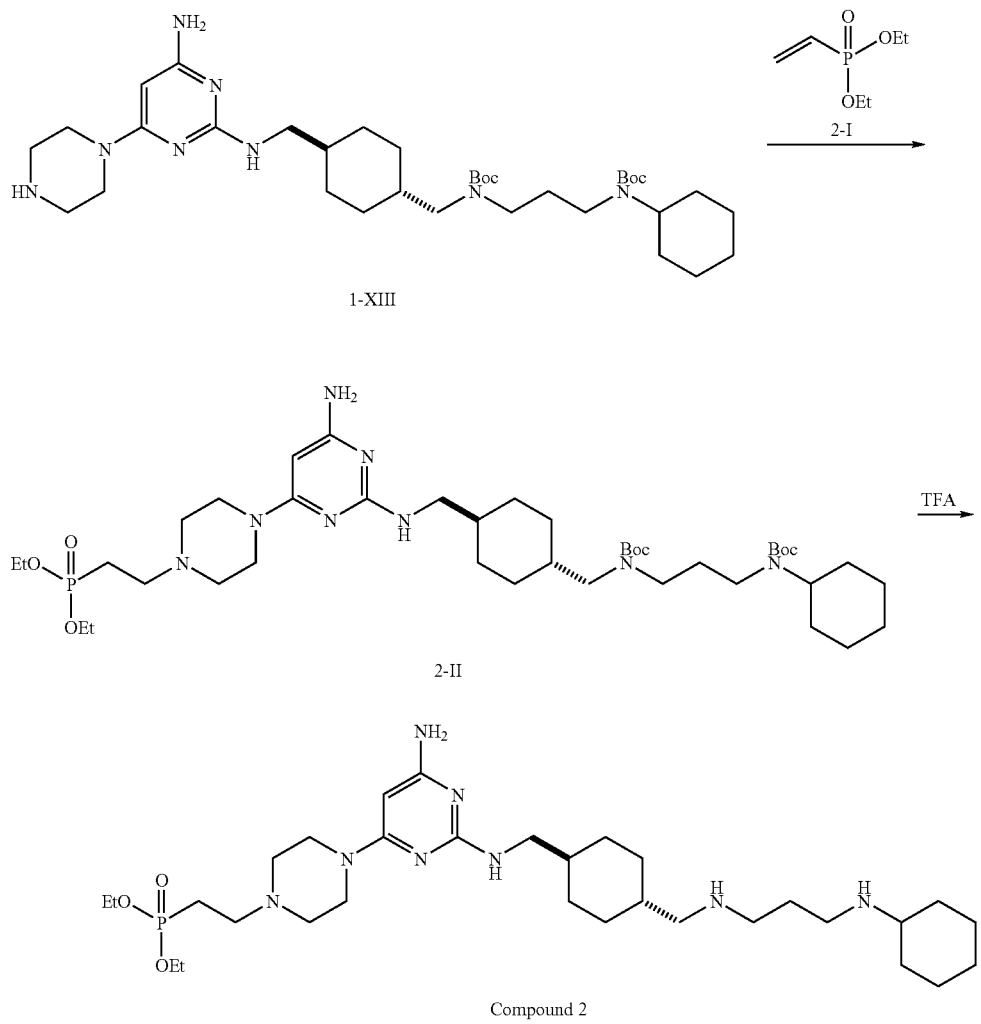

Example 3

Preparation of Compound 3

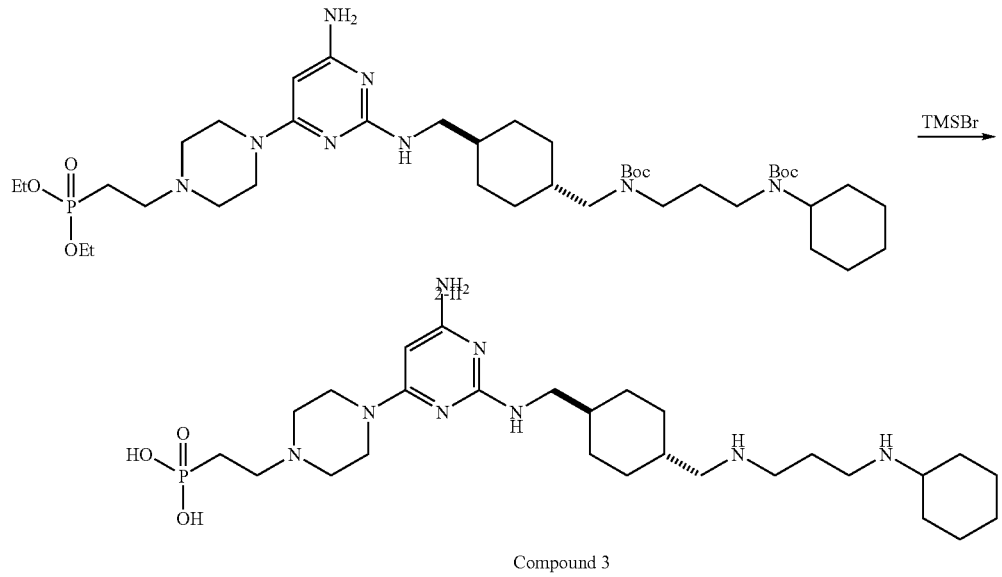

Intermediate 2-II was prepared as described in Example 2.

To a solution of 2-II (300 g) in CH$_2$Cl$_2$ (1800 mL) was added TMSBr (450 g, 8 eq) at 10-15° C. for 1 hour. The mixture was stirred at 25° C. for 15 hours. The solution was concentrated to remove TMSBr and solvent under vacuum at 40° C. CH$_2$Cl$_2$ was added to the mixture to dissolve the residue. TMSBr and solvent were removed under vacuum again to obtain 360 g crude solid after drying under vacuum (<1 torr) for 3 hours. Then, the crude solid was washed with 7.5 L IPA/MeOH (9/1) to afford compound 3 (280 g) after filtration and drying at 25° C. under vacuum (<1 torr) for 3 hours. Crystallization by EtOH gave hydrobromide salt of compound 3 (190 g). CI-MS (M$^+$+1): 567.0.

The hydrobromide salt of compound 3 (5.27 g) was dissolved in 20 mL water and treated with concentrated aqueous ammonia (pH=9-10), and the mixture was evaporated in vacuo. The residue in water (30 mL) was applied onto a column (100 mL, 4.5×8 cm) of Dowex 50WX8 (H$^+$ form, 100-200 mesh) and eluted (elution rate, 6 mL/min). Elution was performed with water (2000 mL) and then with 0.2 M aqueous ammonia. The UV-absorbing ammonia eluate was evaporated to dryness to afford ammonia salt of compound 3 (2.41 g). CI-MS (M$^+$+1): 567.3.

The ammonia salt of compound 3 (1.5 g) was dissolved in water (8 mL) and alkalified with concentrated aqueous ammonia (pH=11), and the mixture solution was applied onto a column (75 mL, 3×14 cm) of Dowex 1X2 (acetate form, 100-200 mesh) and eluted (elution rate, 3 mL/min). Elution was performed with water (900 mL) and then with 0.1 M acetic acid. The UV-absorbing acetic acid eluate was evaporated, and the residue was codistilled with water (5×50 mL) to afford compound 3 (1.44 g). CI-MS (M$^+$+1): 567.4.

Example 4

Preparation of Compound 4

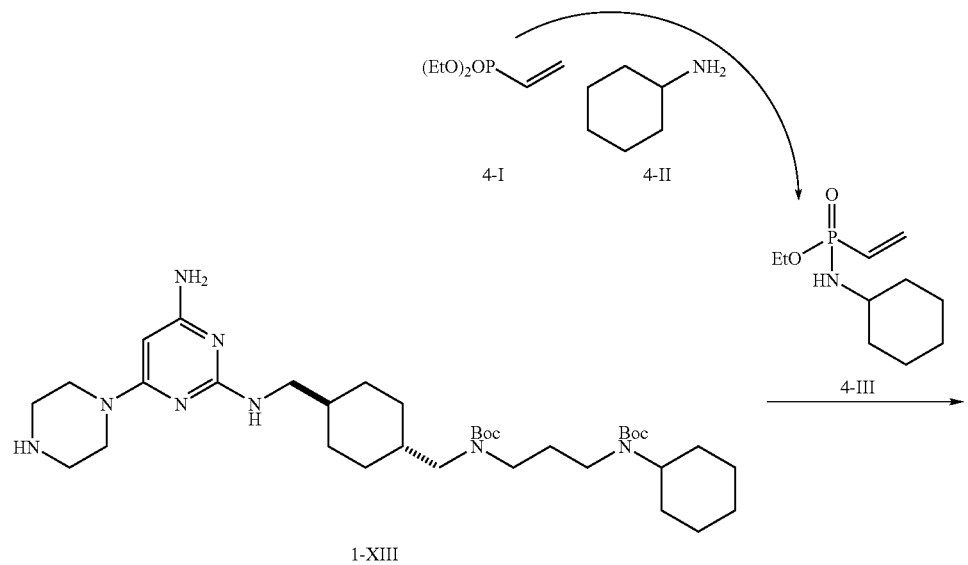

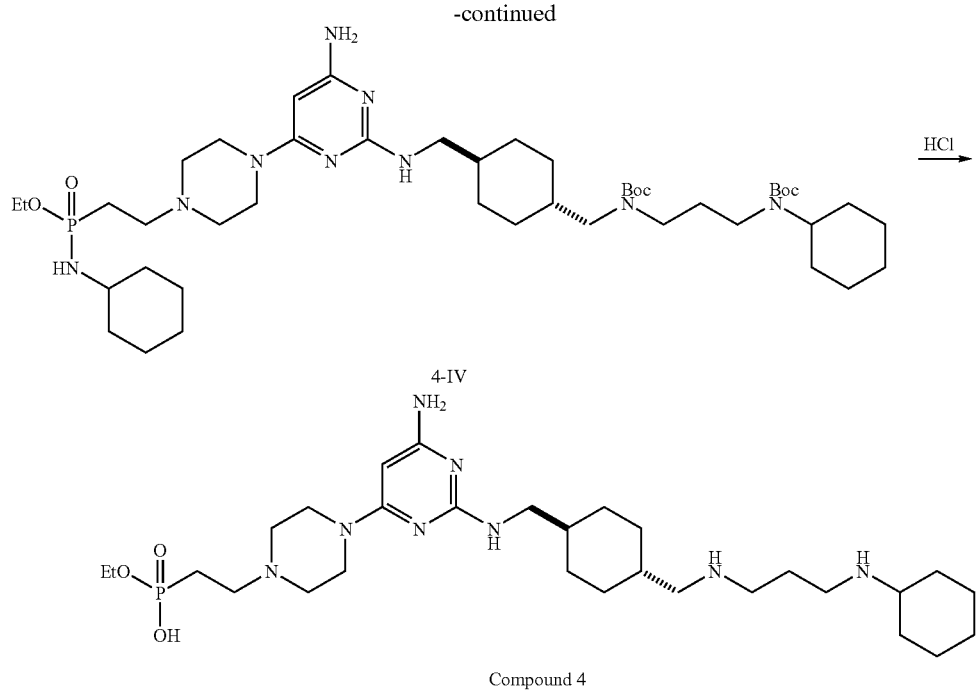

Compound 4

Intermediate 1-XIII was obtained during the preparation of compound 1.

To a solution of diethyl vinyl phosphonate (4-I, 4 g) in $CH_2Cl_2$ (120 mL) was added oxalyl chloride (15.5 g, 5 eq) and the mixture was stirred at 30° C. for 36 hours. The mixture were concentrated under vacuum on a rotatory evaporated to give quantitatively the corresponding phosphochloridate, which was added to a mixture of cyclohexyl amine (4-II, 5.3 g, 2.2 eq), $CH_2Cl_2$ (40 mL), and $Et_3N$ (6.2 g, 2.5 eq). The mixture was stirred at 35° C. for 36 hours, and then was washed with water. The organic layer was dried ($MgSO_4$), filtered, and evaporated to afford 4-III (4.7 g, 85% yield) as brown oil.

Compound 4-III (505 mg) was added to a solution of intermediate 1-XIII (500 mg) in MeOH (4 mL). The solution was stirred at 45° C. for 24 hours. The solution was concentrated and the residue was purified by column chromatography on silica gel (EtOAc/MeOH=4:1) to afford intermediate 4-IV (420 mg) in a 63% yield.

A solution of HCl in ether (5 mL) was added to a solution of intermediate 4-IV (420 mg) in $CH_2Cl_2$ (1.0 mL). The reaction mixture was stirred for 12 hours at room temperature and concentrated by removing the solvent. The resultant residue was washed with ether to afford hydrochloride salt of compound 4 (214 mg).

CI-MS ($M^+$+1): 595.1

Example 5

Preparation of Compound 5

Compound 5 was prepared in the same manner as that described in Example 1 except that homopiperazine was used instead of piperazine.

CI-MS ($M^+$+1): 473.1

Example 6

Preparation of Compound 6

Compound was prepared in the same manner as that described in Example 1 except that (R)-(−)-2-methylpiperazine was used instead of piperazine.

CI-MS ($M^+$+1): 473.4

Example 7

Preparation of Compound 7

Compound 7 was prepared in the same manner as that described in Example 1 except that (S)-(+)-2-methylpiperazine was used instead of piperazine.

CI-MS ($M^+$+1): 473.4

Example 8

Preparation of Compound 8

Compound 8 was prepared in the same manner as that described in Example 1 except that (S)-(−)-2-t-butyl-2-piperazinecarboxamide was used instead of piperazine.

CI-MS ($M^+$+1): 558.4

Example 9

Preparation of Compound 9

Compound 9 was prepared in the same manner as that described in Example 1 except that 2,6-dimethylpiperazine was used instead of piperazine.

CI-MS ($M^+$+1): 487.4

Example 10

Preparation of Compound 10

Compound 10 was prepared in the same manner as that described in Example 1 except that 2-phenylpiperazine was used instead of piperazine.
CI-MS (M$^+$+1): 535.4

Example 11

Preparation of Compound 11

Compound 11 was prepared in the same manner as that described in Example 1 except that (1S,4S)-2,5-diazabicyclo[2.2.1]heptane dihydrobromide was used instead of piperazine.
CI-MS (M$^+$+1): 471.4

Example 12

Preparation of Compound 12

Compound 12 was prepared in the same manner as that described in Example 1 except that 6,9-diaza-spiro[4.5]decane dihydrochloride was used instead of piperazine.
CI-MS (M$^+$+1): 513.4

Example 13

Preparation of Compound 13

Compound 13 was prepared in the same manner as that described in Example 1 except that 1,4-diaza-spiro[5.5]undecane dihydrochloride was used instead of piperazine.
CI-MS (M$^+$+1): 527.5

Example 14

Preparation of Compound 14

Compound 14 was prepared in the same manner as that described in Example 3 except that sodium 2-bromoethanesulfonate in the presence of Et$_3$N in DMF at 45° C. was used instead of diethyl vinyl phosphonate. Deportations of amino-protecting group by hydrochloride to afford hydrochloride salt of compound 14.
CI-MS (M$^+$+1): 567.3

Example 15

Preparation of Compound 15

Compound 15 was prepared in the same manner as that described in Example 3 except that methyl vinyl sulfone in MeOH at 40° C. was used instead of diethyl vinyl phosphonate. Deportations of amino-protecting group by hydrochloride to afford hydrochloride salt of compound 15.
CI-MS (M$^+$+1): 565.4

Example 16

Preparation of Compound 16

Compound 16 was prepared in the same manner as that described in Example 3 except that phenyl vinyl sulfone was used instead of diethyl vinyl phosphonate.
CI-MS (M$^+$+1): 627.4

Example 17

Preparation of Compound 17

Compound 17 was prepared in the same manner as that described in Example 2 except that diethyl-1-bromopropylphosphonate in the presence of K$_2$CO$_3$ in CH$_3$CN was used instead of diethyl vinyl phosphonate.
CI-MS (M$^+$+1): 637.5

Example 18

Preparation of Compound 18

Compound 18 was prepared in the same manner as that described in Example 3 except that diethyl-1-bromopropylphosphonate in the presence of K$_2$CO$_3$ in CH$_3$CN was used instead of diethyl vinyl phosphonate.
CI-MS (M$^+$+1): 581.4

Example 19

Preparation of Compound 19

Compound 19 was prepared in the same manner as that described in Example 3 except that diisopropyl-1-bromomethylphosphonate in the presence of K$_2$CO$_3$ in CH$_3$CN was used instead of diethyl vinyl phosphonate.
CI-MS (M$^+$+1): 553.3

Example 20

Preparation of Compound 20

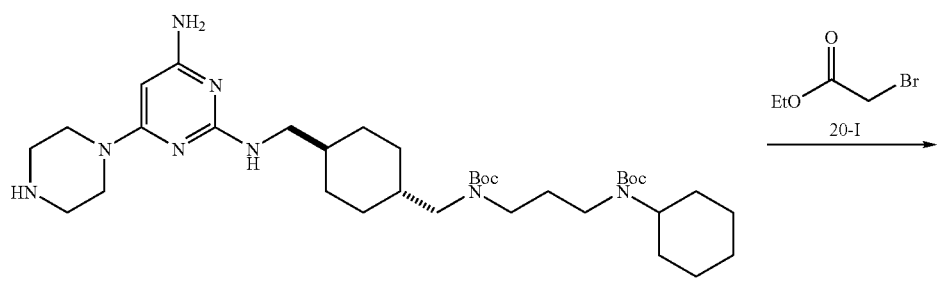

1-XIII

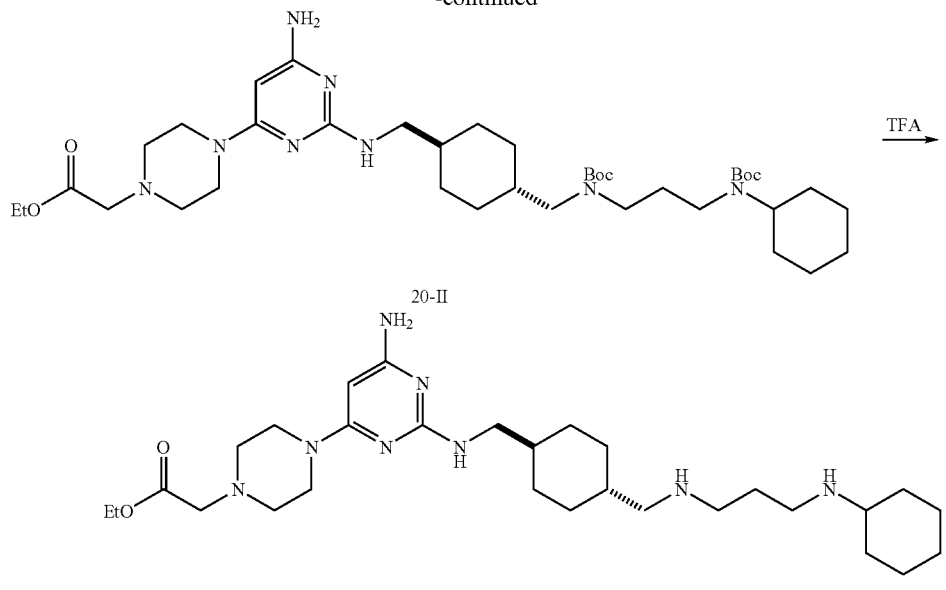

Compound 20

Intermediate 1-XIII was prepared as described in Example 1.

To a solution of 1-XIII (5 g) in CH$_3$CN (150 mL) were added ethyl bromoacetate (20-I, 1.25 g) and K$_2$CO$_3$ (3.1 g). The mixture was stirred at room temperature for 2 hours. The solution was filtered, concentrated and purification by silica gel (EtOAc and MeOH as eluant) afforded 20-II (5 g) in 88% yield.

To a solution of 20-II (4 g) in CH$_2$Cl$_2$ (60 mL) was added 20% TFA/CH$_2$Cl$_2$ (40 mL) was added and stirred at room temperature for overnight. The solution was concentrated and the residue in acetone (75 mL) was added HCl (4 N in 1,4-dioxane, 21.5 mL) at room temperature for 0.5 hour. The solvents was removed and the residual was treated with ether to afford hydrochloride salt 20 (3 g).

CI-MS (M$^+$+1): 545.5

Example 21

Preparation of Compound 21

Compound 21 was prepared in the same manner as that described in Example 2 except that homopiperazine was used instead of piperazine.

CI-MS (M$^+$+1): 637.4

Example 22

Preparation of Compound 22

Compound 22 was prepared in the same manner as that described in Example 3 except that homopiperazine was used instead of piperazine.

CI-MS (M$^+$+1): 581.2

Example 23

Preparation of Compound 23

Compound 23 was prepared in the same manner as that described in Example 4 except that homopiperazine was used instead of piperazine.

CI-MS (M$^+$+1): 609.4

Example 24

Preparation of Compound 24

Compound 24 was prepared in the same manner as that described in Example 17 except that homopiperazine was used instead of piperazine.

CI-MS (M$^+$+1): 651.4

Example 25

Preparation of Compound 25

Compound 25 was prepared in the same manner as that described in Example 14 except that homopiperazine was used instead of piperazine.

CI-MS (M$^+$+1): 581.4

Example 26

Preparation of Compound 26

Compound 26 was prepared in the same manner as that described in Example 15 except that homopiperazine was used instead of piperazine.

CI-MS (M$^+$+1): 579.3

Example 27

Preparation of Compound 27

Compound 27 was prepared in the same manner as that described in Example 16 except that homopiperazine was used instead of piperazine.

CI-MS (M$^+$+1): 641.5

Example 28

Preparation of Compound 28

Compound 28 was prepared in the same manner as that described in Example 2 except that (R)-(−)-2-methylpiperazine was used instead of piperazine.
CI-MS (M$^+$+1): 636.8

Example 29

Preparation of Compound 29

Compound 29 was prepared in the same manner as that described in Example 3 except that (R)-(−)-2-methylpiperazine was used instead of piperazine.
CI-MS (M$^+$+1): 581.1

Example 30

Preparation of Compound 30

Compound 30 was prepared in the same manner as that described in Example 17 except that (R)-(−)-2-methylpiperazine was used instead of piperazine.
CI-MS (M$^+$+1): 651.5

Example 31

Preparation of Compound 31

Compound 31 was prepared in the same manner as that described in Example 18 except that (R)-(−)-2-methylpiperazine was used instead of piperazine.
CI-MS (M$^+$+1): 595.4

Example 32

Preparation of Compound 32

Compound 32 was prepared in the same manner as that described in Example 2 except that (S)-(+)-2-methylpiperazine was used instead of piperazine.
CI-MS (M$^+$+1): 637.1

Example 33

Preparation of Compound 33

Compound 33 was prepared in the same manner as that described in Example 3 except that (S)-(+)-2-methylpiperazine was used instead of piperazine.
CI-MS (M$^+$+1): 581.1

Example 34

Preparation of Compound 34

Compound 34 was prepared in the same manner as that described in Example 17 except that (S)-(+)-2-methylpiperazine was used instead of piperazine.
CI-MS (M$^+$+1): 651.5

Example 35

Preparation of Compound 35

Compound 35 was prepared in the same manner as that described in Example 18 except that (S)-(+)-2-methylpiperazine was used instead of piperazine.
CI-MS (M$^+$+1): 595.5

Example 36

Preparation of Compound 36

Compound 36 was prepared in the same manner as that described in Example 3 except that (S)-(−)-2-t-butyl-2-piperazinecarboxamide was used instead of piperazine.
CI-MS (M$^+$+1): 666.5

Example 37

Preparation of Compound 37

Compound 37 was prepared in the same manner as that described in Example 17 except that (S)-(−)-2-t-butyl-2-piperazinecarboxamide was used instead of piperazine.
CI-MS (M$^+$+1): 736.5

Example 38

Preparation of Compound 38

Compound 38 was prepared in the same manner as that described in Example 18 except that (S)-(−)-2-t-butyl-2-piperazinecarboxamide was used instead of piperazine.
CI-MS (M$^+$+1): 680.5

Example 39

Preparation of Compound 39

Compound 39 was prepared in the same manner as that described in Example 17 except that 2,6-dimethylpiperazine was used instead of piperazine.
CI-MS (M$^+$+1): 665.5

Example 40

Preparation of Compound 40

Compound 40 was prepared in the same manner as that described in Example 18 except that 2,6-dimethylpiperazine was used instead of piperazine.
CI-MS (M$^+$+1): 609.5

Example 41

Preparation of Compound 41

Compound 41 was prepared in the same manner as that described in Example 2 except that 2-phenylpiperazine was used instead of piperazine.
CI-MS (M$^+$+1): 699.5

Example 42

Preparation of Compound 42

Compound 42 was prepared in the same manner as that described in Example 3 except that 2-phenylpiperazine was used instead of piperazine.

CI-MS (M$^+$+1): 643.4

Example 43

Preparation of Compound 43

Compound 43 was prepared in the same manner as that described in Example 17 except that 2-phenylpiperazine was used instead of piperazine.

CI-MS (M$^+$+1): 713.5

Example 44

Preparation of Compound 44

Compound 44 was prepared in the same manner as that described in Example 18 except that 2-phenylpiperazine was used instead of piperazine.

CI-MS (M$^+$+1): 657.4

Example 45

Preparation of Compound 45

Compound 45 was prepared in the same manner as that described in Example 2 except that (1S,4S)-2,5-diazabicyclo[2.2.1]heptane dihydrobromide was used instead of piperazine.

CI-MS (M$^+$+1): 635.5

Example 46

Preparation of Compound 46

Compound 46 was prepared in the same manner as that described in Example 3 except that (1S,4S)-2,5-diazabicyclo[2.2.1]heptane dihydrobromide was used instead of piperazine.

CI-MS (M$^+$+1): 579.4

Example 47

Preparation of Compound 47

Compound 47 was prepared in the same manner as that described in Example 17 except that 6,9-diaza-spiro[4.5]decane dihydrochloride was used instead of piperazine.

CI-MS (M$^+$+1): 691.5

Example 48

Preparation of Compound 48

Compound 48 was prepared in the same manner as that described in Example 18 except that 6,9-diaza-spiro[4.5]decane dihydrochloride was used instead of piperazine.

CI-MS (M$^+$+1): 635.5

Example 49

Preparation of Compound 49

Compound 49 was prepared in the same manner as that described in Example 17 except that 1,4-diaza-spiro[5.5]undecane dihydrochloride was used instead of piperazine.

CI-MS (M$^+$+1): 705.5

Example 50

Preparation of Compound 50

Compound 50 was prepared in the same manner as that described in Example 18 except that 1,4-diaza-spiro[5.5]undecane dihydrochloride was used instead of piperazine.

CI-MS (M$^+$+1): 649.5

Example 51

Preparation of Compound 51

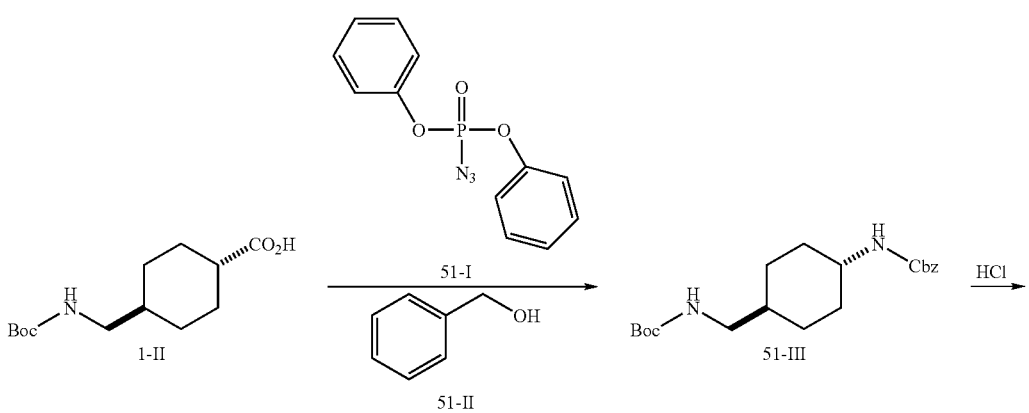

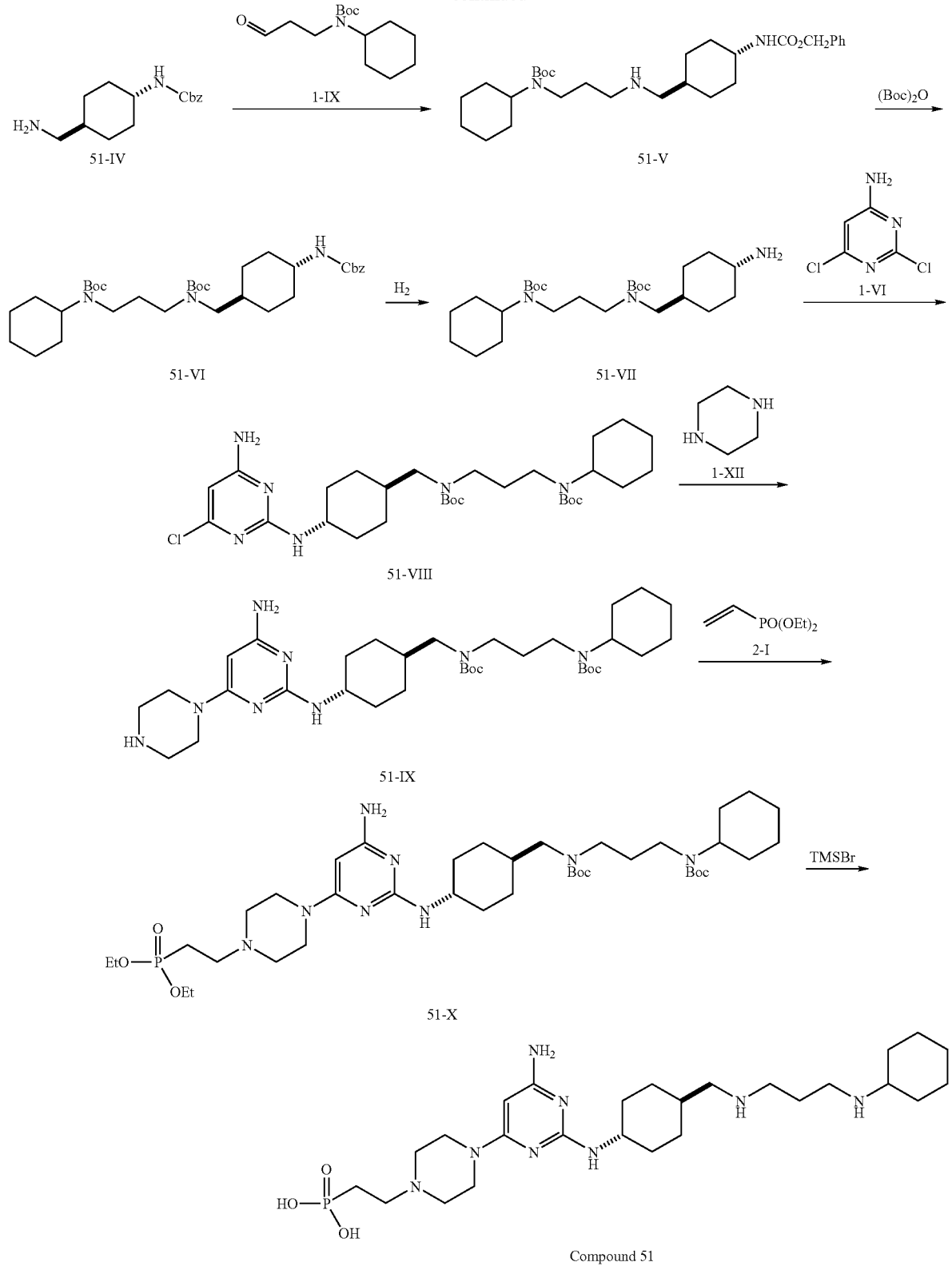

Intermediate 1-II was prepared as described in Example 1.

To a suspension of the intermediate 1-II (31.9 g) in toluene (150 mL) were added phosphorazidic acid diphenyl ester (51-I, 32.4 g) and Et$_3$N (11.9 g) at 25° C. for 1 hour. The reaction mixture was stirred at 80° C. for 3 hours and then cooled to 25° C. After benzyl alcohol (51-II, 20 g) was added, the reaction mixture was stirred at 80° C. for additional 3 hours and then warmed to 120° C. overnight. It was then concentrated and dissolved again in EtOAc and H$_2$O. The organic layer was collected. The aqueous layer was extracted with EtOAc. The combined organic layers were washed with 2.5 N HCl, saturated aqueous NaHCO$_3$ and brine, dried over anhydrous MgSO$_4$, filtered, and concentrated. The residue thus obtained was purified by column chromatography on silica gel (EtOAc/Hexane=1:2) to give Intermediate 51-III (35 g) in a 79% yield.

A solution of intermediate 51-III (35 g) treated with 4 N HCl/dioxane (210 mL) in MeOH (350 mL) was stirred at room temperature overnight. After ether (700 mL) was added, the solution was filtered. The solid was dried under vacuum. K$_2$CO$_3$ was added to a suspension of this solid in CH$_3$CN and iso-propanol at room temperature for 10 minutes. After water was added, the reaction mixture was stirred at room temperature for 2 hours, filtered, dried over anhydrous MgSO$_4$, and concentrated. The resultant residue was purified by column chromatography on silica gel (using CH$_2$Cl$_2$ and MeOH as an eluant) to give intermediate 51-IV (19 g) in a 76% yield.

Intermediate 1-IX (21 g) was added to a solution of intermediate 51-IV (19 g) in CH$_2$Cl$_2$ (570 mL). The mixture was stirred at 25° C. for 2 hours. NaBH(OAc)$_3$ (23 g) was then added at 25° C. overnight. After the solution was concentrated, a saturated aqueous NaHCO$_3$ solution was added to the resultant residue. The mixture was then extracted with CH$_2$Cl$_2$. The solution was concentrated and the residue was purified by column chromatography on silica gel (using EtOAc and MeOH as an eluant) to afford intermediate 51-V (23.9 g) in a 66% yield.

A solution of intermediate 51-V (23.9 g) and Boc$_2$O (11.4 g) in CH$_2$Cl$_2$ (200 mL) was added to Et$_3$N (5.8 mL) at 25° C. for overnight. The solution was then concentrated and the resultant residue was purified by column chromatography on silica gel (using EtOAc and Hexane as an eluant) to give intermediate 51-VI (22 g) in a 77% yield. 10% Pd/C (2.2 g) was added to a suspension of intermediate 51-VI (22 g) in MeOH (44 mL). The mixture was stirred at ambient temperature under hydrogen atmosphere overnight, filtered, and concentrated. The residue thus obtained was purified by column chromatography on silica gel (using EtOAc and MeOH as an eluant) to afford intermediate 51-VII (16.5 g) in a 97% yield.

Intermediate 51-VII (16.5 g) and Et$_3$N (4.4 mL) in 1-pentanol (75 mL) was allowed to react with 2,4-dichloro-6-aminopyrimidine (1-VI, 21 g) at 120° C. overnight. The solvent was then removed and the residue was purified by column chromatography on silica gel (using EtOAc and hexane as an eluant) to afford intermediate 51-VIII (16.2 g) in a 77% yield.

A solution of intermediate 51-VIII (16.2 g) and piperazine (1-XII, 11.7 g) in 1-pentanol (32 mL) was added to Et$_3$N (3.3 mL) at 120° C. overnight. After the solution was concentrated, the residue was treated with water and extracted with CH$_2$Cl$_2$. The organic layer was collected and concentrated. The residue thus obtained was purified by column chromatography on silica gel (using EtOAc/MeOH to 28% NH$_4$OH/MeOH as an eluant) to afford Intermediate 51-IX (13.2 g) in a 75% yield.

Diethyl vinyl phosphonate (2-I) was treated with 51-IX as described in Example 3 to afford hydrobromide salt of compound 51.
CI-MS (M$^+$+1): 553.3

Example 52

Preparation of Compound 52

Compound 52 was prepared in the same manner as that described in Example 4 except that intermediate 51-IX was used instead of intermediate 1-XIII.
CI-MS (M$^+$+1): 581.2

Example 53

Preparation of Compound 53

Compound 53 was prepared in the same manner as that described in Example 51 except that diethyl-1-bromopropylphosphonate in the presence of K$_2$CO$_3$ in CH$_3$CN was used instead of diethyl vinyl phosphonate.
CI-MS (M$^+$+1): 567.2

Example 54

Preparation of Compound 54

Compound 54 was prepared in the same manner as that described in Example 51 except that (R)-(−)-2-methylpiperazine was used instead of piperazine.
CI-MS (M$^+$+1): 566.7

Example 55

Preparation of Compound 55

Compound 55 was prepared in the same manner as that described in Example 53 except that (R)-(−)-2-methylpiperazine was used instead of piperazine.
CI-MS (M$^+$+1): 580.7

Example 56

Preparation of Compound 56

Compound 56 was prepared in the same manner as that described in Example 51 except that sodium 2-bromoethanesulfonate in the presence of Et$_3$N in DMF at 45° C. was used instead of diethyl vinyl phosphonate.
CI-MS (M$^+$+1): 553.2

Example 57

Preparation of Compound 57

Compound 57 was prepared in the same manner as that described in Example 51 except that methyl vinyl sulfone in MeOH at 40° C. was used instead of diethyl vinyl phosphonate. Deportations of amino-protecting group by hydrochloride to afford hydrochloride salt of compound 57.
CI-MS (M$^+$+1): 551.3

Example 58

Preparation of Compound 58

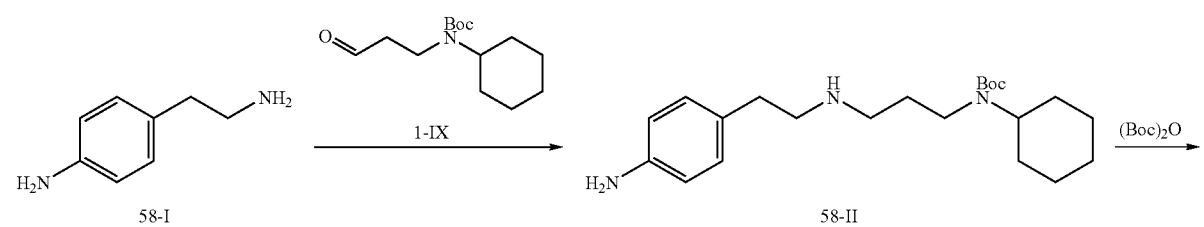

-continued
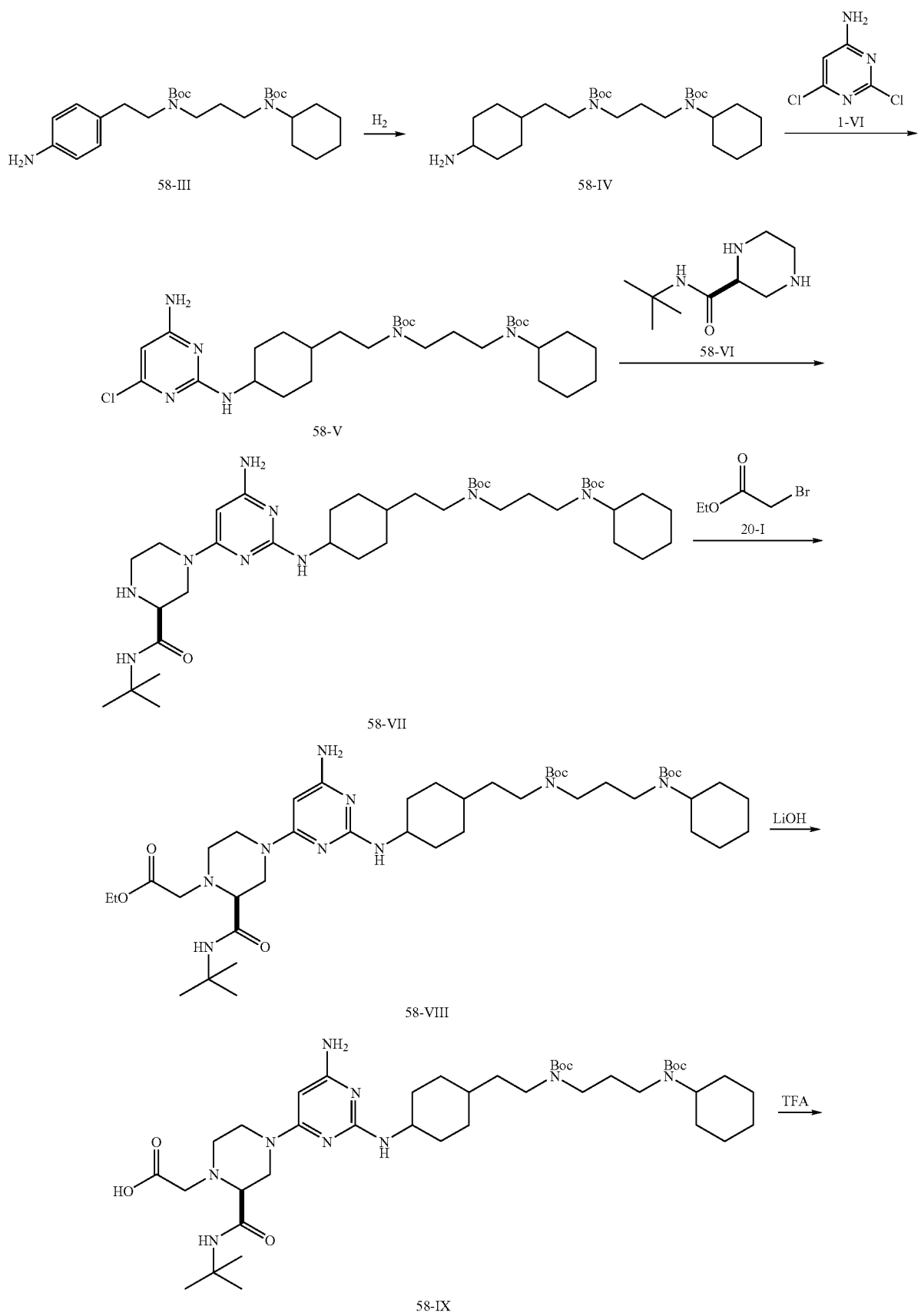

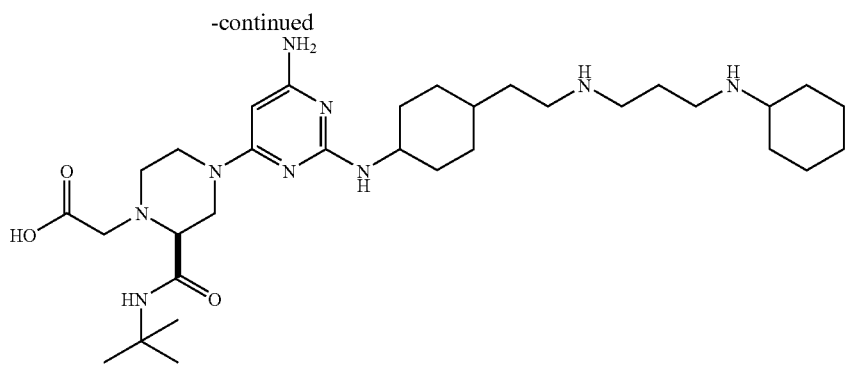

Compound 58

To a solution of 2-aminoethylaniline (58-1, 2.92 g) in MeOH (300 mL) was added 1-IX (4.56 g). The mixture was stirred at 60° C. for 8 h. Then, NaBH₄ (0.68 g) was added at 0° C. for 0.5 hour and concentrated by removing the solvent. To the resultant residue was added an aqueous solution of NH₄Cl (10%, 10 mL). The mixture was extracted with CH₂Cl₂, dried (MgSO4), filtered and evaporated. Purified by chromatography on silica gel (EtOAc/MeOH=1/1) to afford 58-II (4.2 g) in a 63% yield.

A solution of 58-II (4.2 g) and Boc₂O (2.8 g) in CH₂Cl₂ (250 mL) was added Et₃N (1.4 mL) at 25° C. for overnight. The solution was then concentrated and the resultant residue was purified by chromatography on silica gel (EtOAc/Hexane=1/5) to give 58-III (4 g) in a 75% yield.

Compound 58-III (4.0 g) in MeOH (20 mL) was hydrogenated at 50 psi at room temperature in the presence of 10% Pd/C (800 mg) and 5% Rh/C (400 mg) for 18 hours. The mixture was then filtered, evaporated, and the residue was purified by chromatography on silica gel (EtOAc/MeOH as eluant) to afford 58-IV (2.8 g) in a 69% yield.

Compound 58-IV (900 mg) and Et₃N (0.4 mL) in 1-pentanol (5 mL) was reacted with 2,4-dichloro-6-aminopyrimidine (1-VI, 365 mg) at 120° C. for 24 hours. The solvent was removed and the residue was purified by chromatography on silica gel (EtOAc/Hexane=1/1) to afford 58-V (842 mg) in a 74% yield.

(S)-(−)-2-t-butyl-2-piperazinecarboxamide (58-VI, 274 mg) was added to 58-V (300 mg) in 1-pentanol (1 mL) and the mixture was stirred at 120° C. for 18 hours. The solution was concentrated to give the residue which was coated with SiO₂ and purified by silica gel (EtOAc/MeOH=7/3) to afford 58-VII (242 mg) in a 65% yield.

To a solution of 58-VII (200 mg) in CH₃CN (20 mL) were added ethyl bromoacetate (20-I, 44 mg) and K₂CO₃ (182 mg). The mixture was stirred at 60° C. for 2 hours. The solution was filtered, concentrated and purification by silica gel (EtOAc and MeOH as eluant) afforded 58-VIII (133 mg) in a 60% yield.

Compound 58-VIII (500 mg) dissolved in THF (10 mL) was added 0.5 M LiOH (10 mL). The mixture was stirred at room temperature for 15 hours. Then, it was acidified with 2.5 M HCl (PH=9) and filtered to obtain yellow solid 58-IX. Purification by silica gel chromatography (EtOAc/MeOH to 21% NH₃ (aq)/MeOH as eluant) afforded intermediate 58-IX (324 mg) in a 67% yield.

To a solution of 58-IX (200 mg) in CH₂Cl₂ (2 mL) was added 20% TFA/CH₂Cl₂ (4 mL). The solution was stirred at room temperature for 2 hours. The solvents were removed to afford trifluoracetic acid salt of compound 58 (260 mg).

CI-MS (M⁺+1): 615.8

Example 59

Preparation of Compound 59

Compound 59 was prepared in the same manner as that described in Example 58 except that ethyl 3-bromopropionate was used instead of ethyl bromoacetate.

CI-MS (M⁺+1): 629.8

Example 60

Preparation of Compound 60

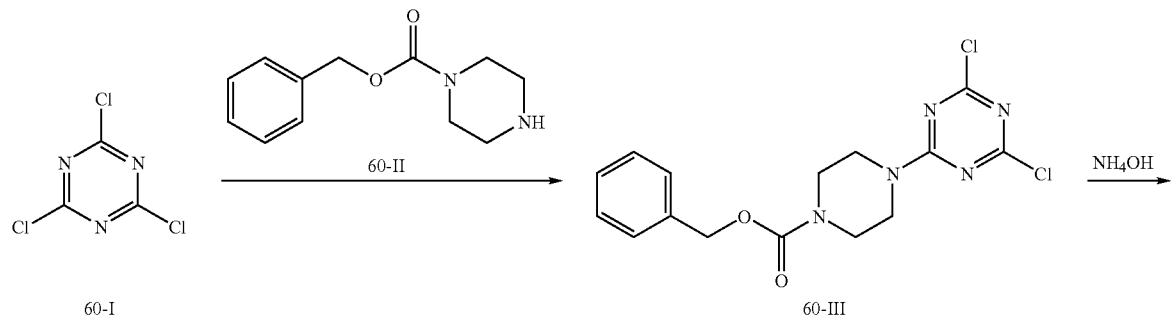

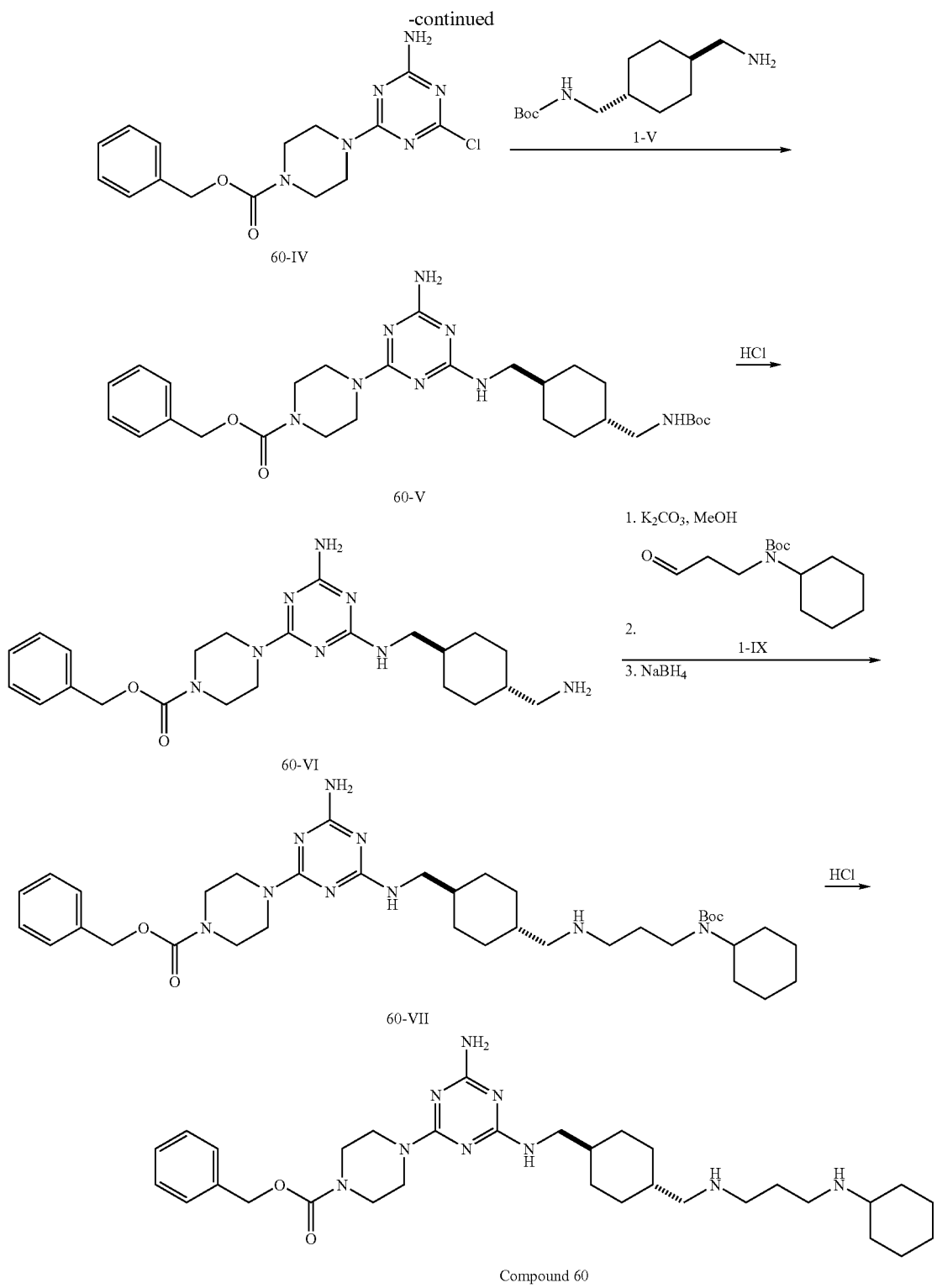

Intermediate 1-V was prepared as described in Example 1.

Benzyl 1-piperazinecarboxylate (60-II, 1.3 g) was dissolved in acetone (10 mL) and NaHCO$_3$ (0.5 g) in water (10 mL) was added simultaneously to solution of triazine 60-I (1.1 g) in acetone (24 mL) and water (36 mL) at 0° C. The solution was stirred at 25° C. for 2 hours to obtain a solid. Filtration afforded compound 60-III, which was used for the next step without purification.

To a solution of compound 60-III (2.0 g) in acetone (20 mL) was added aq. ammonium hydroxide solution (10 mL) at 25° C. After 15 hours, acetone was removed under reduced pressure and compound 60-IV was precipitated, filtered, washed with acetone (10 mL), and dried to give 1.9 g of 60-IV in a 91% overall yield.

A solution of intermediate 1-V (1.45 g) and Et$_3$N (1.6 mL) in iso-propylalcohol (10 mL) was reacted with compound 60-IV (1.9 g) at 60° C. for overnight. The reaction mixture was evaporated under reduced pressure. The residue thus obtained was purified by column chromatography on silica gel (EtOAc as an eluant) to afford intermediate 60-V (2.2 g) in a 70% yield.

A solution of intermediate 60-V (17 g) was treated with 4 N HCl/dioxane (160 mL) in MeOH (180 mL) and stirred at room temperature overnight. After ether was added, the solution was filtered. The solid thus obtained was dried under vacuum. To a solution of the above solid in MeOH was added $K_2CO_3$ at room temperature. The resultant mixture was stirred for 1 hour and was filtered. Intermediate 1-IX (7.78 g) was added. The mixture was stirred at 25° C. for 2 hours. $NaBH_4$ (1.0 g) was then added at 25° C. The mixture was stirred overnight and then concentrated. A saturated aqueous $NH_4Cl$ solution was added. The mixture was extracted with $CH_2Cl_2$. The organic layers were collected, dried over anhydrous $MgSO_4$, and concentrated. The residue was purified by column chromatography on silica gel (MeOH as an eluant) to afford intermediate 60-VII (16 g) in a 74% yield.

A solution of HCl in ether (3 mL) was added to a solution of intermediate 60-VII (200 mg) in $CH_2Cl_2$ (1.0 mL). The reaction mixture was stirred for 12 hours at room temperature and concentrated by removing the solvent. The resultant residue was washed with ether to afford hydrochloride salt of compound 60 (128 mg).

CI-MS ($M^+$+1): 594.2

Example 61

Preparation of Compound 61

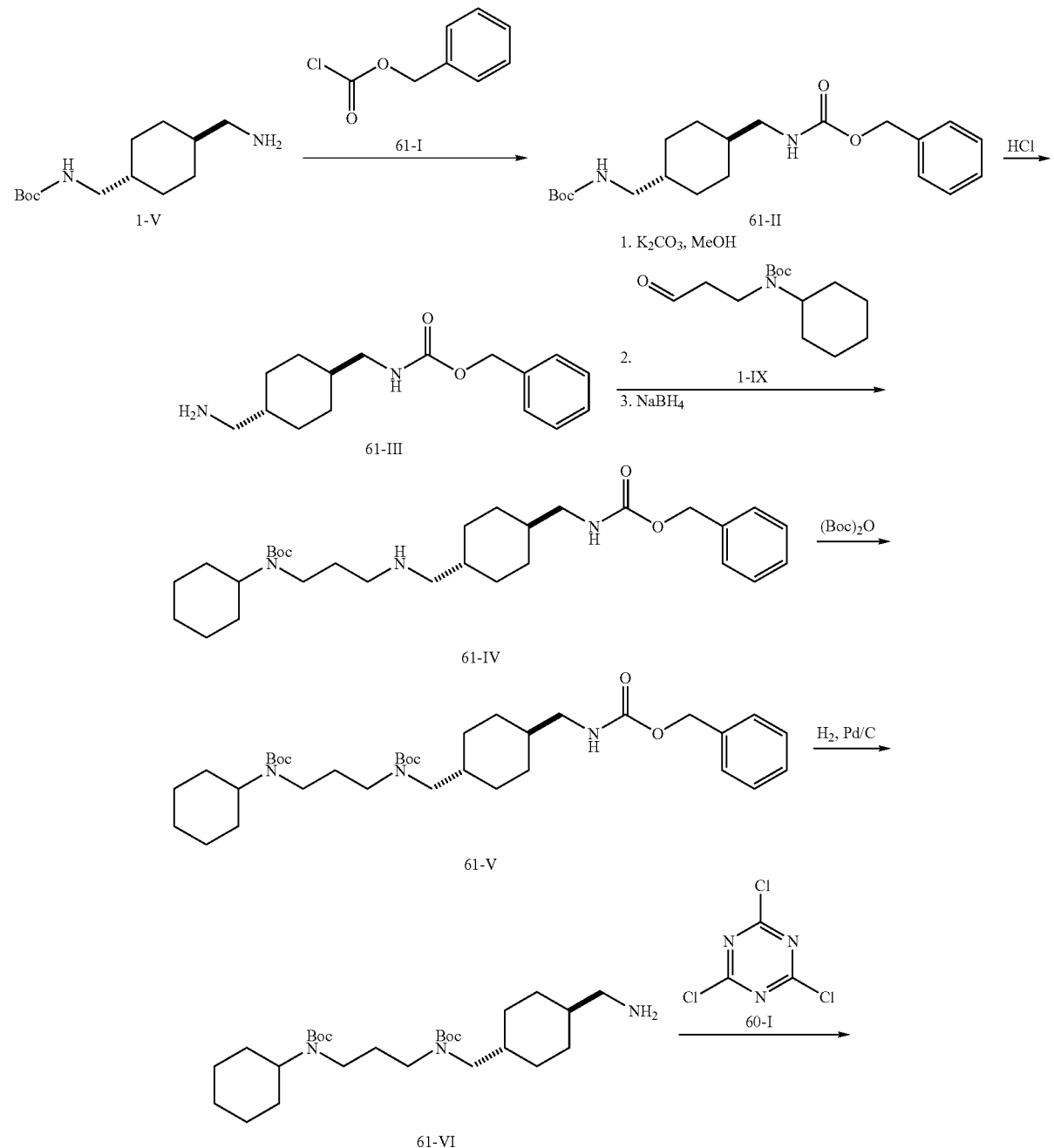

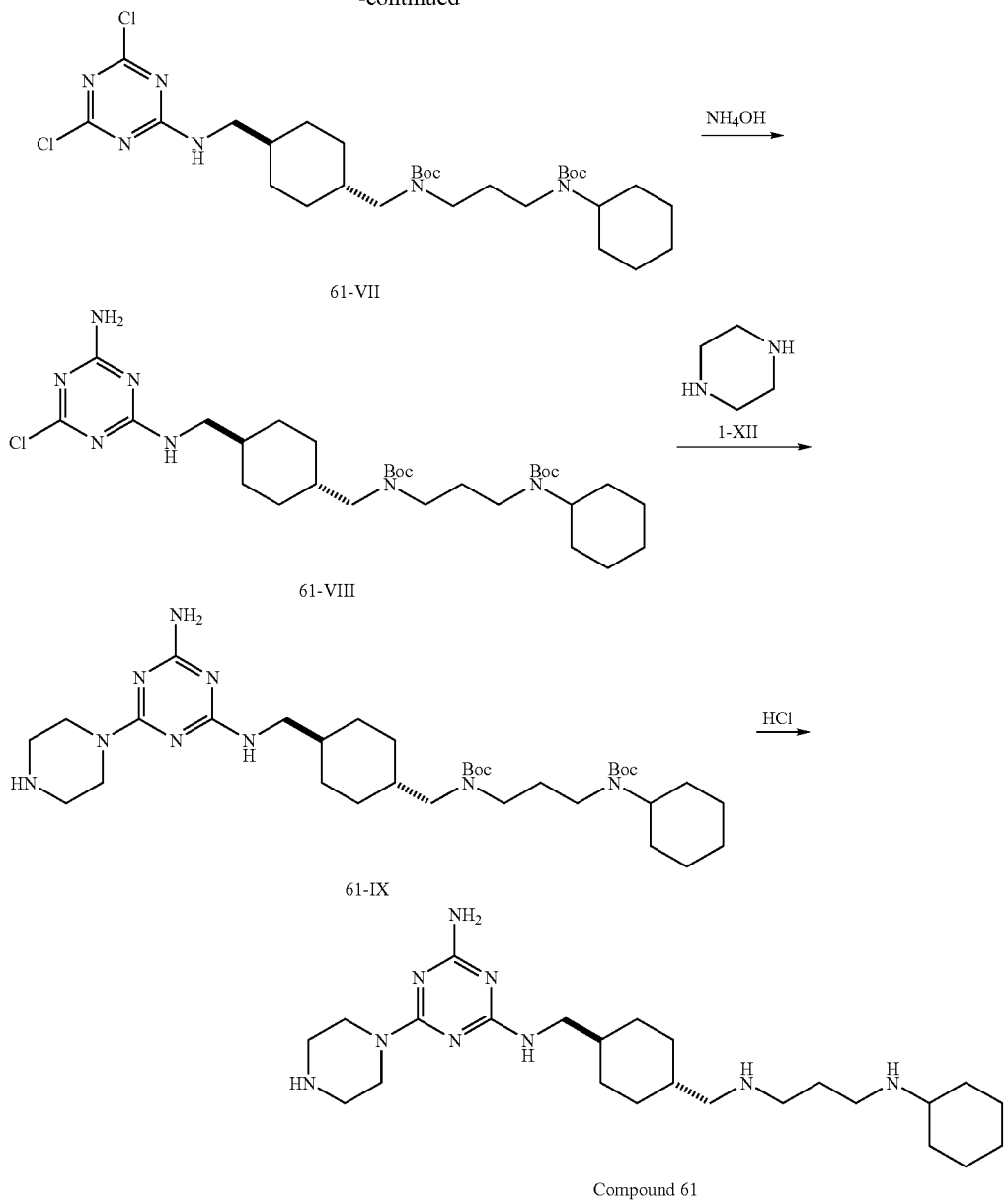

Compound 61

Intermediate 1-V was prepared as described in Example 1.

A solution of compound 1-V (120 g) and Et$_3$N (150 g, 3eq) in CH$_2$Cl$_2$ (2.6 L) was reacted with benzylchloroformate (61-I, 84 g, 1 eq) at −10° C. for 15 hours. TLC showed that the reaction was completed.

Intermediate 61-II (167 g) was treated with 4 N HCl/dioxane (280 mL) in MeOH (1.2 L). The mixture was stirred at room temperature overnight. After ether was added, the solution was filtered. The solid thus obtained was dried under vacuum. To a solution of the above solid in MeOH was added K$_2$CO$_3$ at room temperature. After stirred for 1 hour, the solution was filtered and intermediate 1-IX (101.2 g) was added. The mixture was stirred at 25° C. for 2 hours. NaBH$_4$ (12 g) was then added at 25° C. and the mixture was stirred overnight. The solution was then concentrated and a saturated aqueous NH$_4$Cl solution was added. The mixture was extracted with CH$_2$Cl$_2$, dried over anhydrous MgSO$_4$, filtered, and concentrated. The residue thus obtained was purified by column chromatography on silica gel (MeOH as an eluant) to afford intermediate 61-IV (100 g) in 32% yield.

Et$_3$N (29.2 mL) was added to a solution of intermediate 61-IV (80 g) and Boc$_2$O (5 g) in CH$_2$Cl$_2$ (200 mL) at 25° C. The solution was stirred overnight and then concentrated. The resultant residue was purified by column chromatography on silica gel (EtOAc as an eluant) to give intermediate 61-V (80 g) in 84% yield.

Catalytic hydrogenation of 61-V (38 g) with Pd/C (10%, 3.8 g) under H$_2$ (1 atm) in MeOH afforded intermediate 61-VI (29 g).

61-VI (26.1 g) dissolved in THF (200 mL) and N,N-diso-propylethylamine (7.8 g) dissolved in THF (200 mL) were added simultaneously to solution of triazine 60-I (10 g) in THF (200 mL) at 0° C. The solution was stirred at 25° C. for 2 hours to obtain a solid. Filtration afforded compound 61-VII, which was used for the next step without purification.

To a solution of compound 61-VII (30 g) in THF (1000 mL) was added aq. ammonium hydroxide solution (50 mL) at 25°

C. After 15 hours, THF was evaporated under reduced pressure and compound 61-VIII was precipitated, filtered, and dried to give 23.9 g of 61-VIII in a 70% overall yield.

To compound 61-VIII (2.0 g) and piperazine (1-XII, 0.83 g) in 1-pentanol (3 mL) was added Et₃N (0.97 g) at 25° C. The mixture was stirred at 120° C. for 8 hours. TLC showed that the reaction was completed. Ethyl acetate (480 mL) was added to the reaction mixture at 25° C. The solution was stirred for 1 hour. The Et₃NHCl salt was filtered and the solution was concentrated and purified by silica gel (EtOAc/MeOH=2:8) to afforded 61-IX (1.0 g) in a 46% yield.

A solution of HCl in ether (5 mL) was added to a solution of intermediate 61-IX (420 mg) in CH₂Cl₂ (1.0 mL). The reaction mixture was stirred for 12 hours at room temperature and concentrated by removing the solvent. The resultant residue was washed with ether to afford hydrochloride salt of compound 61 (293 mg).

CI-MS (M⁺+1): 460.0

Example 62

Preparation of Compound 62

Intermediate 61-VIII was prepared as described in Example 61.

Diethyl vinylphosphonate (2-I, 213 mg) was added to a solution of intermediate 61-VIII (570 mg) in MeOH (20 mL). The solution was stirred at 25° C. for 12 hours. The solution was then concentrated and the residue was purified by column chromatography on silica gel (EA/MeOH=5/1) to afford intermediate 62-I (290 mg) in a 42% yield.

A solution of 20% TFA/CH₂Cl₂ (5 mL) was added to a solution of intermediate 62-I (430 mg) in CH₂Cl₂ (2 mL). The reaction mixture was stirred for 8 hours at room temperature and concentrated by removing the solvent. The resultant residue was purified by column chromatography on silica gel (EA/MeOH=1/1) to afford trifluoracetic acid salt of compound 62 (175 mg).

CI-MS (M⁺+1): 642.4

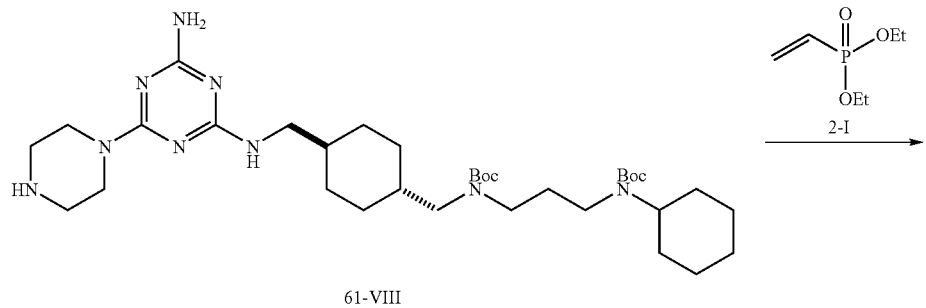

61-VIII

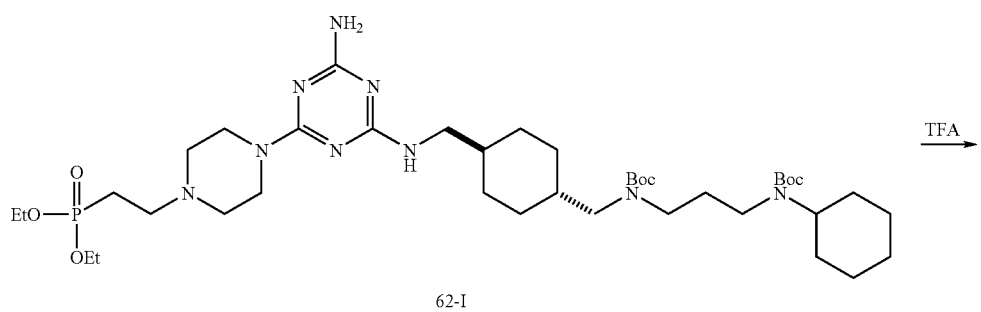

62-I

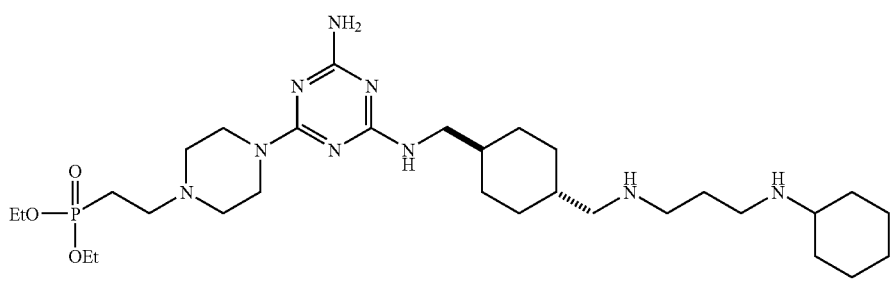

Compound 62

Example 63

Preparation of Compound 63

Intermediate 62-I was prepared as described in Example 62.

A solution of compound 62-I (610 mg) and trimethylsilyl bromide (1.21 g) in $CH_2Cl_2$ (30 mL) was stirred at 25° C. for 72 hours. The solution was then concentrated in vacuum to yield yellow-orange foam. Crystallization from EtOH gave hydrobromide salt of compound 63 (189 mg).

CI-MS (M$^+$+1): 568.0

Example 64

Preparation of Compound 64

Compound 64 was prepared in the same manner as that described in Example 61 except that homopiperazine was used instead of piperazine.

CI-MS (M$^+$+1): 474.4

Example 65

Preparation of Compound 65

Compound 65 was prepared in the same manner as that described in Example 61 except that (R)-(−)-2-methylpiperazine was used instead of piperazine.

CI-MS (M$^+$+1): 474.4

Example 66

Preparation of Compound 66

Compound 66 was prepared in the same manner as that described in Example 61 except that (S)-(+)-2-methylpiperazine was used instead of piperazine.

CI-MS (M$^+$+1): 474.1

Example 67

Preparation of Compound 67

Compound 67 was prepared in the same manner as that described in Example 61 except that (S)-(−)-2-t-butyl-2-piperazinecarboxamide was used instead of piperazine.

CI-MS (M$^+$+1): 559.5

Example 68

Preparation of Compound 68

Compound 68 was prepared in the same manner as that described in Example 61 except that 2,6-dimethylpiperazine was used instead of piperazine.

CI-MS (M$^+$+1): 488.1

Example 69

Preparation of Compound 69

Compound 69 was prepared in the same manner as that described in Example 61 except that 2-phenylpiperazine was used instead of piperazine.

CI-MS (M$^+$+1): 536.4

Example 70

Preparation of Compound 70

Compound 70 was prepared in the same manner as that described in Example 61 except that (1S,4S)-2,5-diazabicyclo[2.2.1]heptane dihydrobromide was used instead of piperazine.

CI-MS (M$^+$+1): 514.4

Example 71

Preparation of Compound 71

Compound 71 was prepared in the same manner as that described in Example 61 except that 6,9-diaza-spiro[4.5]decane dihydrochloride was used instead of piperazine.
CI-MS (M$^+$+1): 528.5

Example 72

Preparation of Compound 72

Compound 72 was prepared in the same manner as that described in Example 61 except that 1-methyl piperazine was used instead of piperazine.
CI-MS (M$^+$+1): 474.4

Example 73

Preparation of Compound 73

Compound 73 was prepared in the same manner as that described in Example 61 except that 1-(2-morpholinoethyl)-piperazine was used instead of piperazine.
CI-MS (M$^+$+1): 573.5

Example 74

Preparation of Compound 74

Compound 74 was prepared in the same manner as that described in Example 62 except that diethyl-1-bromopropylphosphonate in the presence of K$_2$CO$_3$ in CH$_3$CN was used instead of diethyl vinyl phosphonate.
CI-MS (M$^+$+1): 638.2

Example 75

Preparation of Compound 75

Compound 75 was prepared in the same manner as that described in Example 63 except that diethyl-1-bromopropylphosphonate in the presence of K$_2$CO$_3$ in CH$_3$CN was used instead of diethyl vinyl phosphonate.
CI-MS (M$^+$+1): 582.0

Example 76

Preparation of Compound 76

Compound 76 was prepared in the same manner as that described in Example 63 except that N-valeryl chloride in the presence of DIPEA in CH$_2$Cl$_2$ was used instead of diethyl vinyl phosphonate. Deportations of amino-protecting group by hydrochloride to afford hydrochloride salt of compound 76.
CI-MS (M$^+$+1): 544.4

Example 77

Preparation of Compound 77

Compound 77 was prepared in the same manner as that described in Example 63 except that ethyl 4-bromobutyrate in the presence of K$_2$CO$_3$ in CH$_3$CN was used instead of diethyl vinyl phosphonate. Hydrolysis of ether group by LiOH afforded amino acid compound. Removal of amino-protecting group by trifluoracetic acid afforded trifluoracetic acid salt of compound 77.
CI-MS (M$^+$+1): 546.2

Example 78

Preparation of Compound 78

Compound 78 was prepared in the same manner as that described in Example 63 except that sodium 2-bromoethanesulfonate in the presence of Et$_3$N in DMF at 45° C. was used instead of diethyl vinyl phosphonate. Removal of amino-protecting group by hydrochloride afforded hydrochloride salt of compound 79.
CI-MS (M$^+$+1): 568.3

Example 79

Preparation of Compound 79

Compound 79 was prepared in the same manner as that described in Example 78 except that methyl vinyl sulfone in MeOH at 40° C. was used instead of diethyl vinyl phosphonate. Deportations of amino-protecting group by hydrochloride to afford hydrochloride salt of compound 79.
CI-MS (M$^+$+1): 566.2

Example 80

Preparation of Compound 80

Compound 80 was prepared in the same manner as that described in Example 62 except that homopiperazine was used instead of piperazine.
CI-MS (M$^+$+1): 638.5

Example 81

Preparation of Compound 81

Compound 81 was prepared in the same manner as that described in Example 63 except that homopiperazine was used instead of piperazine.
CI-MS (M$^+$+1): 582.4

Example 82

Preparation of Compound 82

Compound 82 was prepared in the same manner as that described in Example 74 except that homopiperazine was used instead of piperazine.
CI-MS (M$^+$+1): 652.5

Example 83

Preparation of Compound 83

Compound 83 was prepared in the same manner as that described in Example 75 except that homopiperazine was used instead of piperazine.
CI-MS (M$^+$+1): 596.4

Example 84

Preparation of Compound 84

Compound 84 was prepared in the same manner as that described in Example 62 except that (R)-(−)-2-methylpiperazine was used instead of piperazine.
CI-MS (M$^+$+1): 638.3

Example 85

Preparation of Compound 85

Compound 85 was prepared in the same manner as that described in Example 63 except that (R)-(−)-2-methylpiperazine was used instead of piperazine.
CI-MS (M$^+$+1): 582.2

Example 86

Preparation of Compound 86

Compound 86 was prepared in the same manner as that described in Example 74 except that (R)-(−)-2-methylpiperazine was used instead of piperazine.
CI-MS (M$^+$+1): 652.5

Example 87

Preparation of Compound 87

Compound 87 was prepared in the same manner as that described in Example 75 except that (R)-(−)-2-methylpiperazine was used instead of piperazine.
CI-MS (M$^+$+1): 596.2

Example 88

Preparation of Compound 88

Compound 88 was prepared in the same manner as that described in Example 63 except that (S)-(+)-2-methylpiperazine was used instead of piperazine.
CI-MS (M$^+$+1): 582.4

Example 89

Preparation of Compound 89

Compound 89 was prepared in the same manner as that described in Example 74 except that (S)-(+)-2-methylpiperazine was used instead of piperazine.
CI-MS (M$^+$+1): 652.5

Example 90

Preparation of Compound 90

Compound 90 was prepared in the same manner as that described in Example 75 except that (S)-(+)-2-methylpiperazine was used instead of piperazine.
CI-MS (M$^+$+1): 596.0

Example 91

Preparation of Compound 91

Compound 91 was prepared in the same manner as that described in Example 74 except that (S)-(−)-2-t-butyl-2-piperazinecarboxamide was used instead of piperazine.
CI-MS (M$^+$+1): 737.6

Example 92

Preparation of Compound 92

Compound 92 was prepared in the same manner as that described in Example 75 except that (S)-(−)-2-t-butyl-2-piperazinecarboxamide was used instead of piperazine.
CI-MS (M$^+$+1): 681.5

Example 93

Preparation of Compound 93

Compound 93 was prepared in the same manner as that described in Example 74 except that 2,6-dimethylpiperazine was used instead of piperazine.
CI-MS (M$^+$+1): 666.5

Example 94

Preparation of Compound 94

Compound 94 was prepared in the same manner as that described in Example 75 except that 2,6-dimethylpiperazine was used instead of piperazine.
CI-MS (M$^+$+1): 610.4

Example 95

Preparation of Compound 95

Compound 95 was prepared in the same manner as that described in Example 75 except that 2-phenylpiperazine was used instead of piperazine.
CI-MS (M$^+$+1): 658.4

Example 96

Preparation of Compound 96

Compound 96 was prepared in the same manner as that described in Example 74 except that 6,9-diaza-spiro[4.5]decane dihydrochloride was used instead of piperazine.
CI-MS (M$^+$+1): 692.5

Example 97

Preparation of Compound 97

Compound 97 prepared in the same manner as that described in Example 75 except that 6,9-diaza-spiro[4.5]decane dihydrochloride was used instead of piperazine.

CI-MS (M$^+$+1): 636.5

Example 98

Preparation of Compound 98

Compound 98 was prepared in the same manner as that described in Example 75 except that 1,4-diaza-spiro[5.5]undecane dihydrochloride was used instead of piperazine.

CI-MS (M$^+$+1): 650.5

Example 99

Preparation of Compound 99

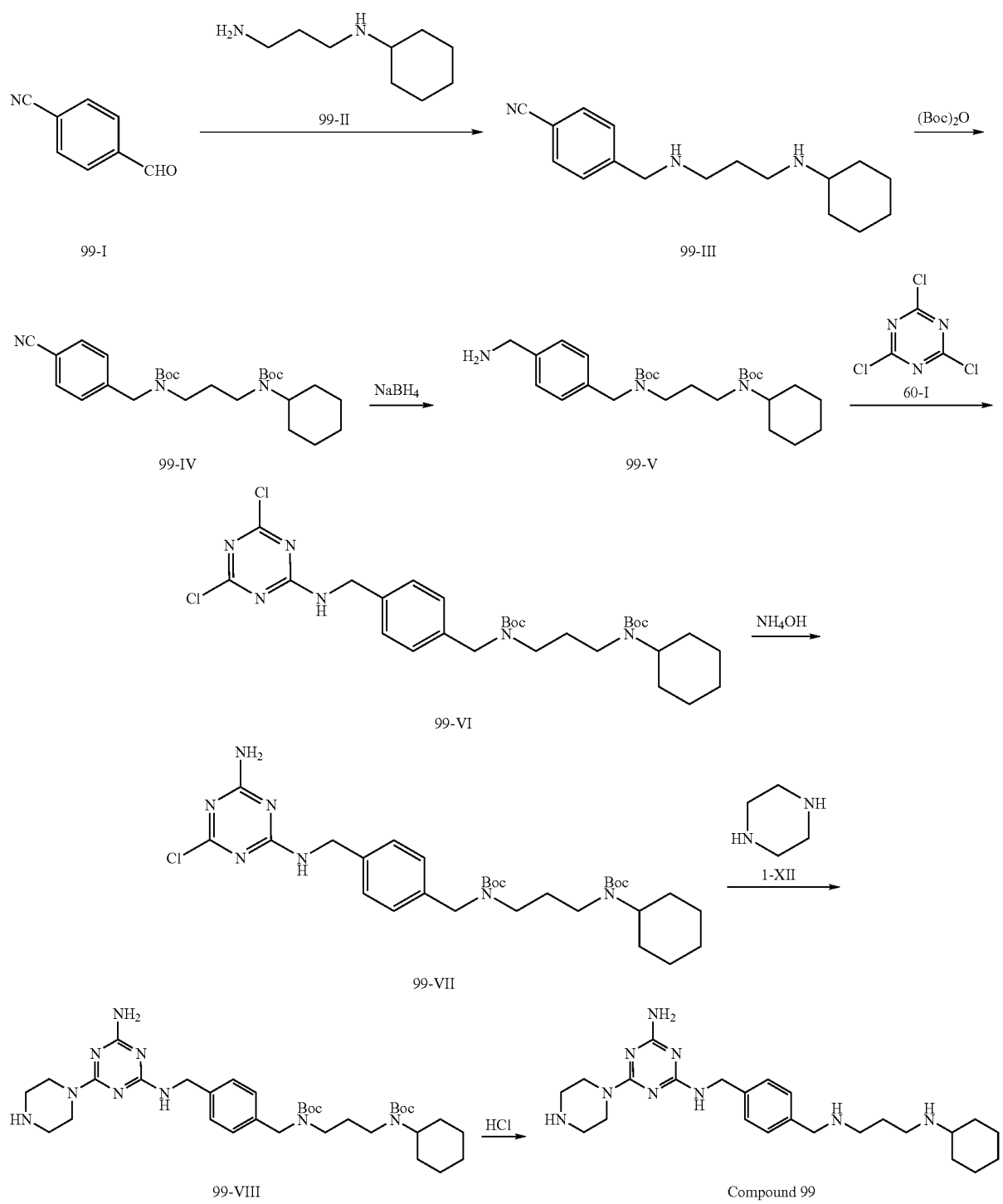

A solution of 4-cyanobenzylaldehyde (99-I, 5 g) and N-cyclohexyl-1,3-propane-diamine (99-II, 6 g) in CH₃OH (100 mL) was heated to 60° C. for 6 hours. After cooling to room temperature, NaBH₄ (2.5 g) was slowly added to the solution. The mixture was stirred for another 30 minutes, and was then concentrated, quenched with NH₄Cl (aq), and extracted with CH₂Cl₂. The organic layers were combined, dried with anhydrous MgSO₄, and concentrated to give a residue. The residue was purified by chromatography on silica gel (EtOAc/Et₃N=4/1) to afford Intermediate 99-III (7.2 g) in a 70% yield.

A solution of Intermediate 99-III (7.2 g) and Boc₂O (17.3 g) in CH₂Cl₂ (280 ml) was stirred at 25° C. for 15 hours and then concentrated. The resultant residue was purified by chromatography on silica gel (EtOAc/Hexane=1/1) to afford Intermediate 99-IV as a yellow oil (10.6 g, yield: 85%).

A solution of Intermediate 99-IV (4.7 g) and NiCl₂ (64 mg) in CH₃OH (100 ml) was stirred at 25° C. After cooling to 0° C., NaBH₄ (1.83 g) was slowly added and the mixture was stirred for another 15 hours. The solution was concentrated, quenched with NH₄Cl (aq), and extracted with CH₂Cl₂. The combined organic layer was washed with water, filtered, dried with anhydrous MgSO₄, and concentrated to give a residue. The residue was purified by chromatography on silica gel (21% NH₃(aq)/MeOH=1/19) to afford Intermediate 99-V (2.36 g) in a 50% yield.

99-V (3.4 g) dissolved in THF (50 mL) and N,N-disopropylethylamine (0.92 g) dissolved in THF (50 mL) were added simultaneously to triazine 60-I (1.3 g) in THF (50 mL) at 0° C. The solution was stirred at 25° C. for 2 hours to obtain a solid. Filtration afforded compound 99-VI, which was used for the next step without purification.

To a solution of compound 99-VI (4.3 g) in THF (100 mL) was added aq. ammonium hydroxide solution (10 mL) at 25° C. After 15 hours, THF was evaporated under reduced pressure and compound 99-VII was precipitated, filtered, and dried to give 3 g of 99-VII in a 70% overall yield.

To compound 99-VII (500 mg) and piperazine (1-XII, 211 mg) in 1-pentanol (3 mL) was added Et₃N (248 mg) at 25° C. The mixture was stirred at 120° C. for 8 hours. TLC showed that the reaction was completed. Ethyl acetate (120 mL) was added to the reaction mixture at 25° C. The solution was stirred for 1 hour. The Et₃NHCl salt was filtered and the solution was concentrated and purified by silica gel (EtOAc/MeOH=2:8) to afforded 99-VIII (460 mg) in a 85% yield.

A solution of HCl in ether (5 mL) was added to a solution of intermediate 99-VIII (200 mg) in CH₂Cl₂ (1.0 mL). The reaction mixture was stirred for 12 hours at room temperature and concentrated by removing the solvent. The resultant residue was washed with ether to afford hydrochloride salt of compound 99 (110 mg).

CI-MS (M⁺+1): 454.1

Example 100

Preparation of Compound 100

Compound 100 was prepared in a manner the same as that described in Example 99 except that 1-methyl piperazine was used instead of piperazine.

CI-MS (M⁺+1): 468.0

Example 101

Preparation of Compound 101

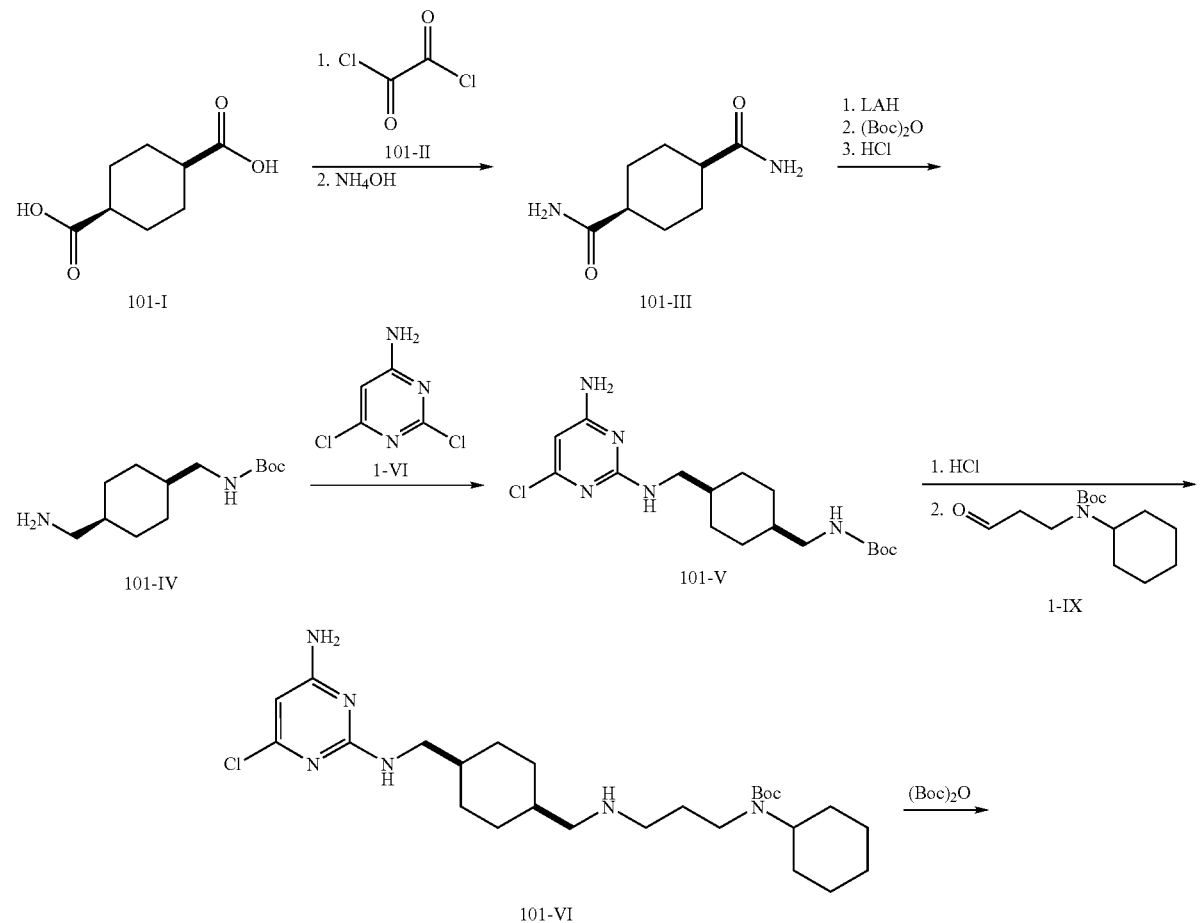

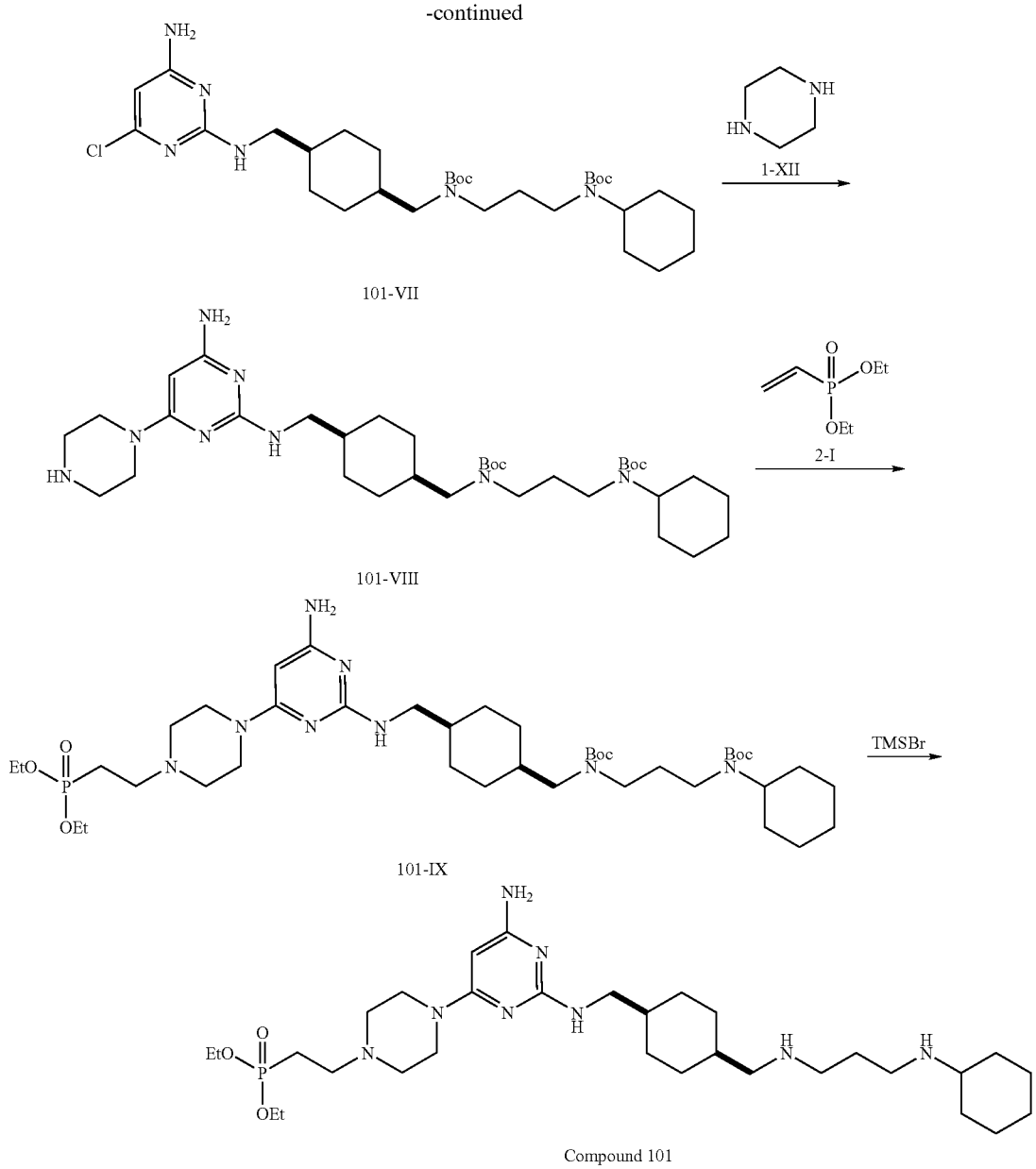

Cis-1,4-cyclohexanedicarboxylic acid (101-I, 10 g) in THF (100 ml) was added oxalyl chloride (101-II, 15.5 g) at 0° C. and then DMF (few drops). The mixture was stirred at room temperature for 15 hours. The solution was concentrated and the residue was dissolved in THF (100 ml). The mixture solution was added to ammonium hydroxide (80 ml) and stirred for 1 hour. The solution was concentrated and filtration to afford crude product 101-III (7.7 g).

Compound 101-III (7.7 g) in THF (200 ml) was slowly added to LiAlH$_4$ (8.6 g) in THF (200 ml) solution at 0° C. The mixture solution was stirred at 65° C. for 15 hours. NaSO$_4$.10H$_2$O was added at room temperature and stirred for 1 hours. The resultant mixture was filtered to get filtrate and concentrated. The residue was dissolved in CH$_2$Cl$_2$ (100 ml). Et$_3$N (27 g) and (Boc)$_2$O (10 g) were added at room temperature. The solution was stirred for 15 h, and then concentrated to get resultant residue. Ether was added to the resultant residue. Filtration and drying under vacuum afforded solid crude product 101-IV (8.8 g).

A solution of compound 101-IV (1.1 g) and Et$_3$N (1.7 g) in 1-pentanol (10 ml) was reacted with 2,4-dichloro-6-aminopyrimidine (1-VI, 910 mg) at 90° C. for 15 hours. TLC showed that the reaction was completed. Ethyl acetate (10 mL) was added to the reaction mixture at 25° C. The solution was stirred for 1 hour. The Et$_3$NHCl salt was removed. The filtrate was concentrated and purified by silica gel (EtOAc/Hex=1:2) to afford the desired product 101-V (1.1 g, 65% yield).

A solution of intermediate 101-V (1.1 g) was treated with 4 N HCl/dioxane (10 ml) in MeOH (10 ml) and stirred at 25° C. for 15 hours. TLC showed that the reaction was completed. The mixture was concentrated, filtered, and dried under vacuum (<10 torr). For neutralization, K$_2$CO$_3$ (3.2 g) was added to the solution of HCl salt in MeOH (20 ml) at 25° C. The mixture was stirred at the same temperature for 3 hours (pH>12) and filtered. Aldehyde 1-IX (759 mg) was added to the filtrate at 0-10° C. The reaction was stirred at 0-10° C. for 3 hours. TLC showed that the reaction was completed. Then, NaBH$_4$ (112 mg) was added at less than 10° C. and the solution was stirred at 10-15° C. for 1 hour. The solution was concentrated to get a residue, which was then treated with CH$_2$Cl$_2$ (10 mL). The mixture was washed with saturated NH$_4$Cl (aq) solution. The CH$_2$Cl$_2$ layer was concentrated and the residue was purified by chromatography on silica gel (MeOH/28% NH$_4$OH=97/3) to afford intermediate 101-VI (1.0 g, 66% yield).

Et$_3$N (600 mg) and Boc$_2$O (428 mg) were added to the solution of 101-VI (1.0 g) in CH$_2$Cl$_2$ (10 ml) at 25° C. The mixture was stirred at 25° C. for 15 hours. TLC showed that the reaction was completed. The solution was concentrated and purified by chromatography on silica gel (EtOAc/Hex=1:1) to afford intermediate 101-VII (720 mg, 60% yield).

To a solution compound 101-VII (720 mg) and piperazine (1-XII, 1.22 g) in 1-pentanol (10 mL) was added Et$_3$N (1.43 g) at 25° C. The mixture was stirred at 120° C. for 24 hours. TLC showed that the reaction was completed. Ethyl acetate (20 mL) was added at 25° C. The solution was stirred for 1 hour. The Et$_3$NHCl salt was removed and the solution was concentrated and purified by silica gel (EtOAc/MeOH=2:8) to afford 101-VIII (537 mg) in 69% yield.

To a solution of 101-VIII (537 mg) in MeOH (11 ml) was added diethyl vinyl phosphonate (2-I, 201 mg) at 25° C. The mixture was stirred under 65° C. for 24 hours. TLC and HPLC showed that the reaction was completed. The solution was concentrated and purified by silica gel (MeOH/CH$_2$Cl$_2$=1:9) to get 101-IX (380 mg) in a 57% yield.

To a solution of 101-IX (210 mg) in CH$_2$Cl$_2$ (5 ml) was added TMSBr (312 mg) at 10-15° C. for 1 hour. The mixture was stirred at 25° C. for 15 hours. The solution was concentrated to remove TMSBr and solvent under vacuum at 40° C., then, CH$_2$Cl$_2$ was added to dissolve the residue. Then TMSBr and solvent were further removed under vacuum and CH$_2$Cl$_2$ was added for four times repeatedly. The solution was concentrated to get hydrobromide salt of compound 101 (190 mg).

CI-MS (M$^+$+1): 566.9

Example 102

Preparation of Compound 102

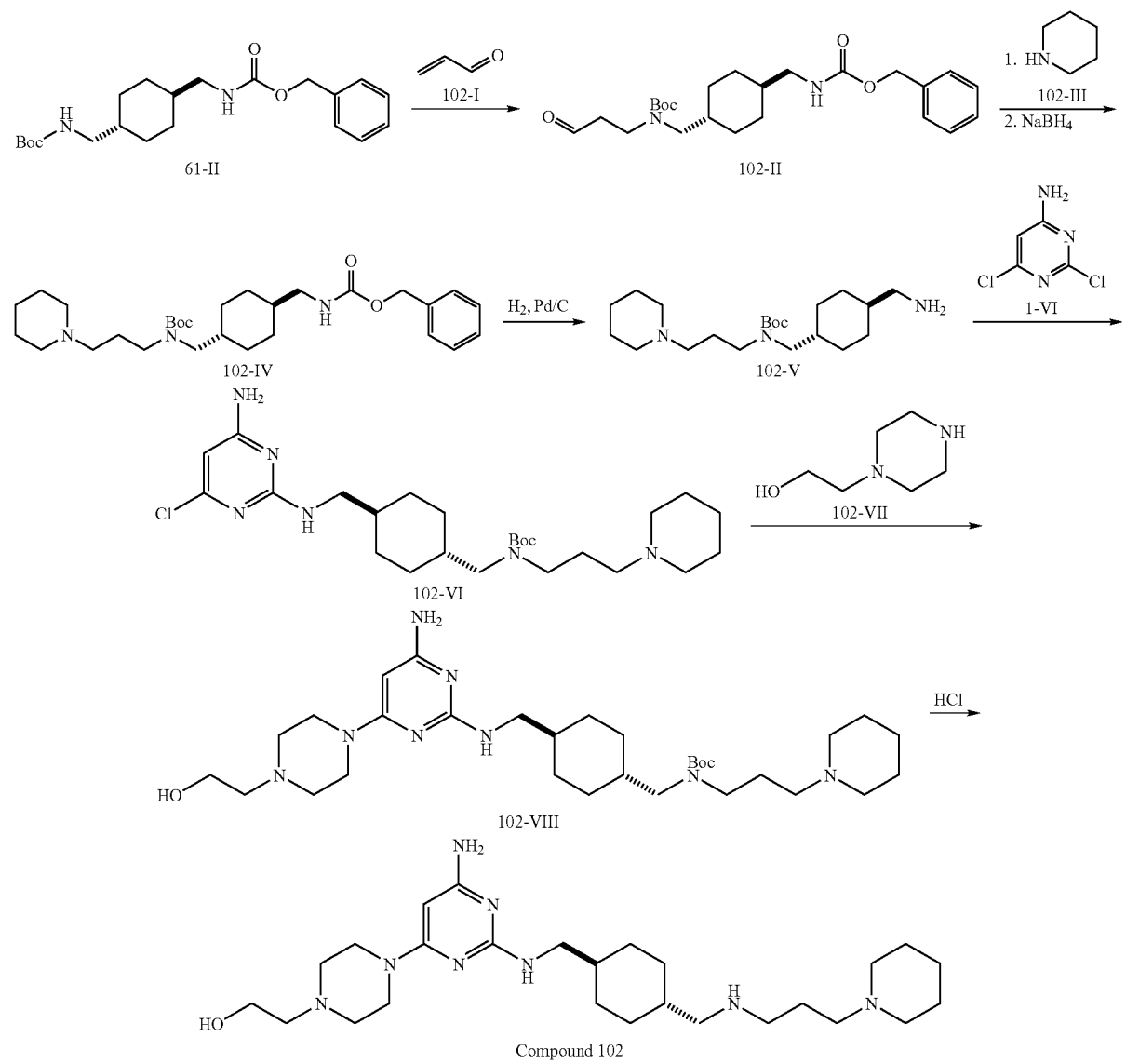

Compound 102

Intermediate 61-II was prepared as described in Example 61.

To intermediate 61-II (1.0 g) and DL-10-camphorsulfonic acid (150 mg) in CH$_2$Cl$_2$ (10 ml) was added acrolein (102-I, 446 mg) at 0° C. The reaction was stirred at 25° C. for 15 hours. The solution was concentrated and purified by chromatography on silica gel (EtOAc/Hex=1:1) to give intermediate 102-II (180 mg) in a 16% yield.

Intermediate 102-II (1.13 g) and piperidine (102-III, 222 mg) were dissolved in MeOH (10 mL). The mixture was stirred in 0° C. for 3 hours. NaBH$_4$ (119 mg) was added under 0° C. and the solution was stirred 1 hour. The solution was concentrated and CH$_2$Cl$_2$ was added. The mixture was washed with solution of saturated NH$_4$Cl (aq) solution. The CH$_2$Cl$_2$ layer was concentrated and the residue was purified by chromatography on silica gel (EtOAc/Hex=1:1) to give intermediate 102-IV (737 mg) in a 56% yield.

102-IV (737 mg) and Pd/C (10%, 20 mg) in MeOH (10 ml) was stirred under H$_2$ (1 atm) for 18 hours. Filtration through a celite column and removal of MeOH afforded intermediate 102-V (580 mg).

A solution of compound 102-V (580 mg) and Et$_3$N (480 mg) in 1-pentanol (10 ml) was reacted with 2,4-dichloro-6-aminopyrimidine (1-VI, 258 mg) at 120° C. for 15 hours. The solution was concentrated and purified by chromatography on silica gel (EtOAc/Hex=1:2) to give intermediate 102-VI (420 mg) in 54% yield.

Compound 102-VI (50 mg) in N-(2-hydroxyethyl)piperazine (102-VII, 1 ml) was stirred at 120° C. for 15 hours. To the mixture was added CH$_2$Cl$_2$ (10 ml) at 25° C. The solution was washed with water. After removed of Cl$_2$CH$_2$, the residue was purified by chromatography on silica gel (Cl$_2$CH$_2$/MeOH=9:1) to give intermediate 102-VIII (15 mg) in a 25% yield.

A solution of HCl in 1,4-dioxane (4N, 2 mL) was added to a solution of intermediate 102-VIII (15 mg) in CH$_2$Cl$_2$ (5.0 mL). The reaction mixture was stirred for 4 hours at room temperature and concentrated by removing the solvent. The resultant residue was washed with ether to afford hydrochloride salt of compound 102 (11 mg).

CI-MS (M$^+$+1): 489.3

Example 103

Preparation of Compound 103

Compound 103 was prepared in the same manner as that described in Example 102 except that 1-(2-morpholinoethyl)-piperazine was used instead of N-(2-hydroxyethyl)piperazine.

CI-MS (M$^+$+1): 558.5

Example 104

Preparation of Compound 104

Compound 104 was prepared in the same manner as that described in Example 102 except that 1-(2-(2-hydroxyethoxy)ethyl)piperazine was used instead of N-(2-hydroxyethyl)piperazine.

CI-MS (M$^+$+1): 533.4

Example 105

Preparation of Compound 105

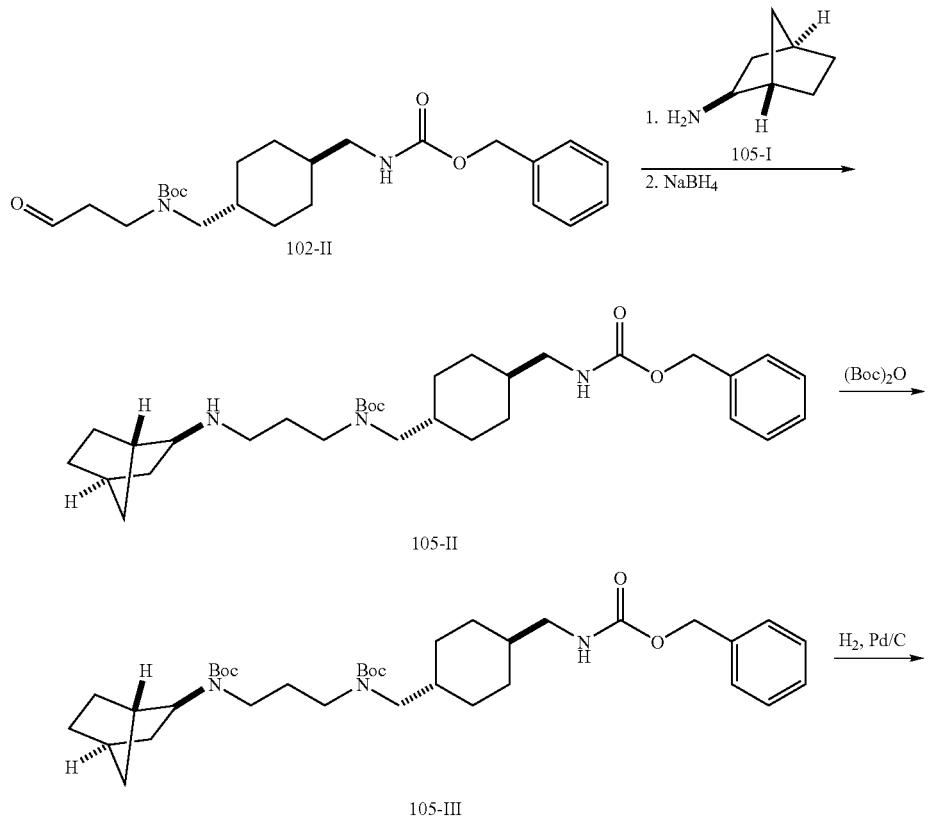

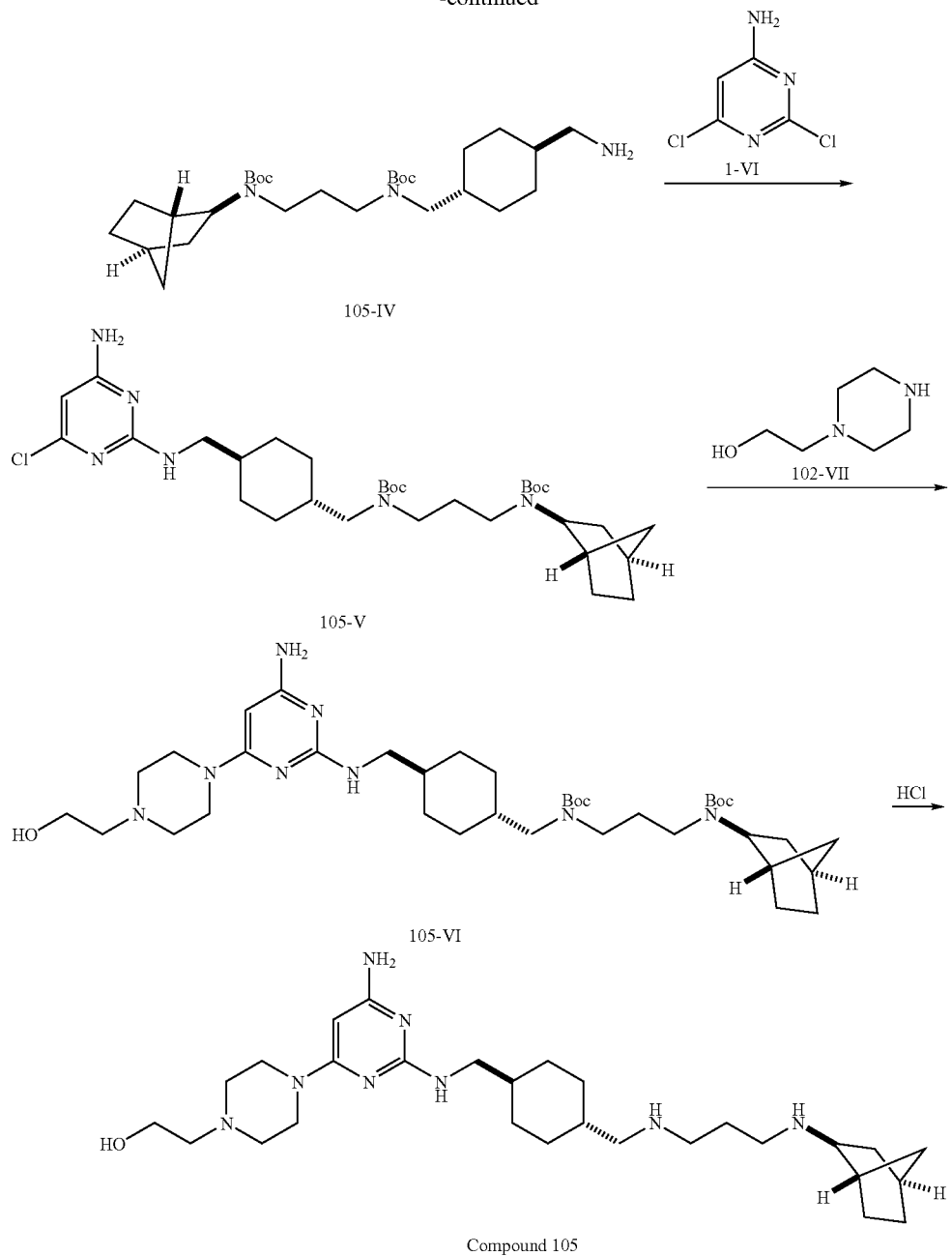

Intermediate 102-II was prepared as described in Example 102.

102-II (1000 mg) and exo-2-aminonorbornane (105-I, 257 mg) in MeOH (10 mL) was stirred at 0° C. for 3 hours. NaBH₄ (87.5 mg) was then added at 0° C. during a period of 1 hour. The solution was concentrated, quenched with NH₄Cl (aq), and extracted with CH₂Cl₂. The organic layers were combined, dried with anhydrous MgSO₄, and concentrated to give a residue, which was purified by chromatography on silica gel (MeOH/28% NH₄OH=97/3) to afford intermediate 105-II (1000 mg, 82% yield).

A solution of intermediate 105-II (1000 mg), Et₃N (210 mg) and Boc₂O (455 mg) in CH₂Cl₂ (10 mL) was stirred at 25° C. for 15 hours. The solution was concentrated and purified by chromatography on silica gel (EtOAcA/Hexane=1/1) to afford intermediate 105-III (907 mg, 76% yield).

A solution of intermediate 105-III (907 mg) and Pd/C (20 mg) in MeOH (10 mL) was stirred under H₂ (balloon) at 25° C. for 18 hours. The filtrate was got by filtration through a celite column and removed MeOH to afford intermediate 105-IV (740 mg).

Et₃N (454 mg) was added to a solution of intermediate 105-IV (740 mg) and 2,4-dichloro-6-aminopyrimidine (1-VI, 246 mg) in 1-pentanol (10 mL). The reaction mixture was stirred at 120° C. for 15 hours and concentrated under vacuum. The resultant residue was purified by chromatography on silica gel (EtOAc/Hexane=1/2) to afford intermediate 105-V (420 mg, 45% yield).

A solution of intermediate 105-V (50 mg) in N-(2-hydroxyethyl)piperazine (1 mL) was stirred at 120° C. for 15 hours. The reaction was cooled to 25° C. and diluted with $Cl_2CH_2$ (10 mL). The reaction solution was washed with water, dried with anhydrous $MgSO_4$, and concentrated. The residue was purified by chromatography on silica gel ($Cl_2CH_2$/MeOH=9/1) to afford intermediate 105-VI (10 mg, 17% yield).

A solution of 4 N HCl in 1,4-dioxane (2 mL) was added to a solution of intermediate 105-VI (10 mg) in $CH_2Cl_2$ (5 mL). The reaction mixture was stirred for 4 hours at room temperature and concentrated by removing the solvent. The resultant residue was washed with ether to afford hydrochloride salt of compound 105 (8 mg).

CI-MS ($M^+$+1): 515.4

Example 106

Preparation of Compound 106

Compound 106 was prepared in a manner the same as that described in Example 105 except that 1-(2-morpholinoethyl)-piperazine was used instead of N-(2-hydroxyethyl)piperazine.

CI-MS ($M^+$+1): 584.5

Example 107

Preparation of Compound 107

Compound 107 was prepared in the same manner as that described in Example 105 except that 1-(2-(2-hydroxyethoxy)ethyl)piperazine was used instead of N-(2-hydroxyethyl)piperazine.

CI-MS ($M^+$+1): 559.5

Example 108

Preparation of Compound 108

Compound 108 was prepared in the same manner as that described in Example 105 except that piperazine was used instead of N-(2-hydroxyethyl)piperazine.

CI-MS ($M^+$+1): 471.4

Example 109

Preparation of Compound 109

Compound 109 was prepared in the same manner as that described in Example 105 except that 1-(2-ethoxyethyl)piperazine was used instead of N-(2-hydroxyethyl)piperazine.

CI-MS ($M^+$+1): 543.1

Example 110

Preparation of Compound 110

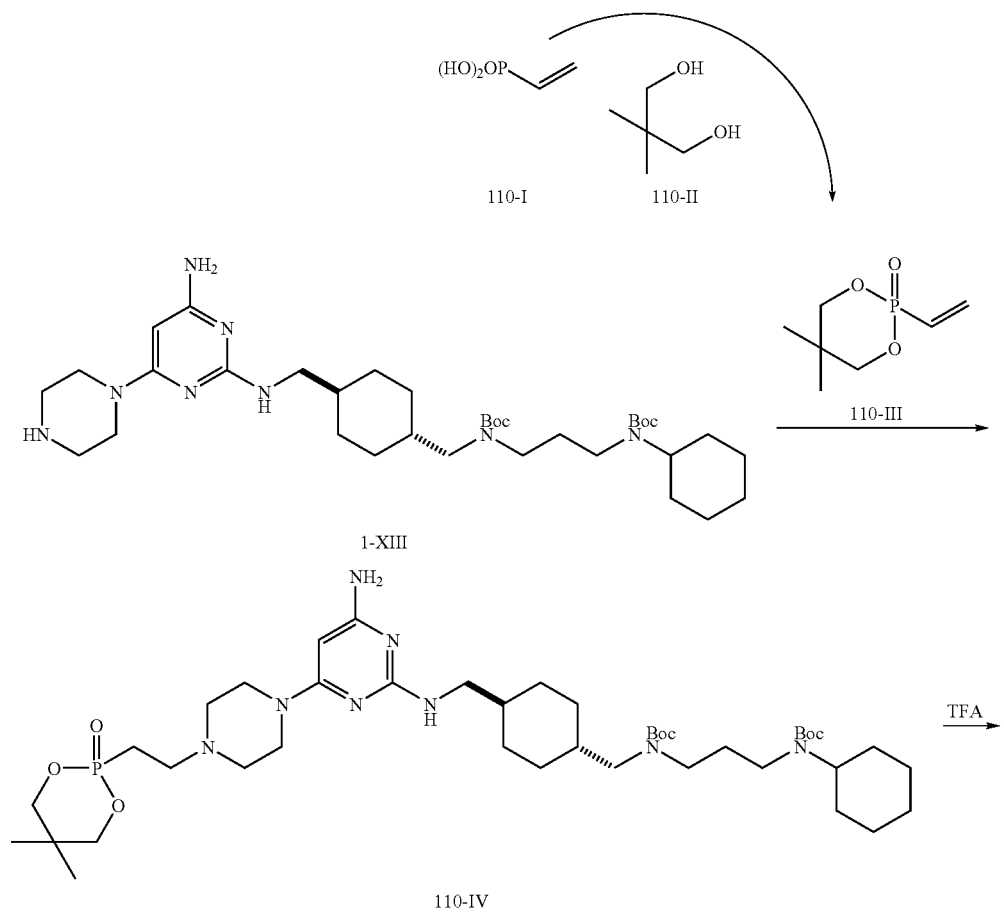

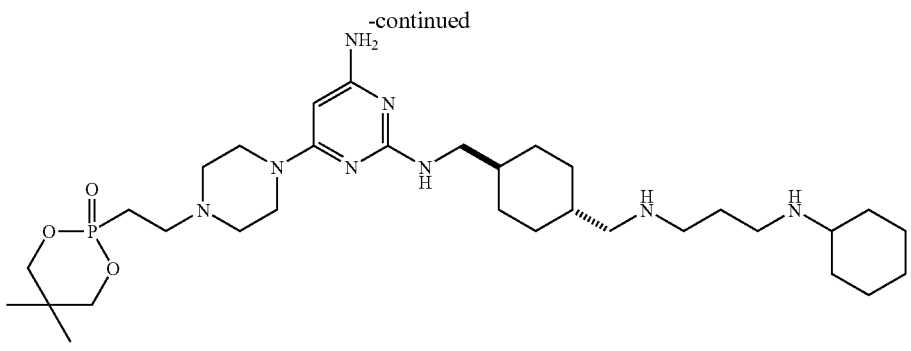

Compound 110

Intermediate 1-XIII was prepared as described in Example 1.

To a solution of vinylphosphonic acid (110-I, 550 mg) in dry CH$_2$Cl$_2$ (17 mL) was slowly added oxalyl chloride (3.9 g) and DMF (0.4 mL) at 0° C. The mixture was refluxed for 3 hours, and concentrated to give quantitatively the corresponding phosphochloridate. The phosphochloridate was added to a mixture of 2,2-dimethyl-1,3-propanediol (110-II, 530 mg), dry CH$_2$Cl$_2$ (17 mL), and Et$_3$N (3.1 g) at −70° C. The mixture was slowly warmed to room temperature and stirred at for 15 hours. It was then washed with water. The organic layer was dried (MgSO$_4$), filtered, and evaporated. The residue was purified by column chromatography on silica gel (EtOAc/MeOH=9:1) to afford 110-III (65 mg, 7% yield) as brown oil.

Compound 110-III (65 mg) was added to a solution of intermediate 1-XIII (202 mg) in MeOH (4 mL). The solution was stirred at 65° C. for 24 hours. The solution was concentrated and the residue was purified by column chromatography on silica gel (CH$_2$Cl$_2$/MeOH=9:1) to afford intermediate 110-IV (147 mg) in a 48% yield.

A solution of 20% TFA/CH$_2$Cl$_2$ (3 mL) was added to a solution of intermediate 110-IV (147 mg) in CH$_2$Cl$_2$ (2.0 mL). The reaction mixture was stirred for 12 hours at room temperature and concentrated to afford trifluoracetic acid salt of compound 110 (267 mg).

CI-MS (M$^+$+1): 635.4

Example 111

Preparation of Compound 111

Compound 111 was prepared in the same manner as that described in Example 110 except that 2-aminobenzyl alcohol was used instead of 2,2-dimethyl-1,3-propanediol.

CI-MS (M$^+$+1): 654.4

Example 112

Preparation of Compound 112

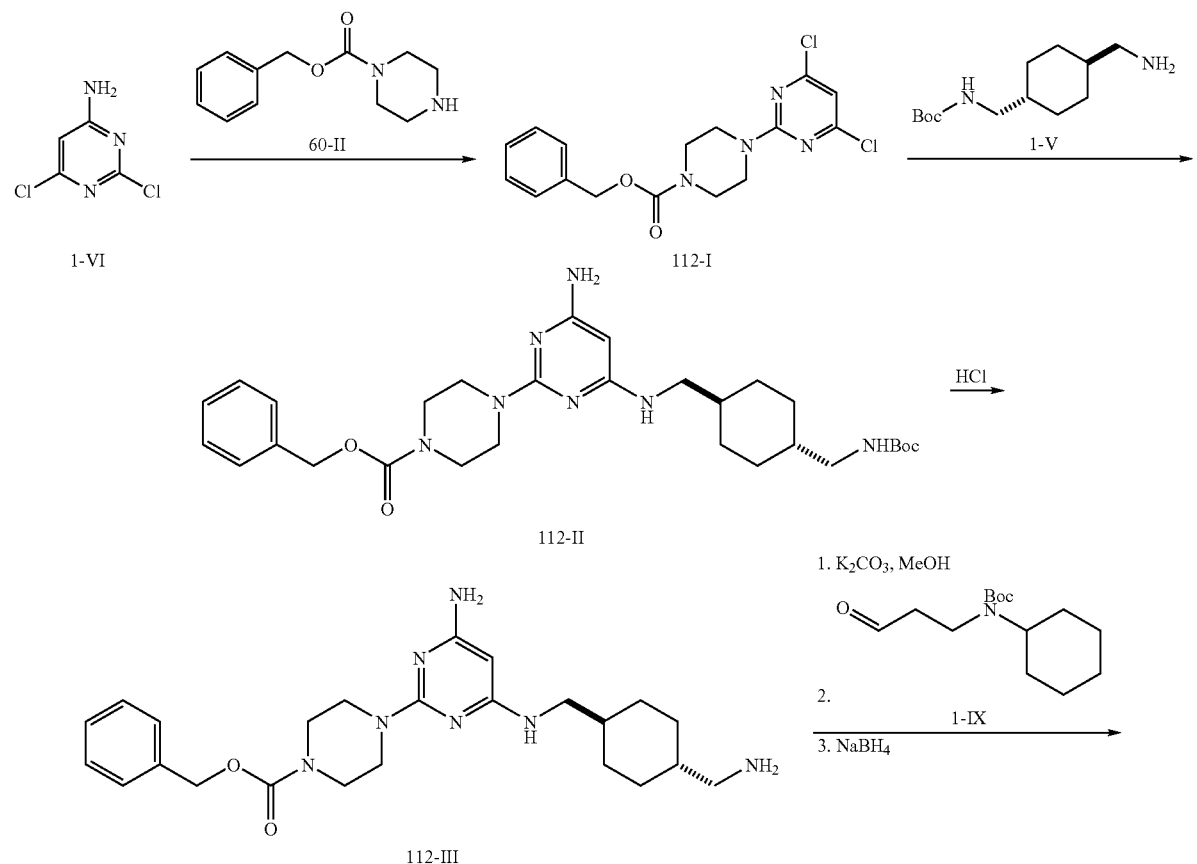

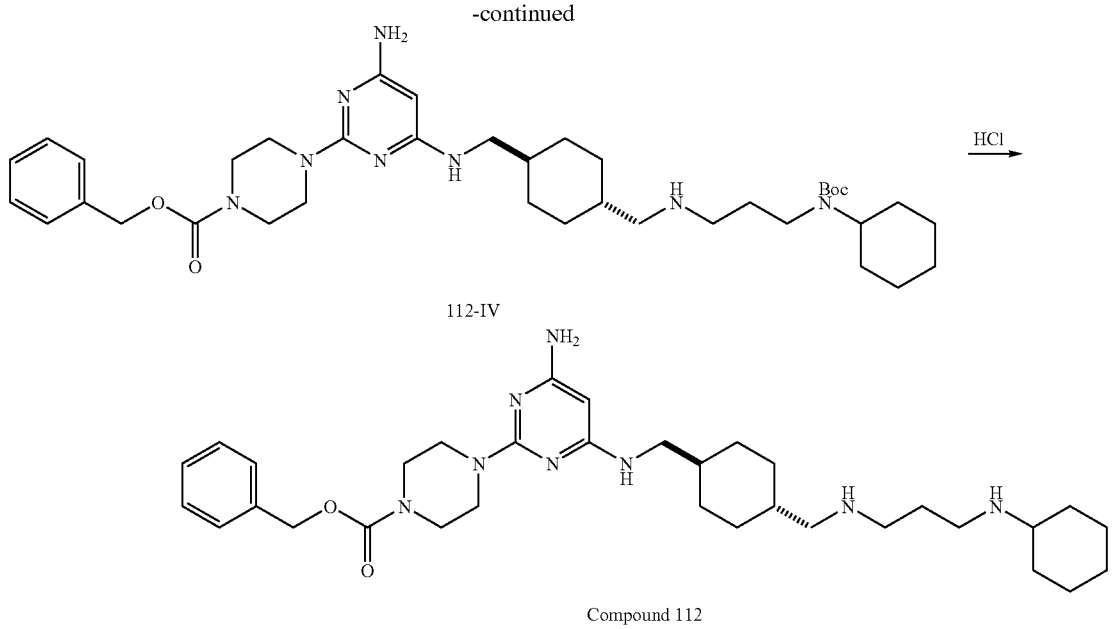

Compound 112

Intermediate 1-V was prepared as described in Example 1.

A solution of compound 60-II (27 g) and Et$_3$N (37 g, 3 eq) in 1-pentanol (80 mL) was reacted with 2,4-dichloro-6-aminopyrimidine (1-VI, 20 g, 1 eq) at 90° C. for 15 hours. TLC showed that the reaction was completed. Ethyl acetate (55 mL) was added at 25° C. The solution was stirred for 1 hour. After Et$_3$NHCl salt was removed, the filtrate was concentrated to 23 mL (⅙ of original volume) at 50° C. Then, diethyl ether (70 mL) was added to the concentrated solution to afford the desired intermediate 112-I (25 g, 60% yield) after filtration at 25° C.

A solution of intermediate 1-V (500 mg, 1.2 eq) and N,N'-diisopropylethyl amine (DIPEA, 446 mg, 2 eq) and KI (29 mg, 0.1 eq) in 1-pentanol (1.8 mL) was reacted with compound 112-I (600 mg) at 140° C. for 24 hours. The reaction mixture was concentrated under reduced pressure. The residue thus obtained was purified by column chromatography on silica gel (MeOH/CH$_2$Cl$_2$=5/95) to afford intermediate 112-II (645 mg) in a 67% yield.

Intermediate 112-II (645 mg) was treated with 4 N HCl/dioxane (1.7 mL) in MeOH (6.5 mL). The mixture was stirred at room temperature overnight. After ether was added, the solution was filtered. The HCl salt of 112-III thus obtained was dried under vacuum. To a solution of HCl salt of 112-III in MeOH (15 mL) was added K$_2$CO$_3$ (1.3 g) at room temperature and stirred for 3 hours (pH>12). The mixture was filtered. Aldehyde 1-IX (300 mg, 1.0 eq based on mole of 112-II) was added to the filtrate of 112-III at 0-10° C. The reaction was stirred at 0-10° C. for 3 hours. TLC showed that the reaction was completed. Then, NaBH$_4$ (70 mg, 1.5 eq based on mole of 112-II) was added at <10° C. The solution was stirred at 10-15° C. for 1 hour and concentrated to provide a residue, which was then treated with CH$_2$Cl$_2$ (30 mL). The mixture was washed with saturated NH$_4$Cl (aq) solution (15 mL). The CH$_2$Cl$_2$ layer was dried over anhydrous MgSO$_4$ and concentrated. The residue was purified by chromatography on silica gel (short column, EtOAc as mobile phase for removing other components; MeOH/28% NH$_4$OH=97/3 as mobile phase for collecting 112-IV) to afford intermediate 112-IV (214 mg) in 30% yield.

A solution of HCl in ether (4 mL) was added to a solution of intermediate 112-IV (200 mg) in CH$_2$Cl$_2$ (1.0 mL). The reaction mixture was stirred for 12 hours at room temperature and concentrated. The resultant residue was washed with ether to afford hydrochloride salt of compound 112 (120 mg).

Cl-MS (M$^+$+1): 593.3

Example 113

Preparation of Compound 113

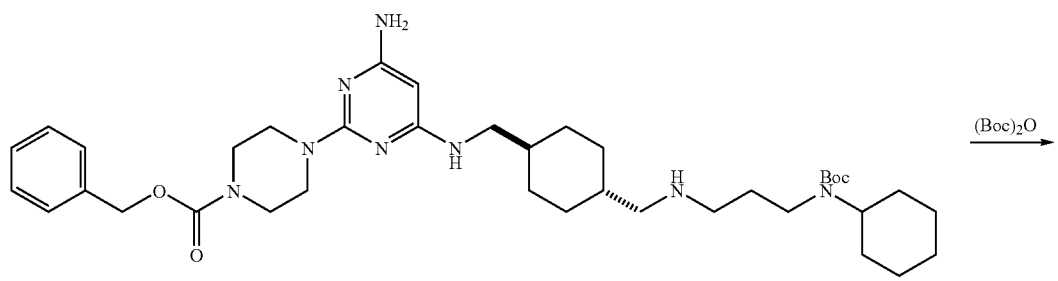

112-IV

-continued

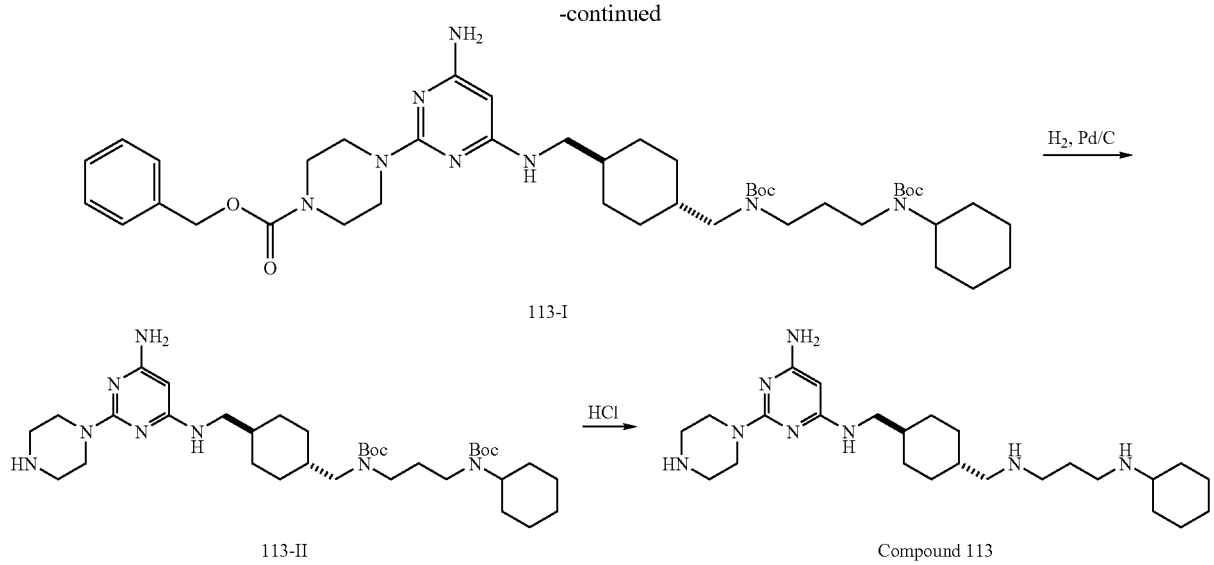

Intermediate 112-IV was prepared as described in Example 112.

Et₃N (65 µL) was added to a solution of intermediate 112-IV (214 mg) and Boc₂O (81 mg) in CH₂Cl₂ (10 mL) at 25° C. The solution was stirred overnight and then concentrated. The resultant residue was purified by column chromatography on silica gel (EtOAc as an eluant) to give intermediate 113-I (196 mg) in a 80% yield.

113-I (150 mg) and Pd/C (10%, 20 mg) in MeOH was stirred under H₂ (balloon) at 25° C. for 18 hours. The mixture was passed through a celite column. Removal of MeOH afforded intermediate 113-II (112 mg) in a 90% yield.

A solution of HCl in ether (2 mL) was added to a solution of intermediate 113-II (100 mg) in CH₂Cl₂ (1.0 mL). The reaction was stirred for 12 hours at room temperature and concentrated. The resultant residue was washed with ether to afford hydrochloride salt of compound 113 (93 mg).

CI-MS (M⁺+1): 459.4

Example 114

Preparation of Compound 114

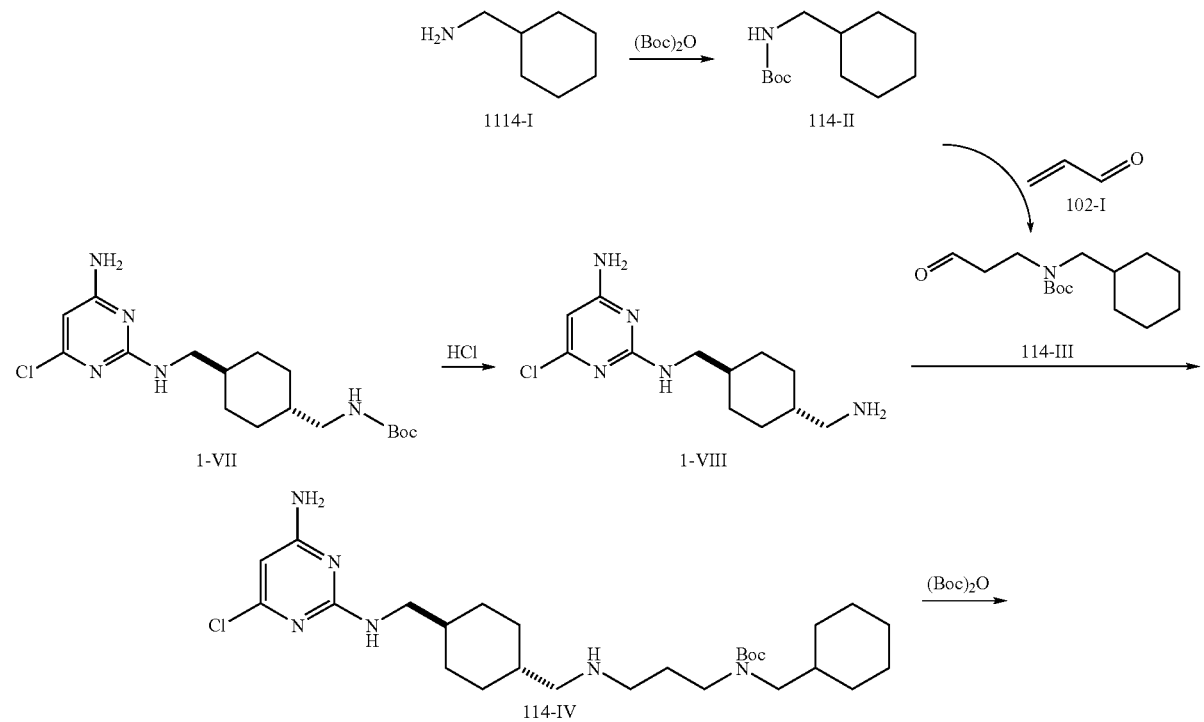

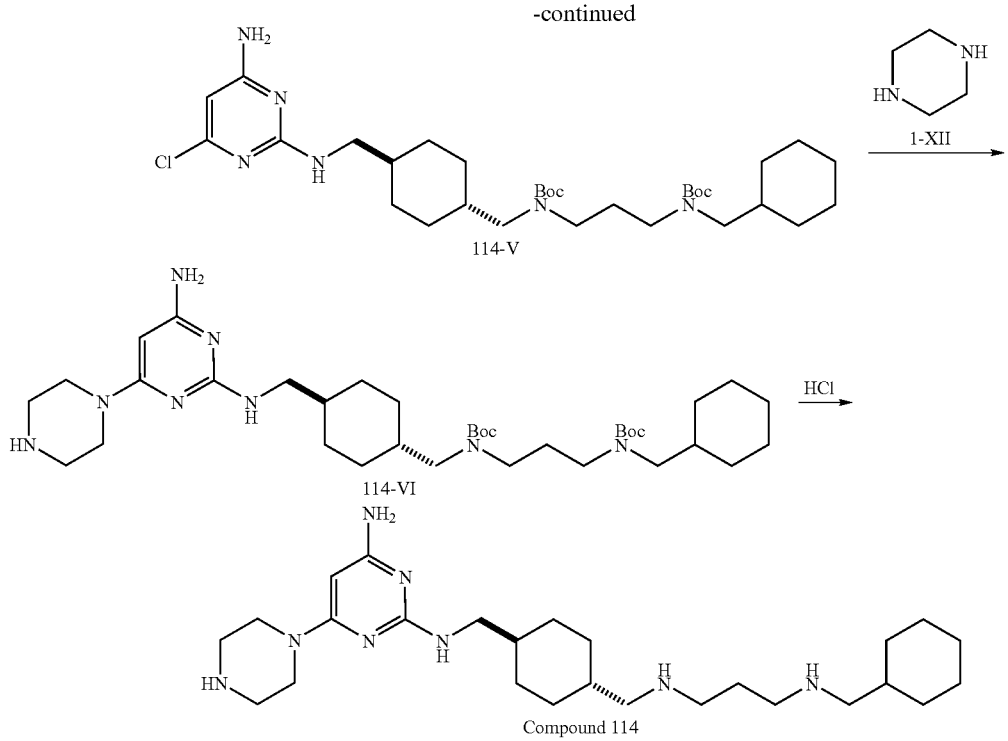

Intermediate 1-VII was prepared as described in Example 1.

A solution of compound cyclohexylmethanamine (114-I, 3.0 g) and Boc₂O (7.7 g) in CH₂Cl₂ (30 mL) was added to Et₃N (5.0 mL) at 25° C. for 15 hours. The solution was then concentrated and the resultant residue was purified by column chromatography on silica gel (using EtOAc and Hexane as an eluant) to give intermediate 114-II (6.5 g) in a 49% yield.

To intermediate 114-I (3.0 g) and DL-10-camphorsulfonic acid (450 mg) in CH₂Cl₂ (30 ml) was added acrolein (102-I, 2.72 g) at 0° C. The reaction was stirred at 25° C. for 15 hours. The solution was concentrated and purified by chromatography on silica gel (EtOAc/Hex=4:1) to give intermediate 114-III (2.4 g) in a 63% yield.

A solution of intermediate 1-VII (1.0 g) was treated with 4 N HCl/dioxane (5 mL) in MeOH (20 mL) and stirred at 25° C. for 15 hours. TLC showed that the reaction was completed. The mixture was concentrated and HCl salt of 1-VIII was formed, filtered, and dried under vacuum (<10 torr). For neutralization, $K_2CO_3$ (1.5 g) was added to the solution of HCl salt of 1-VIII in MeOH (20 mL) at 25° C. The mixture was stirred at the same temperature for 3 hours (pH>12) and filtered.

Aldehyde 114-III (728 mg) was added to the filtrate at 0-10° C. The mixture was stirred at 0-10° C. for 3 hours. TLC showed that the reaction was completed. Then, NaBH₄ (103 mg) was added at less than 10° C. and the solution was stirred at 10-15° C. for 1 h. The solution was concentrated to provide a residue, which was then treated with CH₂Cl₂ (10 mL). The mixture was washed with saturated aq. NH₄Cl solution. The CH₂Cl₂ layer was concentrated and the residue was purified by chromatography on silica gel (short column, EtOAc as mobile phase for removing other components; MeOH/28% NH₄OH=97/3 as mobile phase for collecting 114-IV) to afford crude 114-IV (870 mg).

Et₃N (820 mg) and Boc₂O (470 mg) were added to the solution of 114-IV (870 mg) in CH₂Cl₂ (10 mL) at 25° C. The mixture was stirred at 25° C. for 15 hours. TLC showed that the reaction was completed. The solution was concentrated and purified by chromatography on silica gel (EtOAc/Hex=1:1) to give intermediate 114-V (940 g) in a 91% yield.

To compound 114-V (200 mg) and piperazine (1-XII, 116 mg) in 1-pentanol (2 mL) was added Et₃N (194 mg) at 25° C. The mixture was stirred at 120° C. for 8 hours. TLC showed that the reaction was completed. The solution was concentrated and purified by chromatography on silica gel (EtOAc/MeOH=3:7) to give intermediate 114-VI (120 mg) in a 56% yield.

A solution of intermediate 114-VI (120 mg) was treated with 4 N HCl/dioxane (5 mL) in CH₂Cl₂ (10 mL) and stirred at 25° C. for 15 hours. The mixture was concentrated to give hydrochloride salt of compound 114 (60 mg).

CI-MS (M⁺+1): 473.4

Example 115

Preparation of Compound 115

Compound 115 was prepared in the same manner as that described in Example 114 except that N-(2-hydroxyethyl)piperazine was used instead of piperazine.

CI-MS (M⁺+1): 517.4

Example 116

Preparation of Compound 116

Compound 116 was prepared in the same manner as that described in Example 114 except that 1-(2-ethoxyethyl)piperazine was used instead of piperazine.

CI-MS (M⁺+1): 545.4

Example 117

Preparation of Compound 117

Compound 117 was prepared in the same manner as that described in Example 114 except that 1-(2-morpholinoethyl)-piperazine was used instead of piperazine.
CI-MS (M$^+$+1): 586.5

Example 118

Preparation of Compound 118

Compound 118 was prepared in the same manner as that described in Example 114 except that 2-aminoindan was used instead of cyclohexyl-methanamine.
CI-MS (M$^+$+1): 493.4

Example 119

Preparation of Compound 119

Compound 119 was prepared in the same manner as that described in Example 114 except that 2-aminoindan was used instead of cyclohexyl-methanamine.
CI-MS (M$^+$+1): 537.4

Example 120

Preparation of Compound 120

Compound 120 was prepared in the same manner as that described in Example 116 except that 2-aminoindan was used instead of cyclohexyl-methanamine.
CI-MS (M$^+$+1): 565.4

Example 121

Preparation of Compound 121

Compound 121 was prepared in the same manner as that described in Example 117 except that 2-aminoindan was used instead of cyclohexyl-methanamine.
CI-MS (M$^+$+1): 606.4

Example 122

Preparation of Compound 122

Compound 122 was prepared in the same manner as that described in Example 115 except that aniline was used instead of cyclohexyl-methanamine.
CI-MS (M$^+$+1): 497.0

Example 123

Preparation of Compound 123

Compound 123 was prepared in the same manner as that described in Example 114 except that benzylamine was used instead of cyclohexyl-methanamine.
CI-MS (M$^+$+1): 467.1

Example 124

Preparation of Compound 124

Compound 124 was prepared in the same manner as that described in Example 123 except that N-(2-hydroxyethyl) piperazine was used instead of piperazine.
CI-MS (M$^+$+1): 511.1

Example 125

Preparation of Compound 125

Compound 125 was prepared in the same manner as that described in Example 123 except that 1-(2-ethoxyethyl)piperazine was used instead of piperazine.
CI-MS (M$^+$+1): 539.0

Example 126

Preparation of Compound 126

Compound 126 was prepared in the same manner as that described in Example 123 except that 1-(2-morpholinoethyl)-piperazine was used instead of piperazine.
CI-MS (M$^+$+1): 580.1

Example 127

Preparation of Compound 127

Compound 127 was prepared in the same manner as that described in Example 114 except that cyclopentylamine was used instead of cyclohexylmethanamine.
CI-MS (M$^+$+1): 445.1

Example 128

Preparation of Compound 128

Compound 128 was prepared in the same manner as that described in Example 115 except that cyclopentylamine was used instead of cyclohexylmethanamine.
CI-MS (M$^+$+1): 489.1

Example 129

Preparation of Compound 129

Compound 129 was prepared in the same manner as that described in Example 116 except that cyclopentylamine was used instead of cyclohexylmethanamine.
CI-MS (M$^+$+1): 517.1

Example 130

Preparation of Compound 130

Compound 130 was prepared in the same manner as that described in Example 117 except that cyclopentylamine was used instead of cyclohexylmethanamine.
CI-MS (M$^+$+1): 558.5

Example 131

Preparation of Compound 131

Compound 131 was prepared in the same manner as that described in Example 128 except that 1-(2-(2-hydroxyethoxy)ethyl)piperazine was used instead of N-(2-hydroxyethyl)piperazine.
CI-MS (M$^+$+1): 533.4

Example 132

Preparation of Compound 132

Compound 132 was prepared in the same manner as that described in Example 102 except that pyrrolidine was used instead of piperidine.
CI-MS (M$^+$+1): 475.4

Example 133

Preparation of Compound 133

Compound 133 was prepared in the same manner as that described in Example 114 except that iso-propylamine was used instead of cyclohexylmethanamine.
CI-MS (M$^+$+1): 419.1

Example 134

Preparation of Compound 134

Compound 134 was prepared in the same manner as that described in Example 115 except that iso-propylamine was used instead of cyclohexylmethanamine.
CI-MS (M$^+$+1): 463.1

Example 135

Preparation of Compound 135

Compound 135 was prepared in the same manner as that described in Example 116 except that iso-propylamine was used instead of cyclohexylmethanamine.
CI-MS (M$^+$+1): 491.1

Example 136

Preparation of Compound 136

Compound 136 was prepared in the same manner as that described in Example 117 except that iso-propylamine was used instead of cyclohexylmethanamine.
CI-MS (M$^+$+1): 532.1

Example 137

Preparation of Compound 137

Compound 137 was prepared in the same manner as that described in Example 115 except that thiophene-2-methylamine was used instead of cyclohexylmethanamine.
CI-MS (M$^+$+1): 517.4

Example 138

Preparation of Compound 138

Compound 138 was prepared in the same manner as that described in Example 116 except that thiophene-2-methylamine was used instead of cyclohexylmethanamine.
CI-MS (M$^+$+1): 545.4

Example 139

Preparation of Compound 139

Compound 139 was prepared in the same manner as that described in Example 117 except that thiophene-2-methylamine was used instead of cyclohexylmethanamine.
CI-MS (M$^+$+1): 586.4

Example 140

Preparation of Compound 140

Compound 140 was prepared in the same manner as that described in Example 137 except that 1-(2-(2-hydroxyethoxy)ethyl)piperazine was used instead of N-(2-hydroxyethyl)piperazine.
CI-MS (M$^+$+1): 561.4

Example 141

Preparation of Compound 141

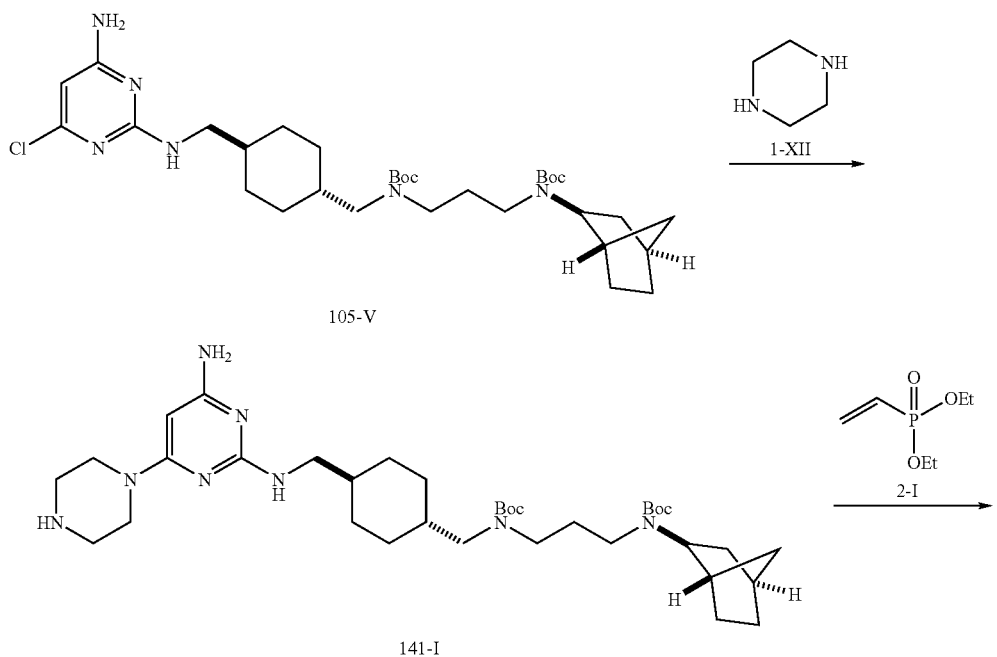

-continued

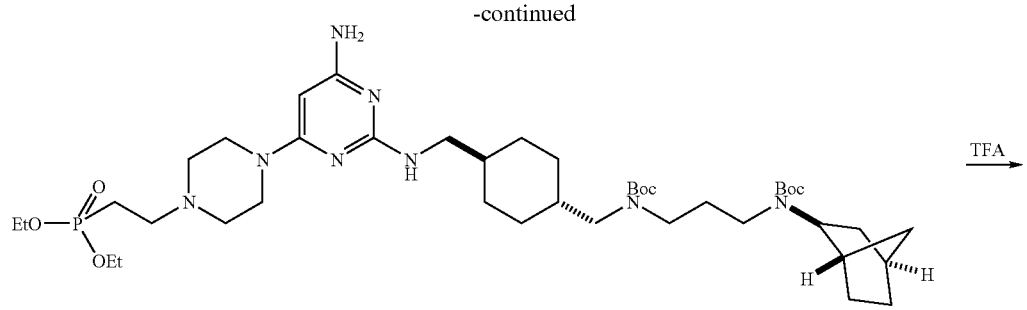

141-II

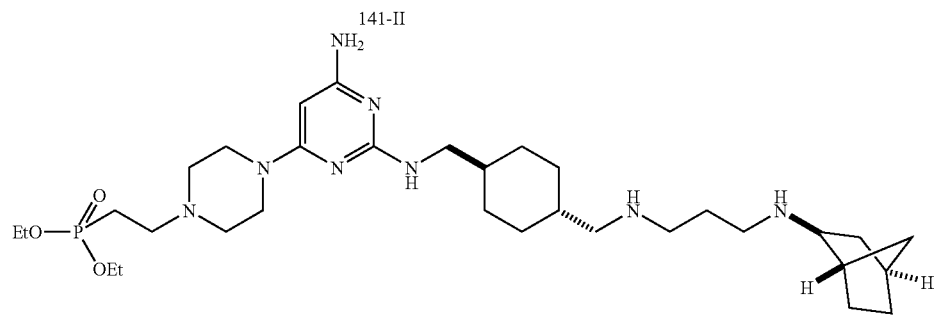

Compound 141

Intermediate 105-V was prepared as described in Example 105.

To compound 105-V (1.7 g) and piperazine (1-XII, 1.4 g, 6 eq) in 1-pentanol (30 mL) was added Et₃N (1.66 g, 6.0 eq) at 25° C. The mixture was stirred at 120° C. for 15 hours. The solution was concentrated and purified by silica gel (EtOAc/MeOH=8:2) to afford 141-I (1.5 g) in a 82% yield.

To a solution of 141-I (1.5 g) in MeOH (30 mL) was added diethyl vinyl phosphonate (2-I, 0.556 g, 1.5 eq) at 25° C. The mixture was stirred under 65° C. for 24 hours. TLC and HPLC showed that the reaction was completed. The solution was concentrated and purified by silica gel (MeOH/CH₂Cl₂=8/92) to get 1.1 g of 141-II in a 59% yield.

TFA (0.2 mL) was added to a solution of intermediate 141-II (100 mg) in CH₂Cl₂ (0.8 mL). The reaction mixture was stirred for 15 hours at room temperature and concentrated by removing the solvent to afford trifluoracetic acid salt of compound 141 (40 mg).

CI-MS (M⁺+1): 635.4

Example 142

Preparation of Compound 142

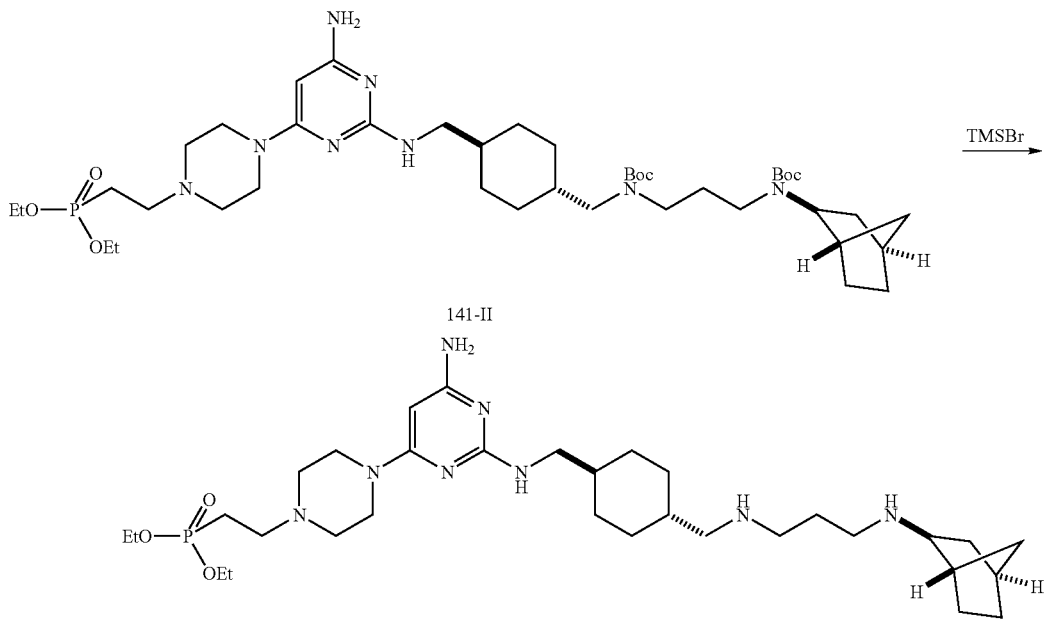

Compound 142

Intermediate 141-II was prepared as described in Example 141.

To a solution of 142-II (1.0 g) in CH$_2$Cl$_2$ (5 mL) was added TMSBr (1.46 g, 8 eq) at 10-15° C. for 1 hour. The mixture was stirred at 25° C. for 15 hours. The solution was concentrated to remove TMSBr and the solvent under vacuum at 40° C. CH$_2$Cl$_2$ was added to the mixture to dissolve the residue. TMSBr and the solvent were removed under vacuum again to obtain a crude solid, which was washed with IPA/MeOH (9/1) to afford compound 142 after filtration and drying at 25° C. under vacuum (<1 torr) for 3 hours. Crystallization in EtOH gave hydrobromide salt of compound 142 (530 mg).
CI-MS (M$^+$+1): 579.4

Example 143

Preparation of Compound 143

Compound 143 was prepared in the same manner as that described in Example 141 except that cyclohexylmethanamine was used instead of exo-2-aminonorborane.
CI-MS (M$^+$+1): 637.5

Example 144

Preparation of Compound 144

Compound 144 was prepared in the same manner as that described in Example 142 except that cyclohexylmethanamine was used instead of exo-2-aminonorborane.
CI-MS (M$^+$+1): 581.4

Example 145

Preparation of Compound 145-I

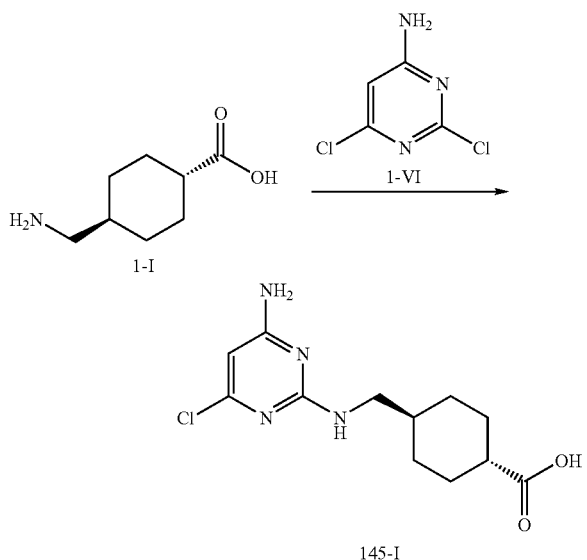

Compound 1-I (2.11 g, 1.1 eq) and K$_2$CO$_3$ (8.5 g, 5 eq) were dissolved in CH$_3$CN/H$_2$O (1:2, 30 mL), and tetra-butyl ammonium iodide was added as a catalyst. The mixture was reacted with 2,4-dichloro-6-aminopyrimidine (1-VI, 2 g, 1 eq.) at 90° C. for 15 hours. The reaction was completed as evidenced TLC. The mixture was evaporated under reduced pressure to remove the organic solvent, and the aqueous layer was acidified with concentrated hydrochloric acid (pH=4~5) and then filtered. The resultant solid was collected, washed three times with water (15 mL), and dried under vacuum to give compound 145-I (2.8 g) as a white solid in 80% yield.
CI-MS (M$^+$+1): 285.1

Example 146

Preparation of Compound 145-V

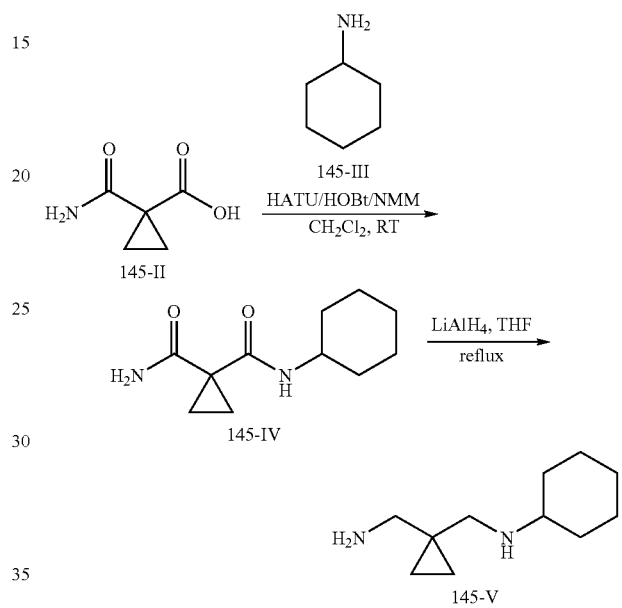

The compound 1-carbamoyl-cyclopropanecarboxylic acid (145-II, 5 g, 1 eq), O-(7-azabenzotriazol-1-yl)-N,N,N'-tetramethyluronium hexa-fluorophosphate (HATU, 22.85 g, 1.6 eq), and 1-hydroxybenzotriazole (HOBt, 8.12 g, 1.6 eq) were suspended in CH$_2$Cl$_2$ (150 mL) at an ice-water bath. N-methylmorpholine (NMM, 16.5 mL, 4 eq) and cyclohexyl amine (145-III, 5.2 mL, 1.2 eq) were added into the solution at 0~10° C. with stirring. After the addition was completed, the reaction mixture was further stirred at room temperature for 15 hours. The reaction was completed as evidenced by TLC.

The mixture was poured into a saturated aqueous NH$_4$Cl (100 mL) solution. After separation, the organic layer was successively washed with brine and saturated aqueous NaHCO$_3$ (100 mL each), dried over anhydrous MgSO$_4$, filtered, and concentrated. The residue was purified by silica gel column chromatography (EtOAc/Hexane=4:1) to afford compound 145-IV (6.3 g) as an orange oil in 80% yield.

Under nitrogen, LiAlH$_4$ (4.8 g, 4 eq) was added in small portions to a solution of 145-IV (6.3 g) in anhydrous THF (150 mL), while the temperature was kept between 0° C. and 10° C. The mixture was stirred at room temperature for 1 hour and then heated with reflux for another 4 hours. The mixture was cooled and quenched with saturated aqueous NH$_4$Cl (15 mL) solution at 0° C. It was allowed to warm up to room temperature and stirred for 1 hour. The mixture was filtered through a pad of celite, and the filtrate was concentrated under reduced pressure to give product 145-V (4.4 g) as a yellow oil in 80% yield.
CI-MS (M$^+$+1): 183.1

Example 147

Preparation of Compound 145

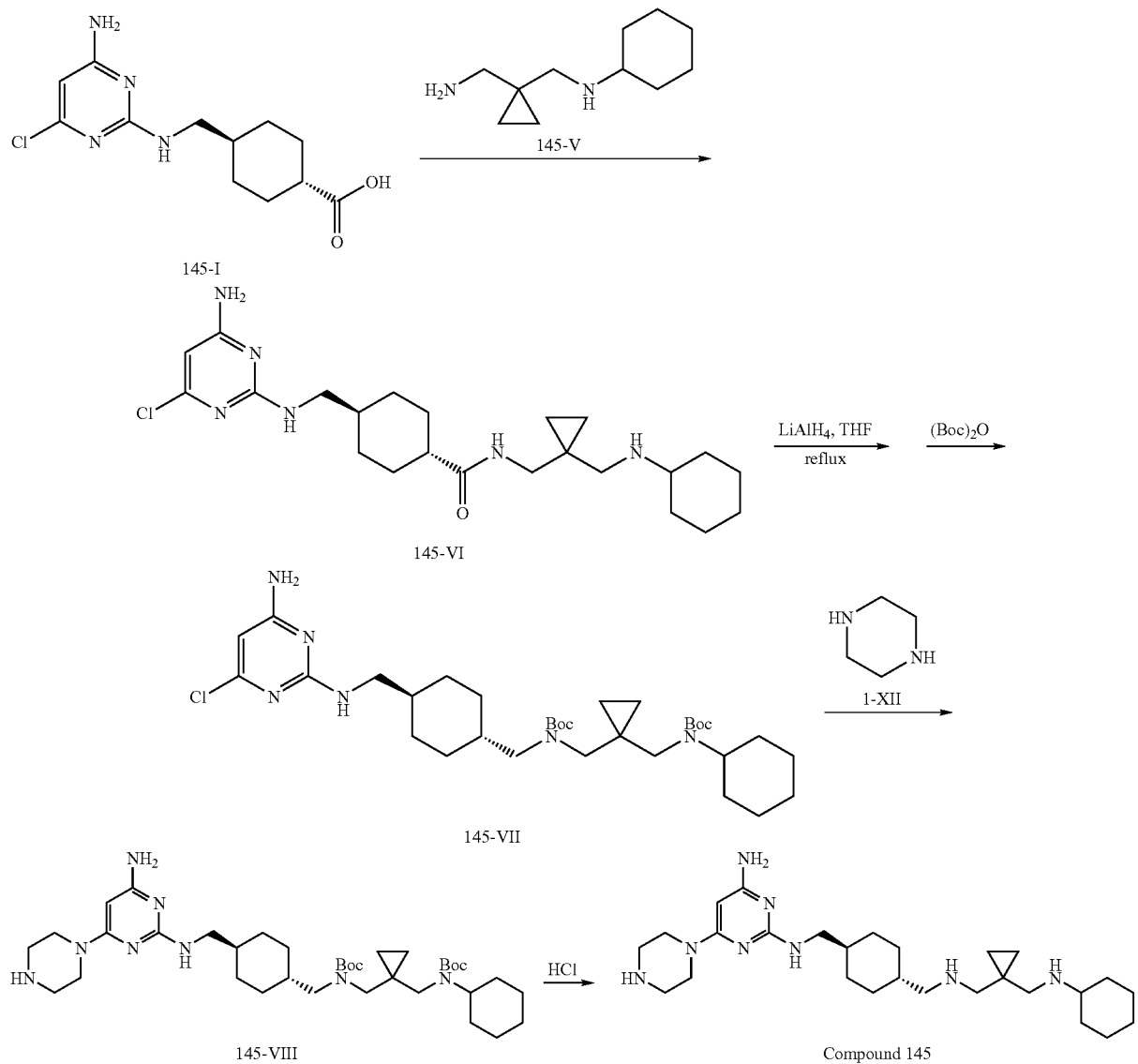

The compound 145-I (3.95 g, 1 eq), HATU (8.44 g, 1.6 eq), and HOBt (3.0 g, 1.6 eq) were suspended in $CH_2Cl_2$ (55 mL) at an ice-water bath. NMM (6.1 mL, 4 eq) and N-(1-(aminomethyl)cyclopropyl)cyclohexanamine (145-V, 3.1 g, 1.2 eq) were added at 0~10° C. with stirring. After the addition was completed, the reaction mixture was further stirred at room temperature for 15 hours. The reaction was completed as evidenced by TLC.

The mixture was poured into a saturated aqueous $NH_4Cl$ (50 mL). After separation, the organic layer was successively washed with brine and saturated aqueous $NaHCO_3$ (50 mL each), dried over anhydrous $MgSO_4$, filtered, and concentrated. The residue was purified by silica gel column chromatography (EtOAc/MeOH=7:3) to afford compound 145-VI (1.5 g) as a yellow oil in 30% yield.

Under nitrogen, $LiAlH_4$ (267 mg, 2 eq) was added in small portions to a solution of 145-VI (1.5 g) in anhydrous THF (20 mL), while the temperature was kept between 0° C. and 10° C. The mixture was stirred at room temperature for 1 hour and then heated with reflux for another 4 hours. It was cooled and quenched with saturated aqueous $NH_4Cl$ (1 mL) solution at 0° C. It was then allowed to warm up to room temperature and stirred for 1 hour. The mixture was filtered through a pad of celite, and then $Et_3N$ (1.0 g, 3 eq) and $(Boc)_2O$ (1.8 g, 2.5 eq) were added to the filtrate at 25° C. After stirred at 25° C. for 15 hours, the solution was concentrated and purified by silica gel column chromatography (EtOAc/Hexane=4:1) to afford compound 145-VII (940 mg) as a yellow oil in 69% yield.

To compound 145-VII (940 mg) and piperazine (1-XII, 382 mg, 3 eq) in 1-pentanol (3 mL) was added $Et_3N$ (450 mg, 3 eq) at 25° C. The mixture was stirred at 120° C. for 8 hours at which time the reaction was completed as evidenced by TLC. Ethyl acetate (5 mL) was added to the reaction mixture at 25° C. The solution was stirred for 1 hour and, after removal of the $Et_3NHCl$ salt by filtration, concentrated and purified by silica gel (EtOAc/MeOH=7:3) to afford 145-VIII (570 mg) in 56% yield.

A solution of intermediate 145-VIII (100 mg) was treated with 4 N HCl/dioxane (2 mL) in CH$_2$Cl$_2$ (1 mL) and stirred at 25° C. for 15 hours. The reaction was completed as evidenced by TLC. The mixture was concentrated to give hydrochloride salt of compound 145 (55 mg).

CI-MS (M$^+$+1): 485.0

Example 148

Preparation of Compound 146

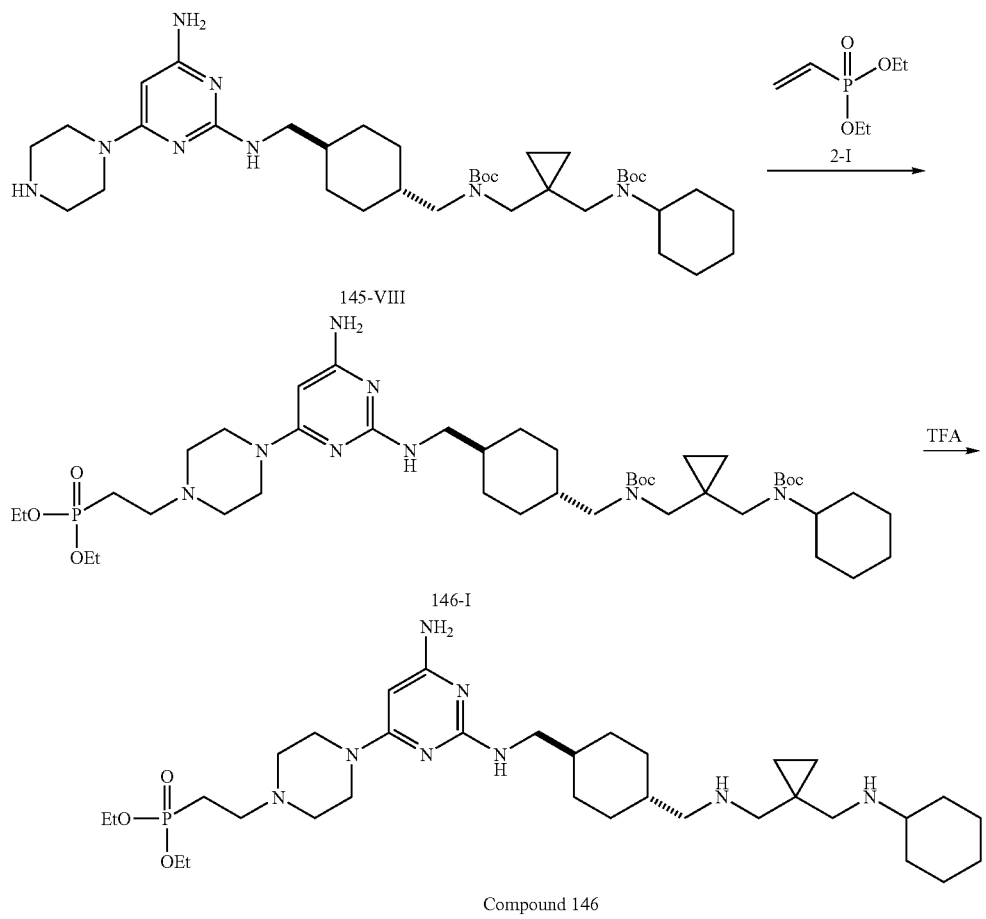

Intermediate 145-VIII was obtained during the preparation of compound 145.

To a solution of 145-VIII (520 mg) in MeOH (8 mL) was added diethyl vinyl phosphonate (2-I, 187 mg, 1.5 eq) at 25° C. The mixture was stirred at 65° C. for 24 hours. The reaction was completed as evidenced by TLC. The solution was concentrated and purified by silica gel (MeOH/CH$_2$Cl$_2$=8/92) to afford compound 146-I (317 mg) as a pale yellow foamy solid in 50% yield.

A solution of 20% TFA/CH$_2$Cl$_2$ (2 mL) was added to a solution of intermediate 146-I (100 mg) in CH$_2$Cl$_2$ (1 mL). The reaction mixture was stirred for 15 hours at room temperature and concentrated by removing the solvent to afford trifluoracetic acid salt of compound 146 (80 mg).

CI-MS (M$^+$+1): 649.3

Example 149

Preparation of Compound 147

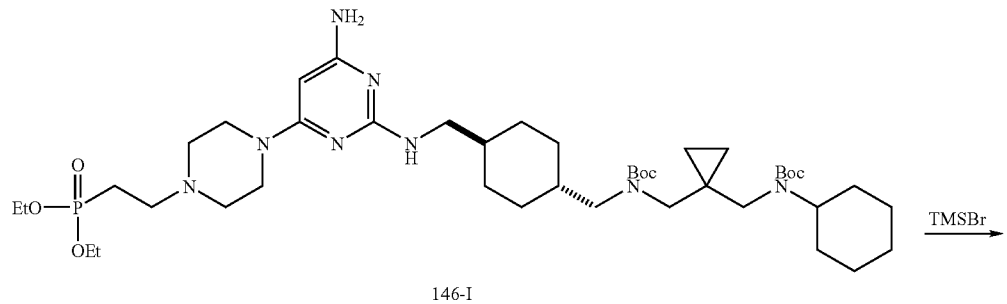

Compound 147

Intermediate 146-I was obtained during the preparation of compound 146.

To a solution of 146-I (200 mg) in CH$_2$Cl$_2$ (1 mL) was added TMSBr (0.3 mL, 8 eq) at 10~15° C. for 1 hour. The mixture was stirred at 25° C. for 15 hours and then concentrated to remove TMSBr and the solvent under vacuum at 40° C. CH$_2$Cl$_2$ was added to dissolve the residue. The mixture was vacuumed again to obtain hydrobromide salt of compound 147 (150 mg).

CI-MS (M$^+$+1): 593.3

Example 150

Preparation of Compound 148

Compound 148 was prepared in the same manner as that described in Example 112 except that 1-(2-morpholinoethyl)-piperazine was used instead of compound 60-II.

CI-MS (M$^+$+1): 572.5

Example 151

Preparation of Compound 149

Compound 149 was prepared in the same manner as that described in Example 112 except that N-(2-hydroxyethyl) piperazine was used instead of compound 60-II.

CI-MS (M$^+$+1): 503.4

Example 152

Preparation of Compound 150

Compound 150 was prepared in the same manner as that described in Example 112 except that 1-(2-(2-hydroxyethoxy)ethyl)piperazine was used instead of compound 60-II.

CI-MS (M$^+$+1): 547.4

Example 153

GTP-Binding Assay

Compounds 1-150 were tested for their efficacy in binding to the CXCR4 receptor using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonist. Eu-GTP, a non-hydrolysable analogue of GTP, is used to monitor agonist-dependent activation of G-protein. Note that stimulation of CXCR4 receptor by SDF-1 leads to replacement of GDP by GTP on the α-subunit of G-protein. The resultant GTP-Gα complex represents the activated form of G-protein. See Peltonen et al., Eur. J. Pharmacol. (1998) 355:275.

Plasma membrane derived from CXCR4-expressing HEK293 cells was suspended in an assay buffer (50 mM NaCl, 100 mg/mL saponin, 3 mM MgCl$_2$, 3 mM GDP, 5% BSA, 50 mM HEPES, pH 7.4). An aliquot (4 μg protein) was added to each well of an AcroPlate (Pall Life Sciences, Ann Arbor, Mich.). After addition of test compounds (10 mM in 0.1% DMSO) and SDF-1 (4 nM in the assay buffer), the assay plate was incubated in the dark at room temperature with slow shaking for 10 minutes. Eu-GTP, obtained from Wallac Oy Eu-GTP, was added to each well. The plate was incubated again for 60 minutes and then washed twice with a wash solution provided in the assay kit to terminate the assay. Binding of Eu-GTP was determined based on the fluorescence signal detected by a Victor 2 multi-label reader.

Unexpectedly, 28 test compounds showed IC$_{50}$ (concentration required to inhibit SDF-1 stimulated GTP-Gα binding by 50%) at 20 nM, 83 test compounds showed IC$_{50}$ between at nM, 37 test compounds showed IC$_{50}$ at 100-1000 nM.

Example 154

Radioligand Binding Assay

Binding competition between each of 114 test compounds and human SDF-1 was determined using glass fiber filter plates (Millipore, Billerica, Mass.) as follows:

The glass fiber filter plates were pre-coated with 90 μl of 0.2% polyethyleneimine for 30 minutes and rinsed with 100 μl of distilled water for four times to reduce non-specific binding. Membranes of human CXCR4-transfected HEK293 cells (5-10 μg protein/well) in 70 μl of assay buffer (50 mM HEPES, pH 7.4, 0.5% bovine serum albumin, 90 mM NaCl, 5 mM MgCl$_2$, 1 mM CaCl$_2$) were incubated with 20 μl of a test compound and 10 μl of [$^{125}$I]-SDF-1 (final concentration 150 pM) in U-bottom assay plates (Corning, Corning, N.Y.). After 120 minutes at room temperature, the incubation was terminated by transferring the reaction mixture to glass fiber plate wells (80 μl/well) and filtered by vacuum filtration (MultiScreen Vacuum Maniford, Millipore). The plate was washed 4 times with 80 μl/well of wash buffer (20 mM HEPES, pH 7.4 and 90 mM NaCl) and then air dried overnight. After 35 μl of a Supermix cocktail was added to each well of plate, the radioactivity retained on the plate was counted with Trilux MicroBeta (PerkinElmer, Boston, Mass.).

50 test compounds showed IC$_{50}$ (concentration required to inhibit binding of [$^{125}$I]-SDF-1 to the receptor by 50%) at less than 20 nM, 43 test compounds showed IC$_{50}$ at 20-100 nM, and 21 test compounds showed IC$_{50}$ at 100-1000 nM.

Example 155

Stem Cell Mobilization

The efficacy of five compounds in enhancing stem cell mobilization was tested as follows:

Each compound was dissolved in saline. The solutions were each administered to BALB/c mice intravenously at 4 ml/kg. Whole blood was collected 1, 2, 3, 6, 18, and 24 hours after intravenous injection by cardiac puncture. Mice receiving saline were used as control. Blood samples of the same group (N=3 in each group) were pooled and total leukocyte numbers were counted using trypan blue exclusion. Hematopoietic stem cells ($CD34^+$) and endothelial progenitor cells ($CD133^+$) were measured using antibody surface staining and flow cytometry (Beckman Coulter, Miami, Fla.). Statistical significance was determined using a one-way ANOVA. Differences were considered significant if P values were <0.05.

The results indicated that all of the test compounds enhanced mobilization of $CD34^+$ hematopoietic stem cells and $CD133^+$ endothelial progenitor cells into peripheral blood in a dose-dependent manner. Within 1-3 hours after a single injection, the compounds increased circulating $CD34^+$ cells up to 6.2-14.5 folds and $CD133^+$ cells up to 5.2-10.7 folds.

Example 156

Synergistic Effect in Mobilization of Stem Cells and Endothelial Progenitor Cells The efficacy of G-CSF alone and a combination of G-CSF and a test compound in mobilizing stem cells and endothelial progenitor cells was also tested in a manner similar to that described in Example 155. The results indicate that the combination exerted synergistic effect in enhancing $CD34^+$ and $CD133^+$ mobilization. Circulating $CD34^+$ was increased to up to about 18.5 folds and circulating $CD133^+$ up to about 64.2 folds.

Example 157

Oxygen-Induced Retinopathy (Diabetic Retinopathy Model)

Newborn rats were placed under air containing 50% oxygen and air containing 10% oxygen alternately in a cycle of 24 hours from birth through 14 days to induce robust retinal angiogenesis. These rats were used as a diabete retinopathy model.

A test compound was dissolved in water. The solutions at the concentrations of 0.1-10 µM were administered to the rats via intravitreal injection (2 µl/eye). Oxygen-induced retinopathy rats without injection of any test compound or injected with vehicle were used as control. All of the rats were then placed under normal air for six days before sacrifice. Neovascularization was assessed using ADPase histochemistry and computer-assisted image analysis techniques.

The results indicate that the test compound effectively inhibited retinal neovascularization.

Example 158

Choroidal Neovascularization (Age-Related Macular Degeneration Model)

Choroidal neovascularization (CNV) was generated by laser-induced rupture of Bruch's membrane in 4- to 6-week-old, male C57BL/6J mice. With a hand-held cover slide as a contact lens, an argon laser photocoagulator (532 nm) mounted on a slit-lamp was used to create four lesions centered around the optic nerve head in the retinal mid-periphery (50 µm spot size, 0.07 sec duration, 260 mW). A test compound was dissolved in water. The solutions at the concentrations of 1 to 100 µM were administered to the CNV mice via intravitreal injection (1 or 2 µl/eye) immediately following laser treatment. CNV mice without treatment of test compounds were used as a control. Fourteen days after the laser treatment, all of the mice were sacrificed and CNV growth at the Bruch's membrane rupture sites was assessed using fluorescently stained choroid-sclera-RPE flat-mounts via computer-assisted image analysis.

The results indicate that the test compound reduced the neovascularization area by 34%-59%, compared with control.

Example 159

Limb Ischemia Model

The efficacy of three compounds in treating ischemia was tested using a limb ischemia model.

Ischemia was induced in the left hindlimb of each BALB/c mouse as follows: The femoral artery was ligated and transected in two places of 0.20-0.30 cm length proximal and distal to the ligature. Any other large blood vessels that were visible and distal to the ligature were also transected.

Each compound was dissolved in saline and administrated intravenously to the limb ischemia mice on day 4 and day 8 post-surgery at the dosage ranging from 0.5 mg/kg to the maximum tolerated dose. The contralateral right hindlimbs and mice receiving saline were used as a control. The animals were observed using two semiquantitative ischemia indexes three times each week. The extent of blood-flow restoration was measured on days 1, 7, 14, 21, and 28 post-surgery using a laser Doppler imager (PeriScan PIM II), which detects the flux (blood/(area×time)) of blood. In addition, the muscle strength was measured using a Digital Grip Strength Meter (0167-005 L, Columbus Instruments). New vessel formation in leg muscles collected immediately after sacrifice on day 18 post-surgery was assessed. For capillary density analysis, CD31 immunohistochemistry staining was performed. Positive stained newly-formed endothelial cells in 10 fields were counted under microscopy, and the data presented as positive cells/per high power field. Statistical significance was determined using one-way ANOVA. Differences were considered significant if P values were <0.05.

All of the test compounds exhibited efficacy in improving hindlimb function, appearance, and muscle strength, restoring blood flow, and increasing formation of new vessel.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of the following formula:

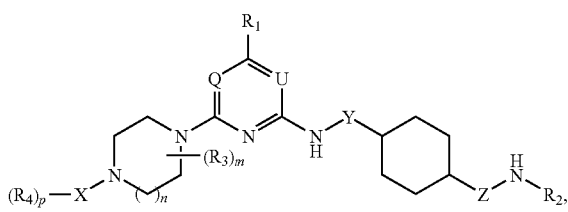

wherein
- each Q and U is CH or N, provided that one of Q and U is N;
- each of X, Y, and Z, independently, is $C_{1-5}$ alkylene or deleted;
- m is 0, 1, 2, 3, 4, or 5;
- n is 1;
- p is 1 or 2;
- $R_1$ is H, $C_1$-$C_{10}$ alkyl, $C_3$-$C_{20}$ cycloalkyl, $C_1$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$;
- $R_2$ is $C_1$-$C_{10}$ alkyl, $C_3$-$C_{20}$ cycloalkyl, $C_1$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_1$-$C_{20}$ heterocycloalkyl, or $N(R_cR_d)$;
- $R_3$, independently, is $C_1$-$C_{10}$ alkyl, $C_3$-$C_{20}$ cycloalkyl, $C_1$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $R_3$ is $C_{1-5}$ alkylene bonded to two carbon atoms of the ring to which it is attached or $C_{2-8}$ alkylene bonded to one carbon atom of the ring to which it is attached; and
- $R_4$ is $P(=O)(OR_g)(OR_i)$, $P(=O)(NHR_g)(OR_i)$, $P(=O)(NR_g)(NR_i)$, $S(=O)_2OR_g$, or $S(=O)_2R_g$;
- in which each of $R_a$, $R_b$, $R_c$, $R_d$, $R_e$, $R_f$, $R_g$ and $R_i$, independently, is H, $C_1$-$C_{10}$ alkyl, $C_3$-$C_{20}$ cycloalkyl, $C_1$-$C_{20}$ heterocycloalkyl, aryl, heteroaryl, or —C(O)R, R being H, $C_1$-$C_{10}$ alkyl, $C_3$-$C_{20}$ cycloalkyl, $C_1$-$C_{20}$ heterocycloalkyl, aryl, or heteroaryl; or $R_a$ and $R_b$ are linked and together form $C_{2-8}$ alkylene, $R_c$ and $R_d$ are linked and together form $C_{2-8}$ alkylene, $R_e$ and $R_f$ are linked and together form $C_{2-8}$ alkylene, or $R_g$ and $R_i$ are linked and together form $C_{1-5}$ alkylene.

2. The compound of claim 1, wherein Q is CH and U is N.

3. The compound of claim 1, wherein X is —CH$_2$—, —CH$_2$CH$_2$— or —CH$_2$CH$_2$CH$_2$— and p is 1.

4. The compound of claim 1, wherein Y is —CH$_2$ or deleted and Z is —CH$_2$—.

5. The compound of claim 1, wherein $R_2$ is $C_{1-5}$ alkyl substituted $N(R_cR_d)$.

6. The compound of claim 5, wherein $R_2$ is —CH$_2$CH$_2$CH$_2$—N(R$_c$R$_d$), in which $R_c$ is H and $R_d$ is $C_1$-$C_{10}$ alkyl, $C_3$-$C_{20}$ cycloalkyl, $C_1$-$C_{20}$ heterocycloalkyl, aryl, or heteroaryl, or $R_c$ and $R_d$ are linked and together form $C_{4-6}$ alkylene.

7. The compound of claim 1, wherein m is 0, 1, or 2; $R_1$ is NH$_2$; and $R_3$ is $C_1$-$C_3$ alkyl, $C_3$-$C_8$ cycloalkyl, $C_1$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached.

8. The compound of claim 1, wherein $R_4$ is $P(=O)(OH)_2$, $P(=O)(OH)(OCH_2CH_3)$, $P(=O)(OCH_2CH_3)_2$,

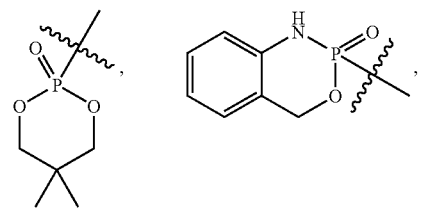

$S(=O)_2OH$, $S(=O)_2CH_3$, or $S(=O)_2Ph$.

9. The compound of claim 8, wherein m is 0, 1, or 2; p is 1; X is —CH$_2$CH$_2$— or —CH$_2$CH$_2$CH$_2$—; Y is —CH$_2$ or deleted and Z is —CH$_2$—; $R_1$ is NH$_2$; $R_2$ is $C_{1-5}$ alkyl substituted $N(R_cR_d)$; and $R_3$ is $C_1$-$C_3$ alkyl, $C_3$-$C_8$ cycloalkyl, $C_1$-$C_8$ ttbonded to two carbon atoms of the ring to which it is attached or $C_{2-5}$ alkylene bonded to one carbon atom of the ring to which it is attached.

10. The compound of claim 1, wherein the compound is selected from the groups consisting of the following compounds:

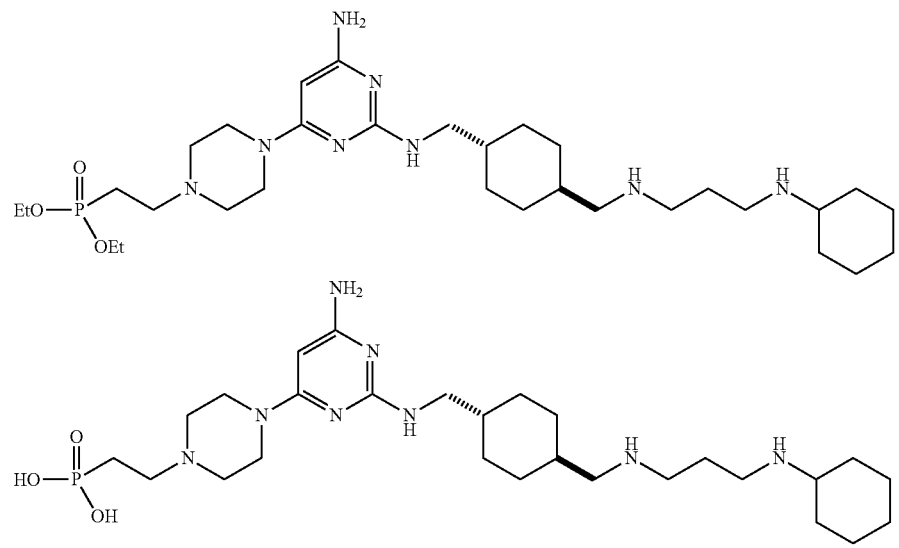

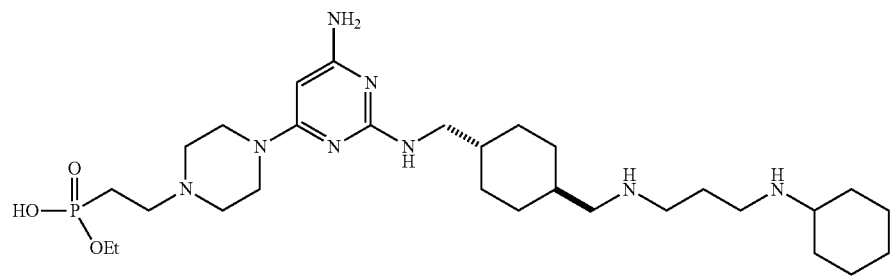
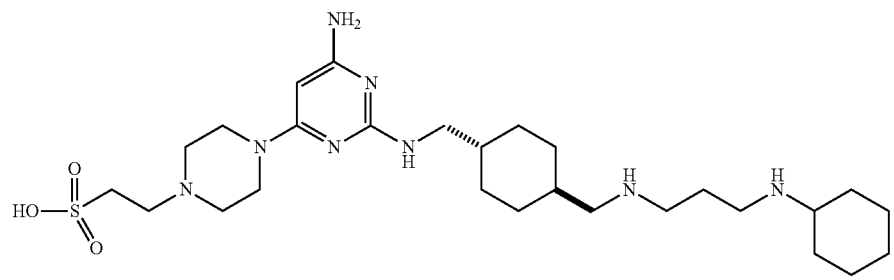
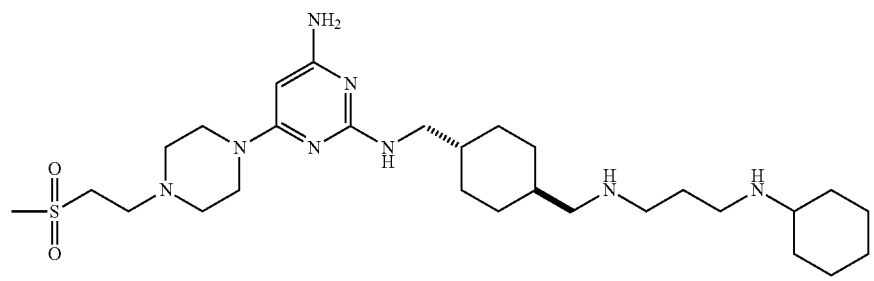
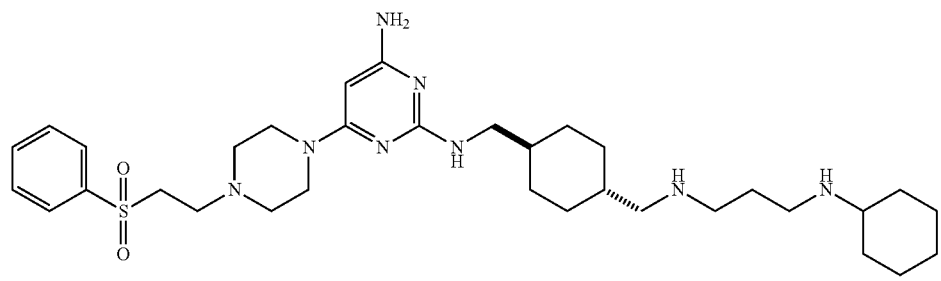
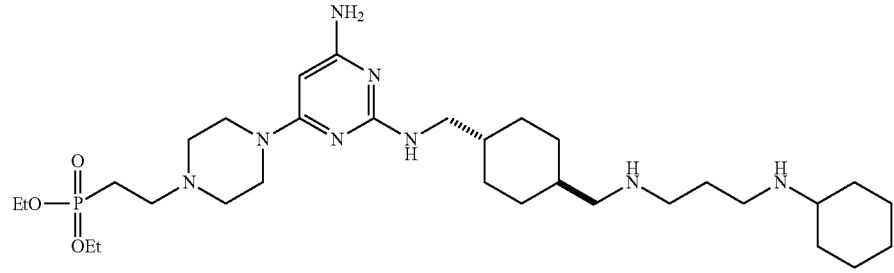
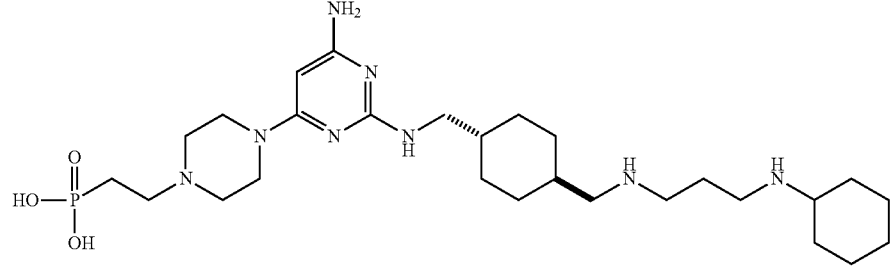

-continued
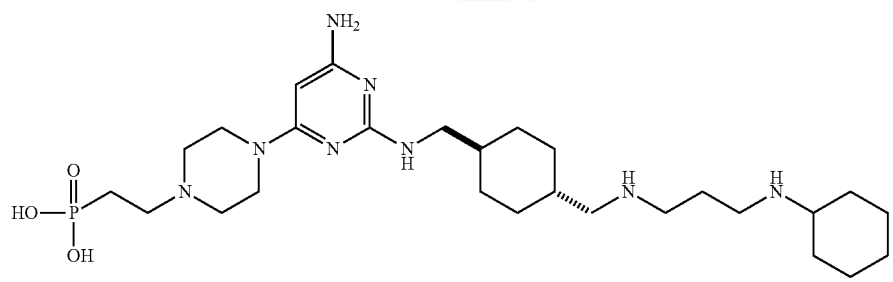
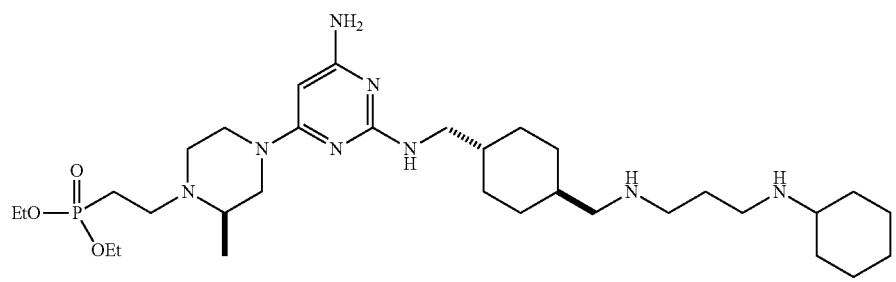
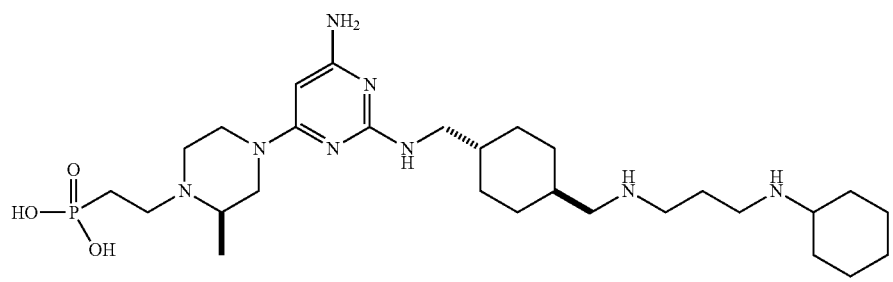
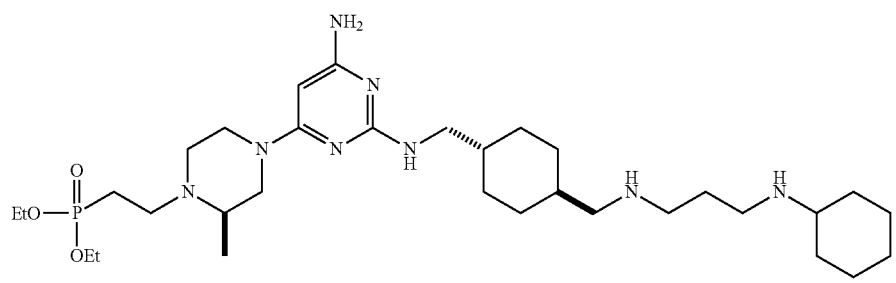
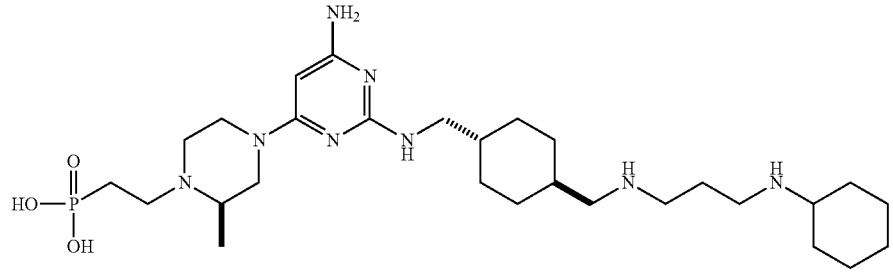
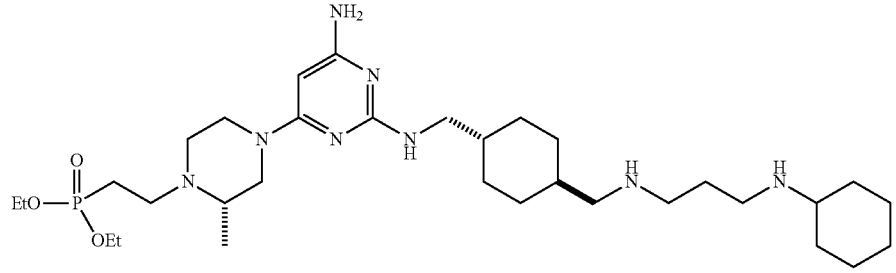

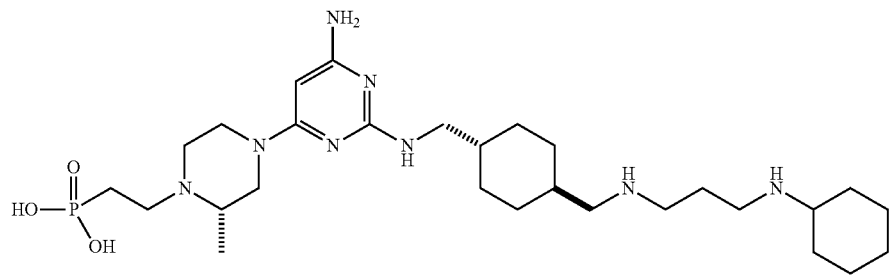
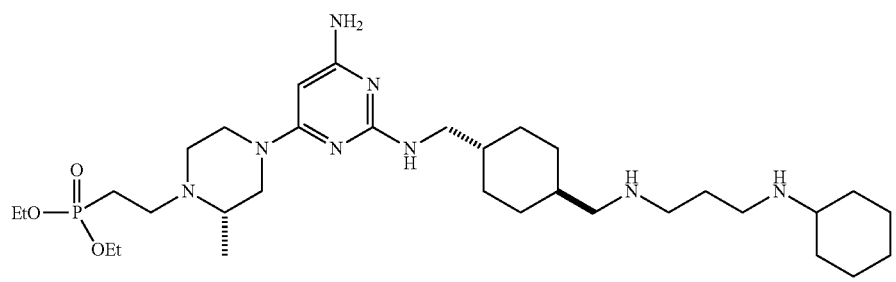
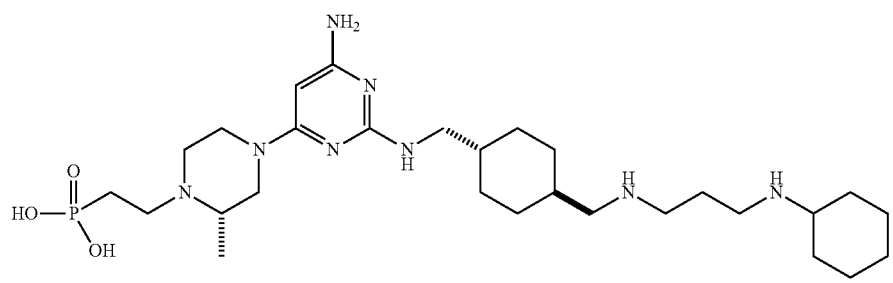
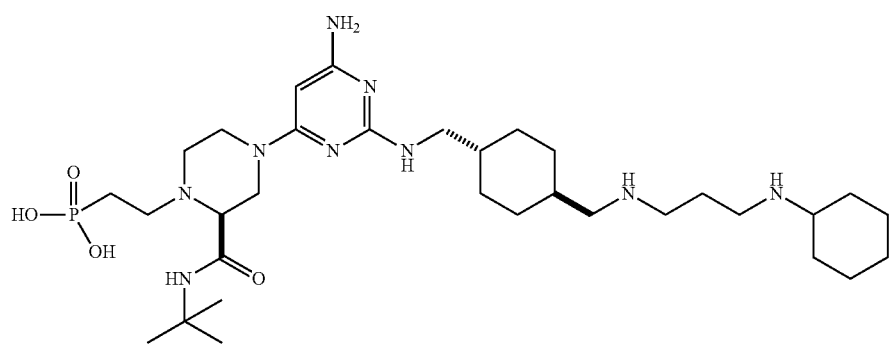
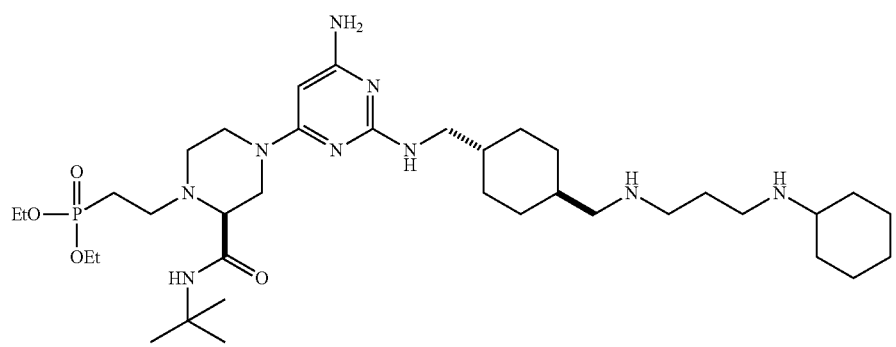

-continued
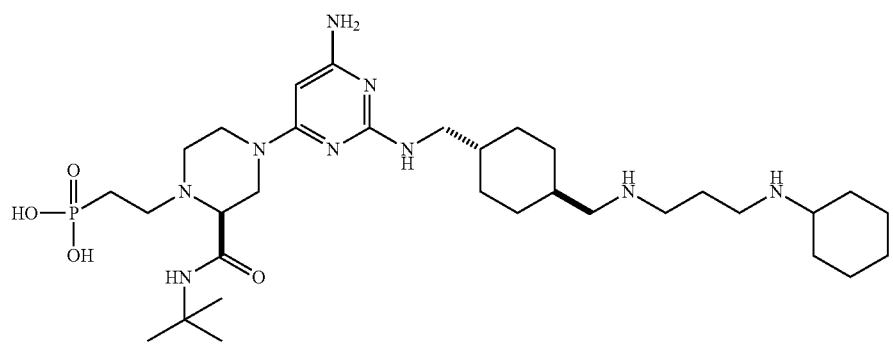
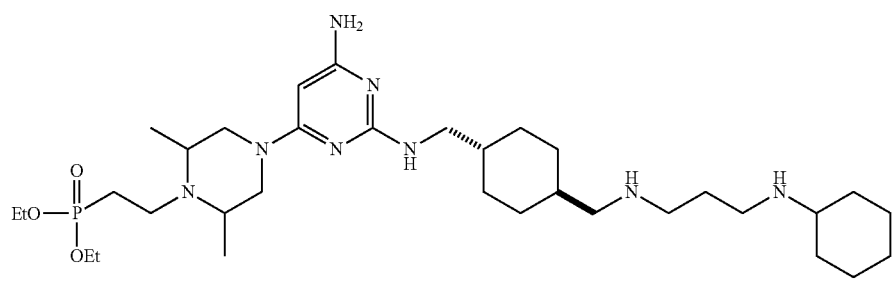
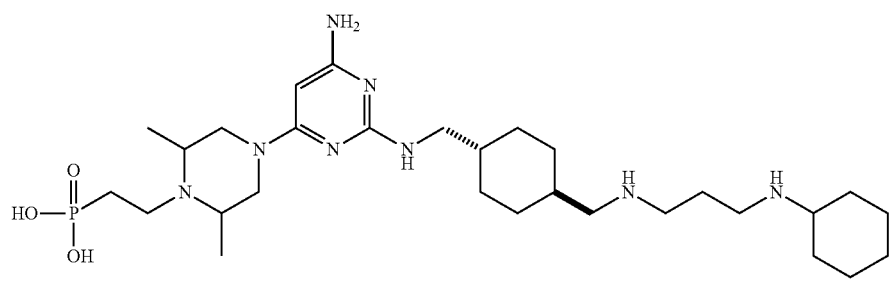
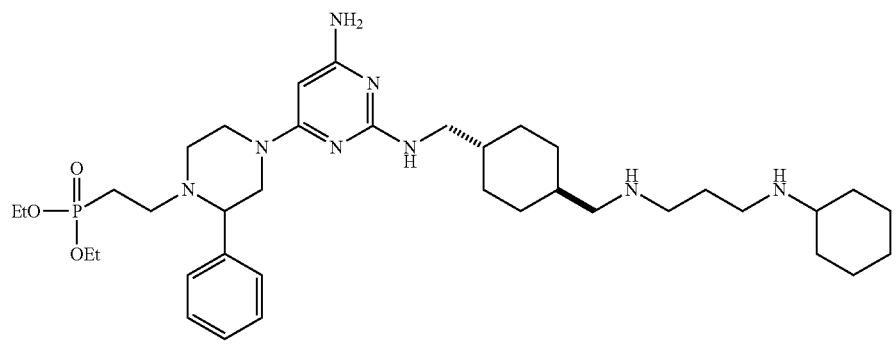
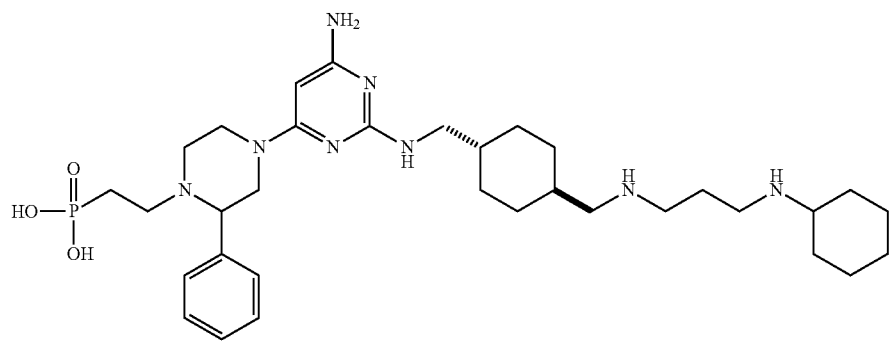

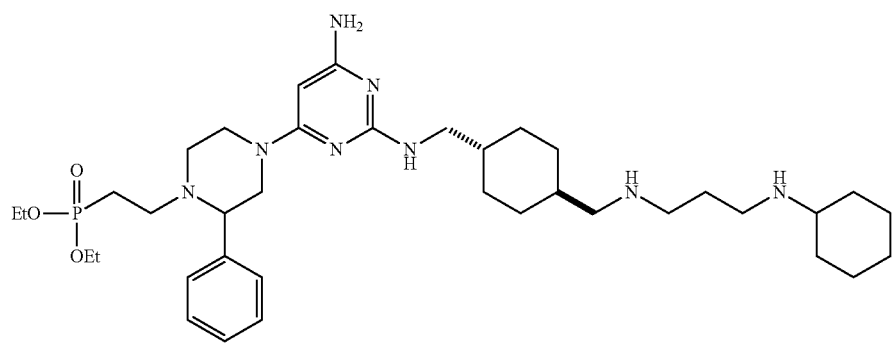
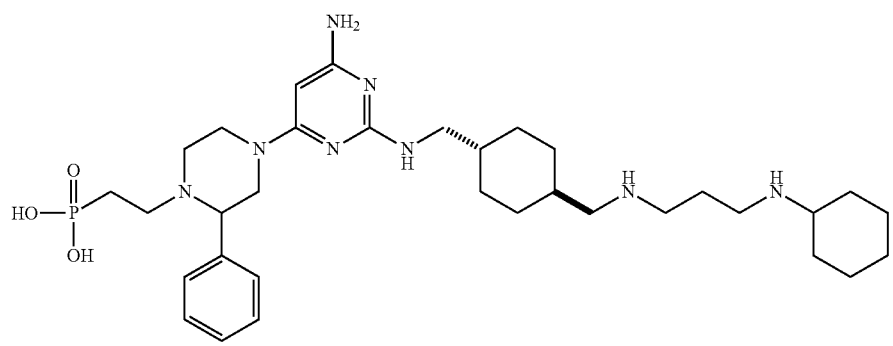
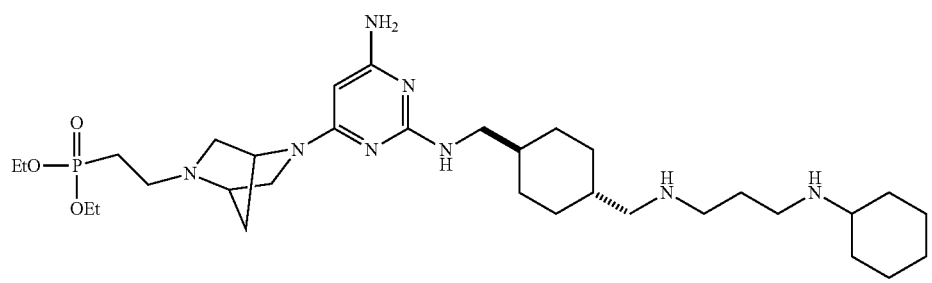
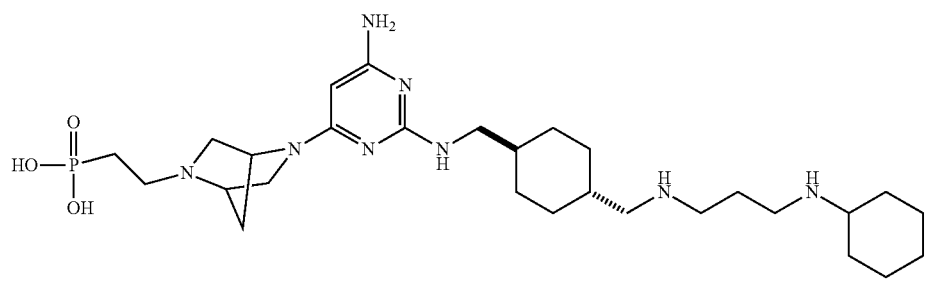
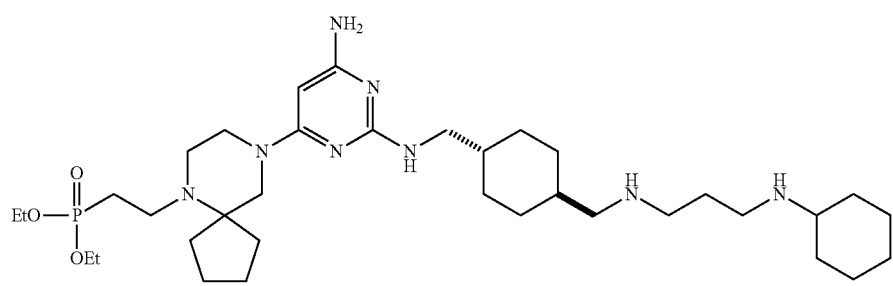

-continued
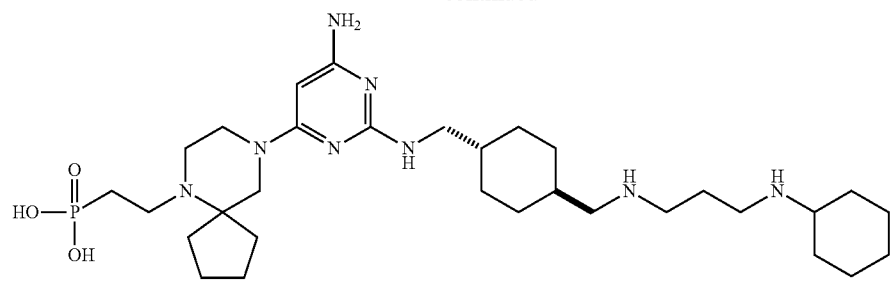
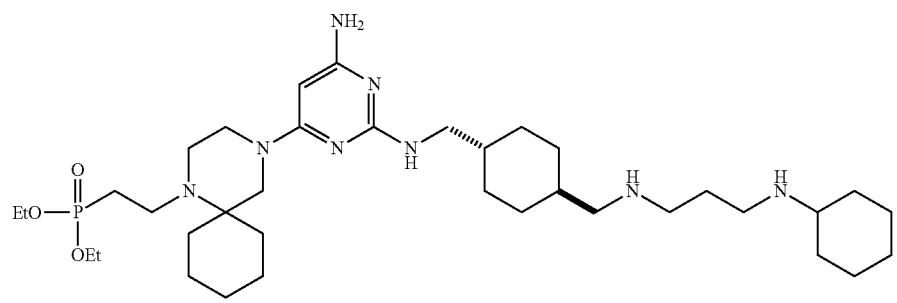
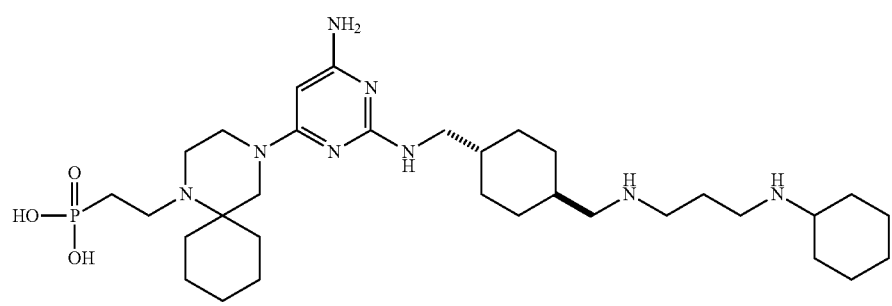
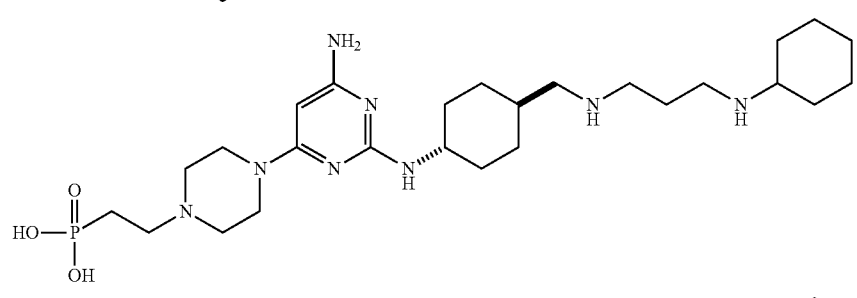
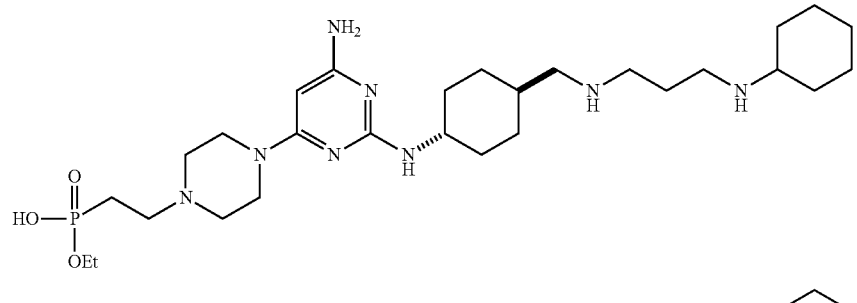
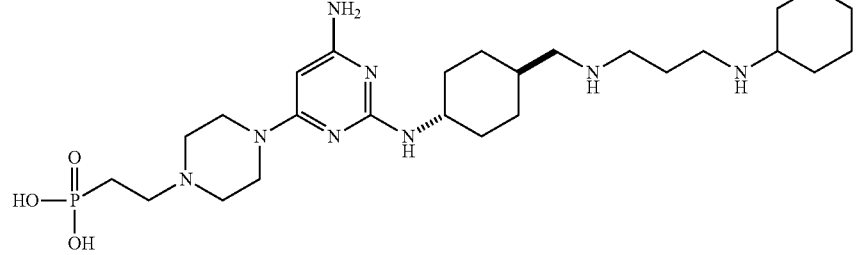

-continued
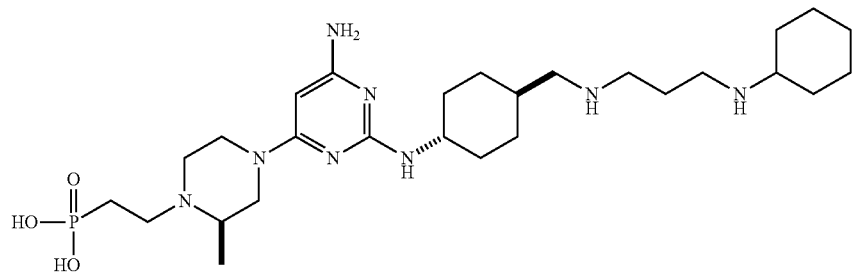
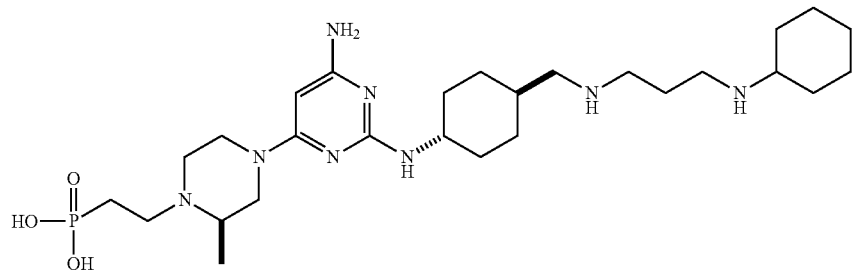
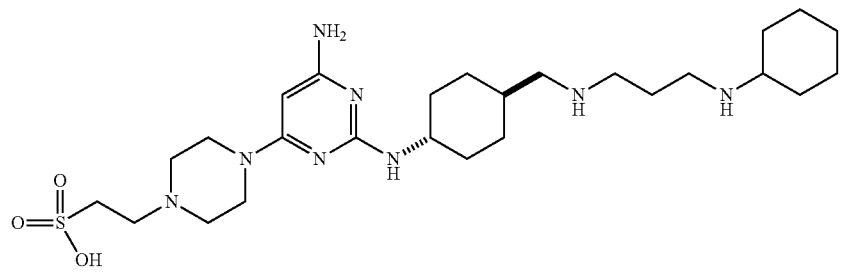
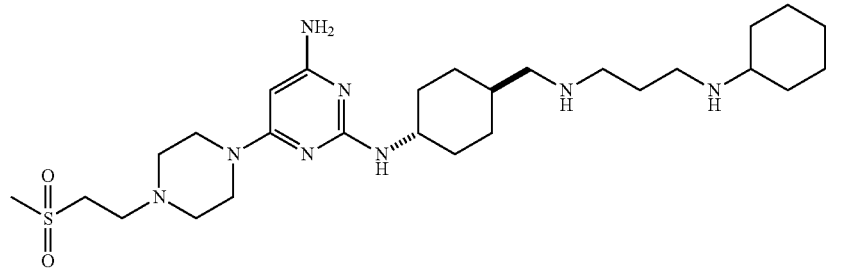
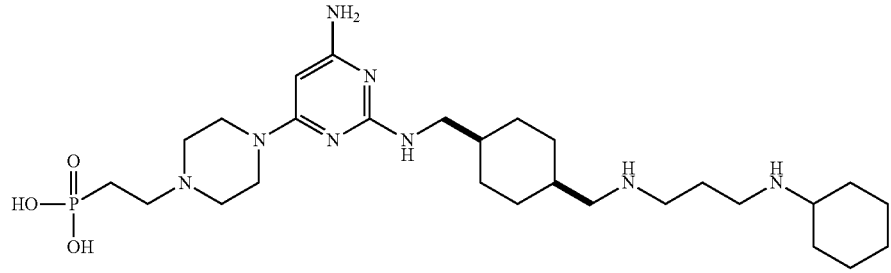
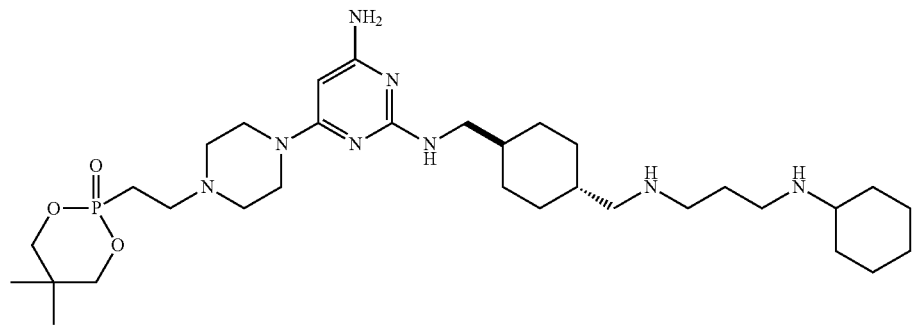

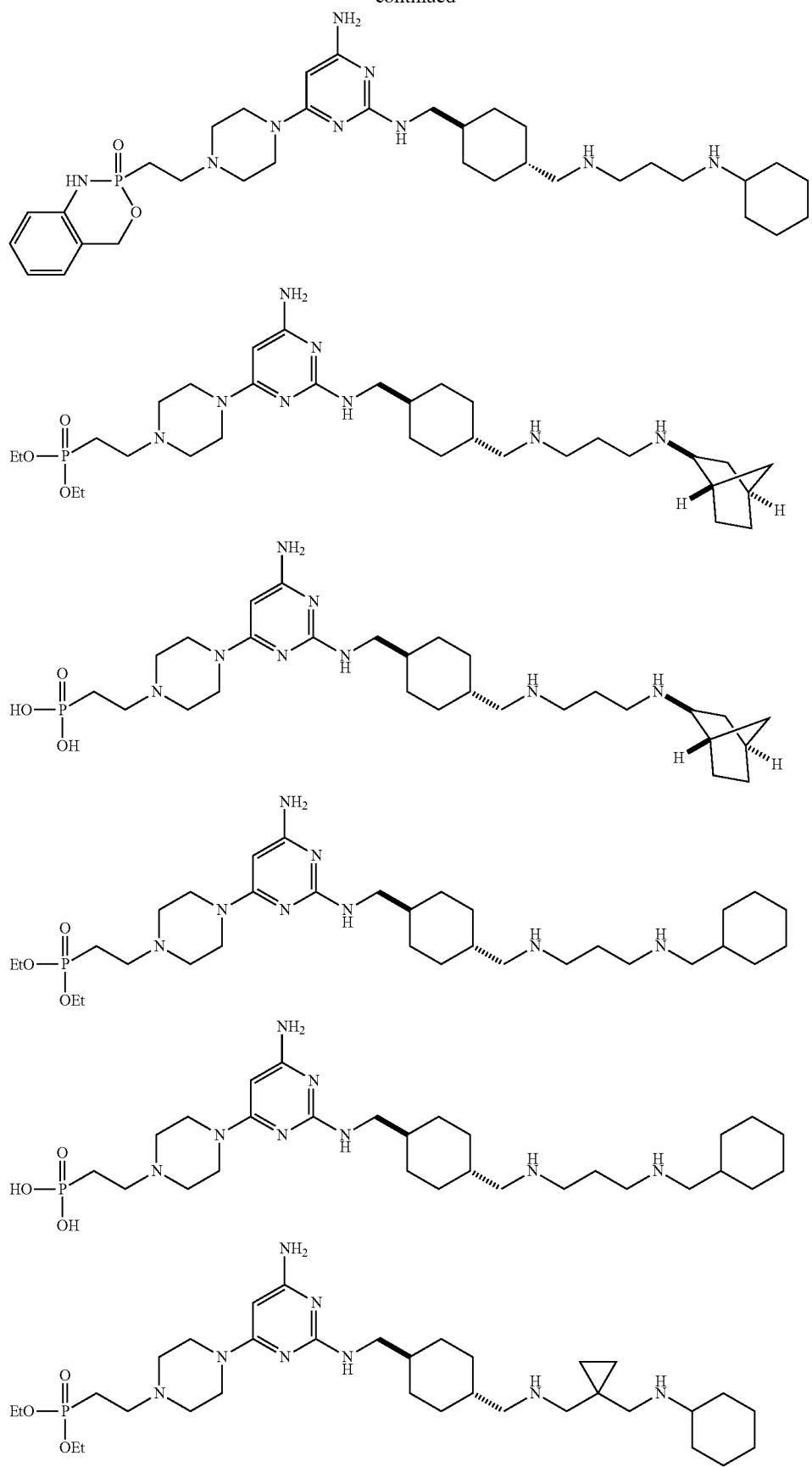

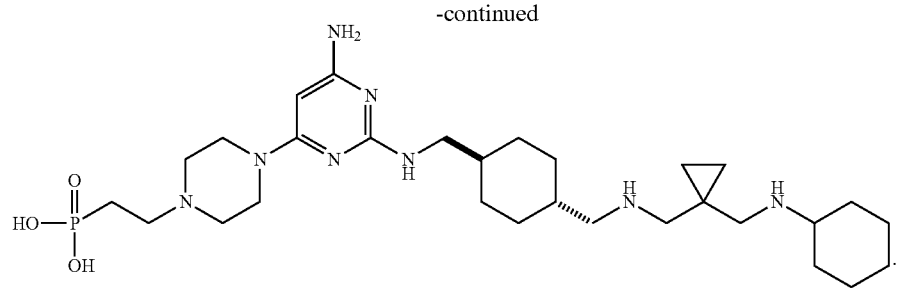
-continued
* * * * *